United States Patent
George et al.

(10) Patent No.: US 12,110,498 B2
(45) Date of Patent: Oct. 8, 2024

(54) COMPOSITIONS AND METHODS FOR GENOMIC INTEGRATION OF NUCLEIC ACIDS INTO EXOGENOUS LANDING PADS

(71) Applicant: AMYRIS, INC., Emeryville, CA (US)

(72) Inventors: Kevin George, Oakland, CA (US); Andrew Main, Benicia, CA (US); Chia-Hong Tsai, Martinez, CA (US)

(73) Assignee: AMYRIS, INC., Emeryville, CA (US)

( * ) Notice: Subject to any disclaimer, the term of this patent is extended or adjusted under 35 U.S.C. 154(b) by 29 days.

(21) Appl. No.: 17/690,429

(22) Filed: Mar. 9, 2022

(65) Prior Publication Data
US 2022/0251606 A1      Aug. 11, 2022

Related U.S. Application Data

(62) Division of application No. 16/302,079, filed as application No. PCT/US2017/033369 on May 18, 2017, now Pat. No. 11,293,033.

(60) Provisional application No. 62/338,412, filed on May 18, 2016.

(51) Int. Cl.
| | |
|---|---|
| C12N 15/70 | (2006.01) |
| C12N 1/19 | (2006.01) |
| C12N 15/10 | (2006.01) |
| C12N 15/81 | (2006.01) |
| C12N 15/90 | (2006.01) |

(52) U.S. Cl.
CPC ......... *C12N 15/905* (2013.01); *C12N 15/102* (2013.01); *C12N 15/1082* (2013.01); *C12N 15/81* (2013.01)

(58) Field of Classification Search
None
See application file for complete search history.

(56) References Cited

U.S. PATENT DOCUMENTS

| | | |
|---|---|---|
| 8,802,921 B2 | 8/2014 | Ainley et al. |
| 2012/0277120 A1 | 11/2012 | Serber et al. |

FOREIGN PATENT DOCUMENTS

| | | |
|---|---|---|
| WO | WO 2003/012036 | 2/2003 |
| WO | WO 2012/149470 A1 | 11/2012 |
| WO | WO 2014/005042 A2 | 1/2014 |
| WO | WO 2014/205192 A2 | 12/2014 |
| WO | WO 2015/095804 A1 | 6/2015 |
| WO | WO 2017/075529 A1 | 5/2017 |

OTHER PUBLICATIONS

International Search report and written opinion mailed on Jan. 26, 2018 for PCT/US2017/033369, 26 pages.
Bahr et al., "Evaluating the effect of chromosomal context on zinc finger nuclease efficiency", BMC Proceedings, Biomed Central Ltd, London, vol. 7, No. Suppl 6, Dec. 4, 2013, p. P3; XP021170326.
Cabaniols et al., "Meganuclease-Driven Targeted Integration in CHO-K1 Cells for the Fast Generation of HTS-Compatible Cell-Based Assays", Journal Of Biomolecular Screening, vol. 15, No. 8, Jul. 12, 2010, pp. 956-967.
Kuhlman et al., "Site-specific chromosomal integration of large synthetic constructs", Nucleic Acids Research, Oxford University, Press, GB, vol. 38, No. 6, Apr. 1, 2010, e92, 10 pages; XP002666135.
Yachie et al., "Pooled-matrix protein interaction screens using Barcode Fusion Genetics", Molecular Systems Biology, vol. 12, No. 4, Apr. 22, 2016, pp. 863-863.
Zhu et al., "Dice, an efficient system for iterative genomic editing in human pluripotent stem cells", Nucleic Acids Research, Dec. 4, 2013, XP055106313; ISSN: 0305-1048, DOI: 10.1093/nar/gkt1290; abstract; figure 1.
Notice of Reasons for Rejection for JP application No. 2018-560571 dated Jun. 9, 2021 together with its English translation; 11 pages.
Extended European search report for the EP patent Application No. 23150787.2 dated Jul. 7, 2023; 12 pages.
Eauclaire et al., "Combinatorial metabolic pathway assembly in the yeast genome with RNA-guided Cas9", J Ind Microbiol Biotechnol (2016) 43:1001-1015; DOI 10.1007/s10295-016-1776-0.
Fu et al., "Hot Fusion: An Efficient Method to Clone Multiple DNA Fragments as Well as Inverted Repeats without Ligase", PLOS ONE, DOI:10.1371/journal.pone.0115318 Dec. 31, 2014.
Gibson et al., "One-step assembly in yeast of 25 overlapping DNA fragments to form a complete synthetic Mycoplasma genitalium genome", PNAS, Dec. 23, 2008, vol. 105, No. 51, pp. 20404-20409.
Kuijpers et al., "One-step assembly and targeted integration of multigene constructs assisted by the I-SceI meganuclease in *Saccharomyces cerevisiae*", FEMS Yeast Res 13 (2013) 769-781; DOI:10.1111/1567-1364.12087.

*Primary Examiner* — Celine X Qian
(74) *Attorney, Agent, or Firm* — SQUIRE PATTON BOGGS (US) LLP

(57) ABSTRACT

Provided herein are compositions and methods of integrating one or more exogenous donor nucleic acids into one or more exogenous landing pads engineered into a host cell's genome. In certain embodiments, the exogenous landing pads and exogenous donor nucleic acids comprise standardized, compatible homology regions so that exogenous donor nucleic acids can integrate into any of the landing pads, independent of the genomic sequences surrounding the landing pads. In certain embodiments, the methods comprise contacting the host cell comprising landing pads with one or more exogenous donor nucleic acids, and a nuclease capable of causing a double-strand break within the landing pads, and recovering a host cell comprising one or more exogenous donor nucleic acids integrated in any of the landing pads.

17 Claims, 15 Drawing Sheets
Specification includes a Sequence Listing.

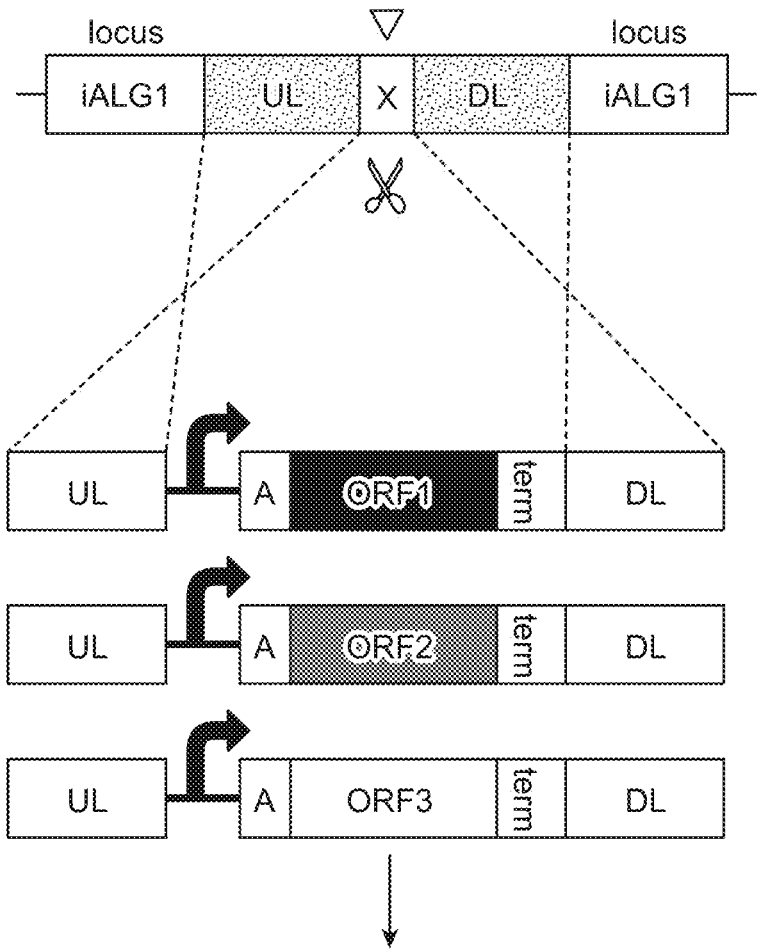
FIG. 1A
FIG. 1B
FIG. 1C

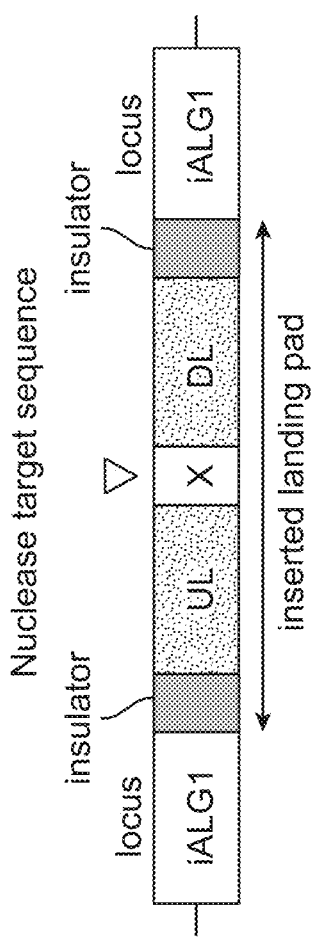
FIG. 1D
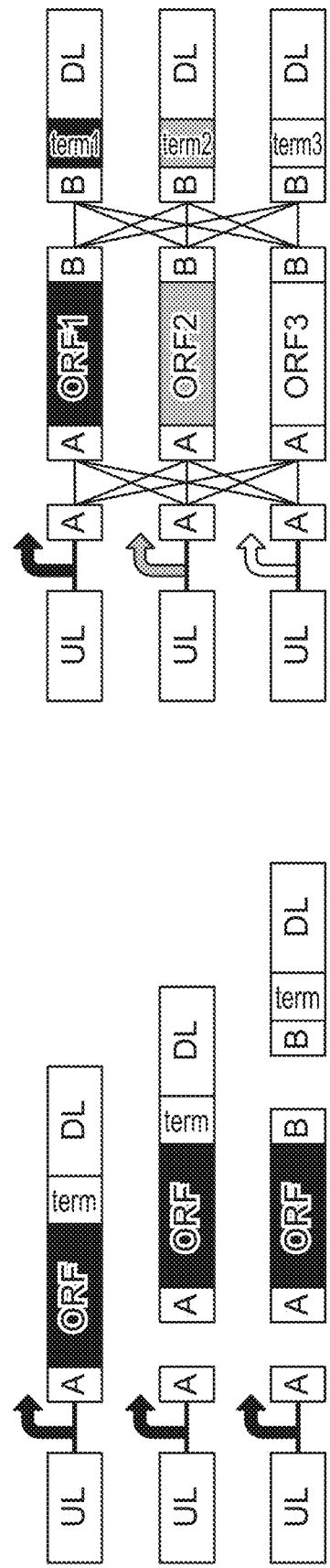
FIG. 1E
FIG. 1F

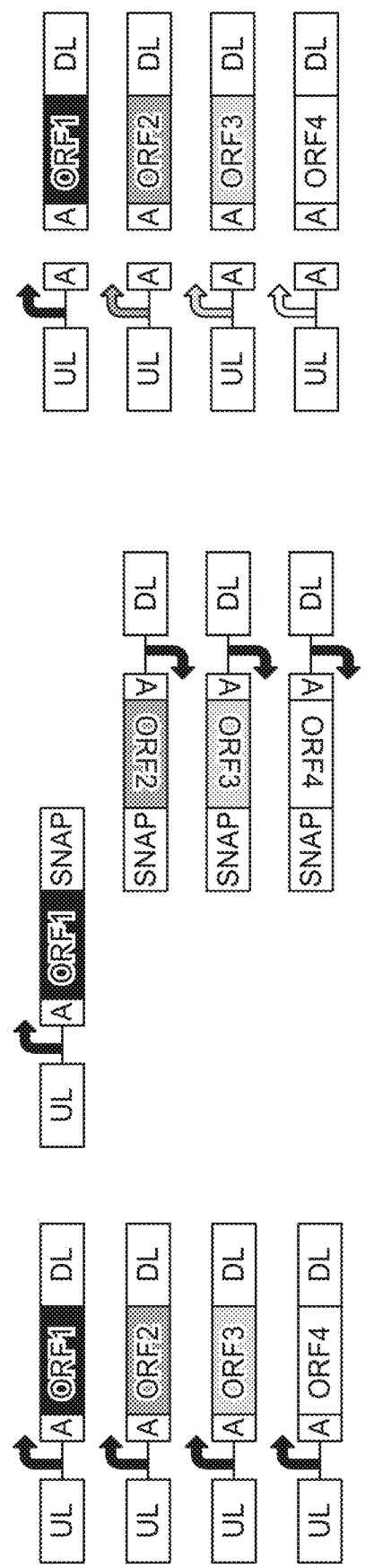
FIG. 2A
FIG. 2B
FIG. 2C
FIG. 2D

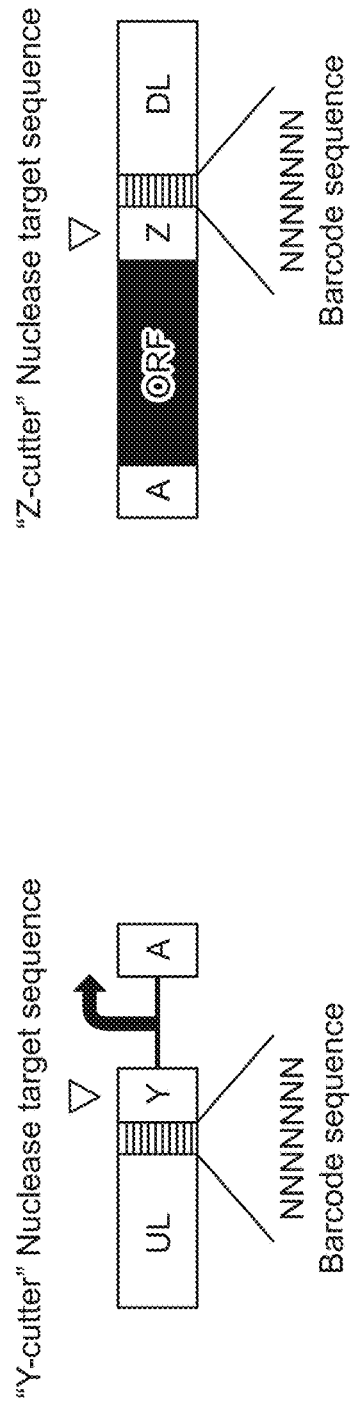
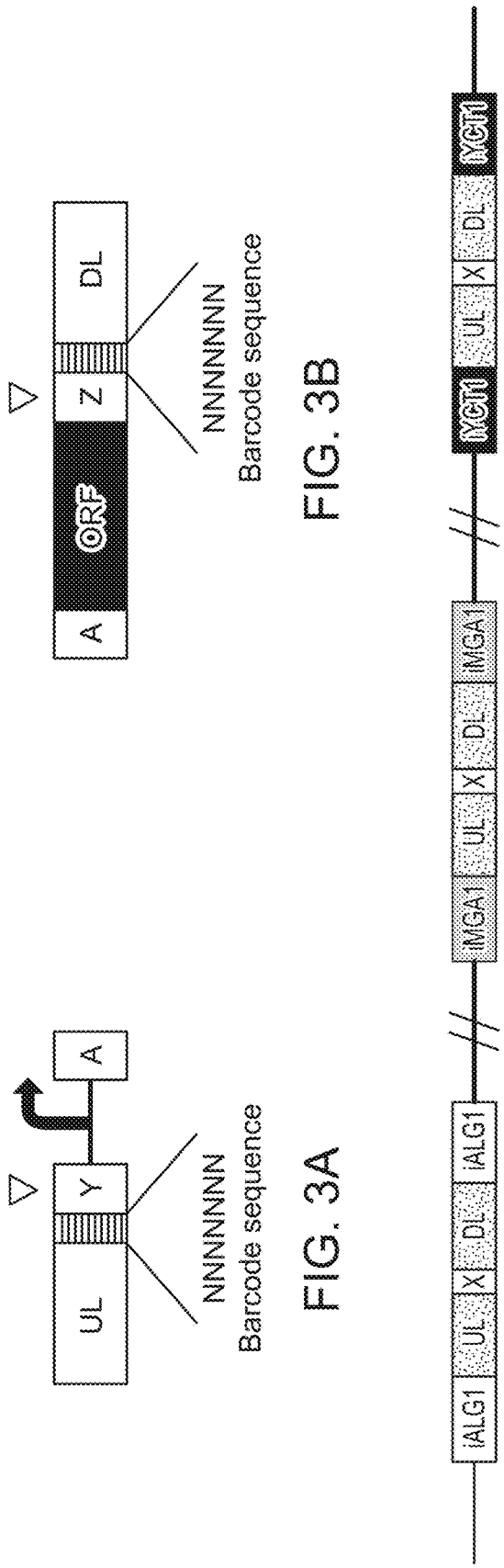
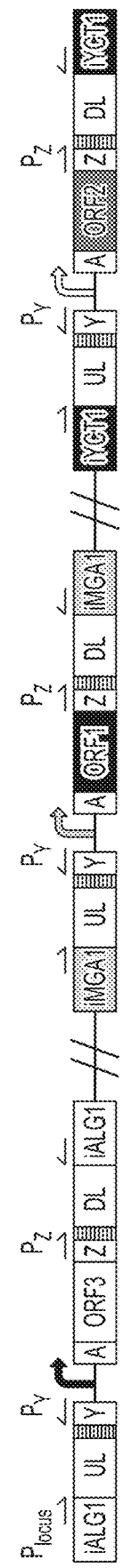
FIG. 3A
FIG. 3B
FIG. 3C
FIG. 3D
"Y" and "Z" nuclease target sequences serve as common primer binding sites for barcode amplification and allow for additional rounds of cutting and nucleotide integration

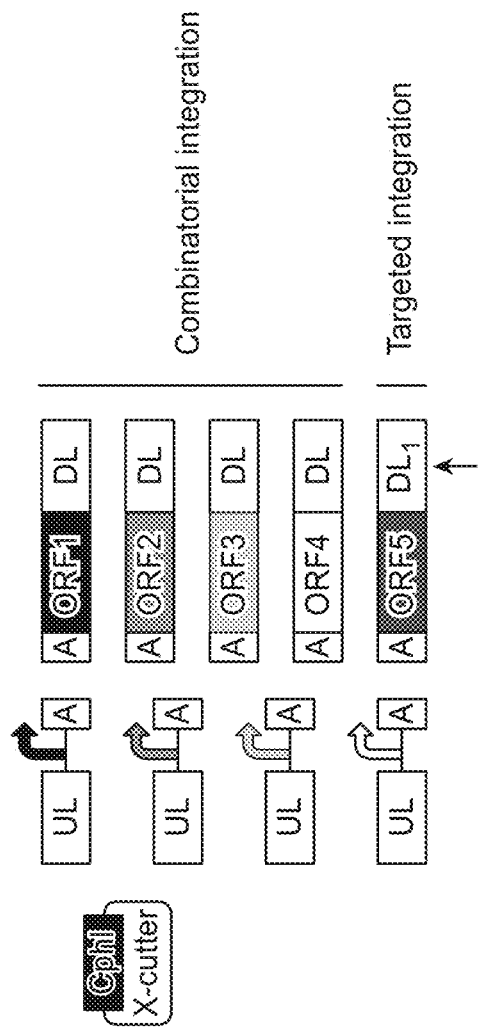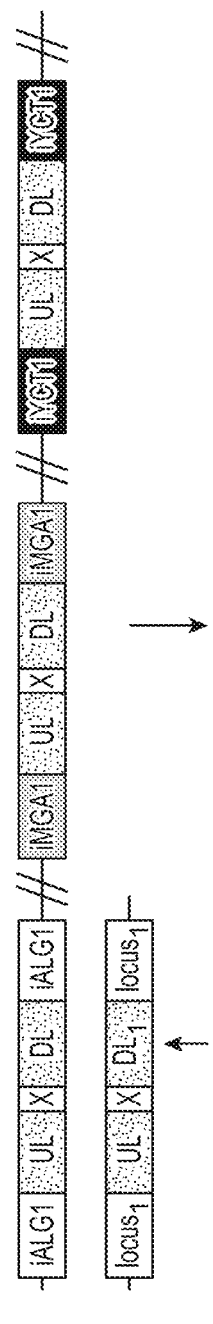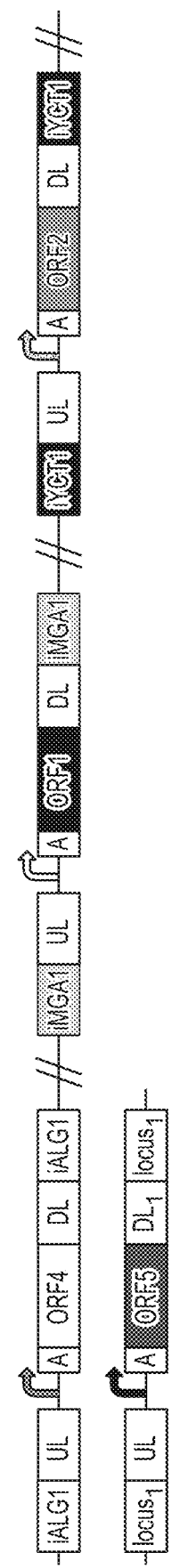
FIG. 5A
FIG. 5B

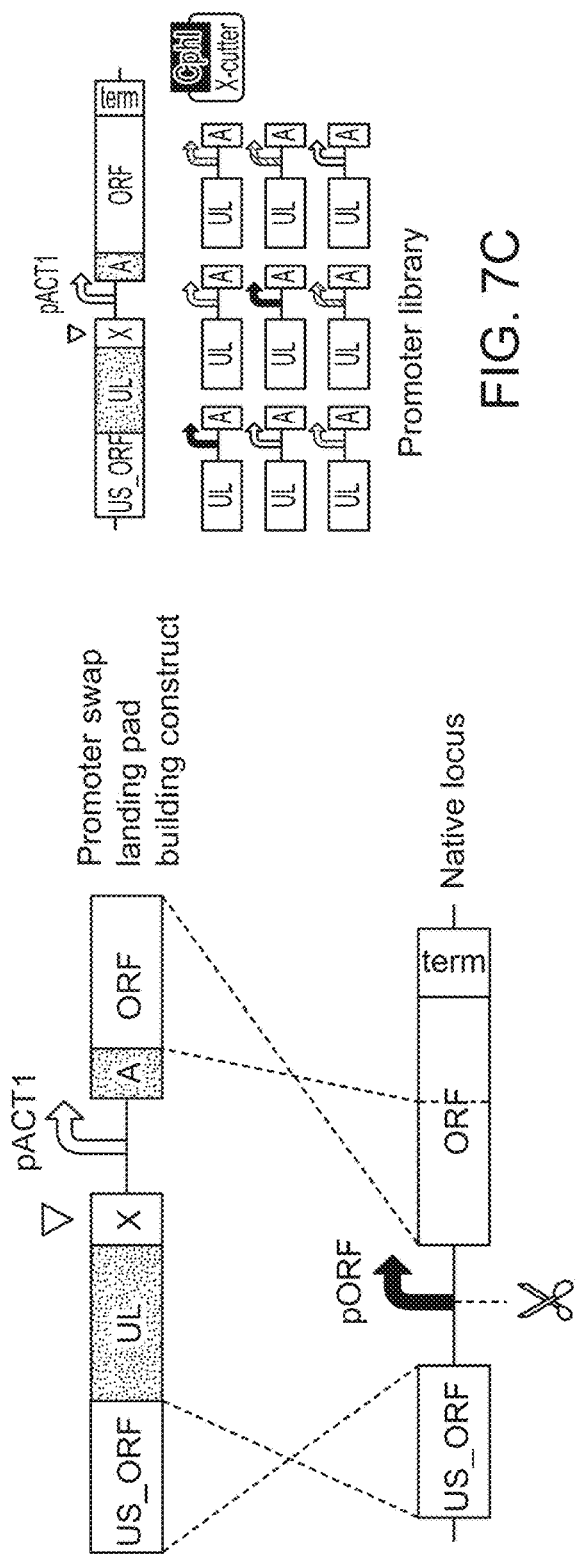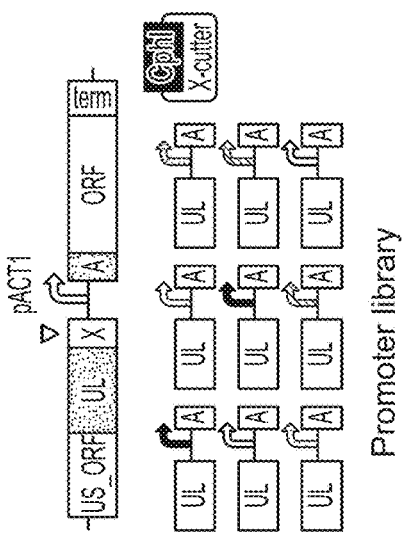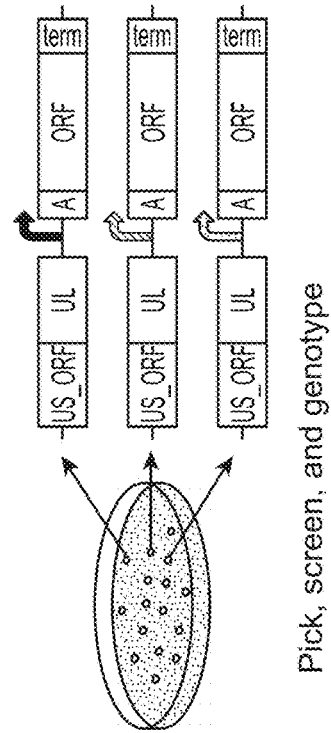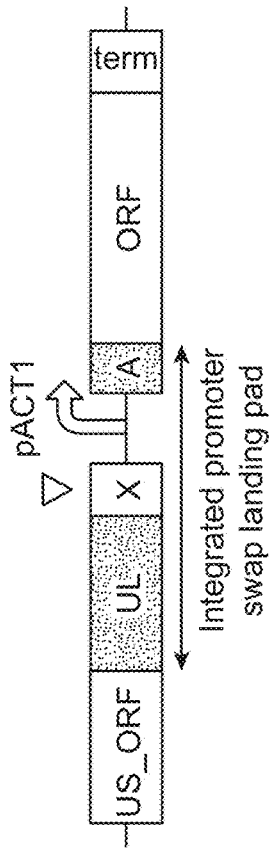

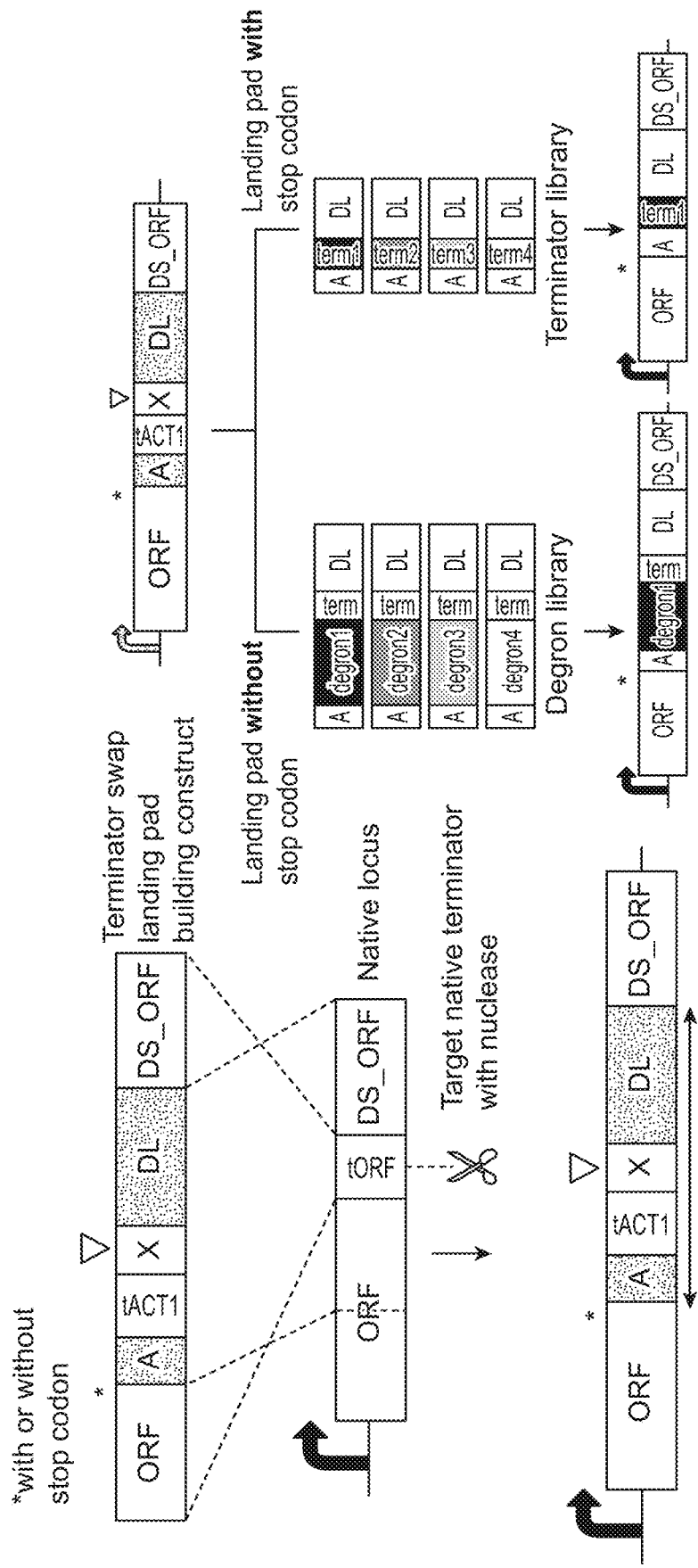

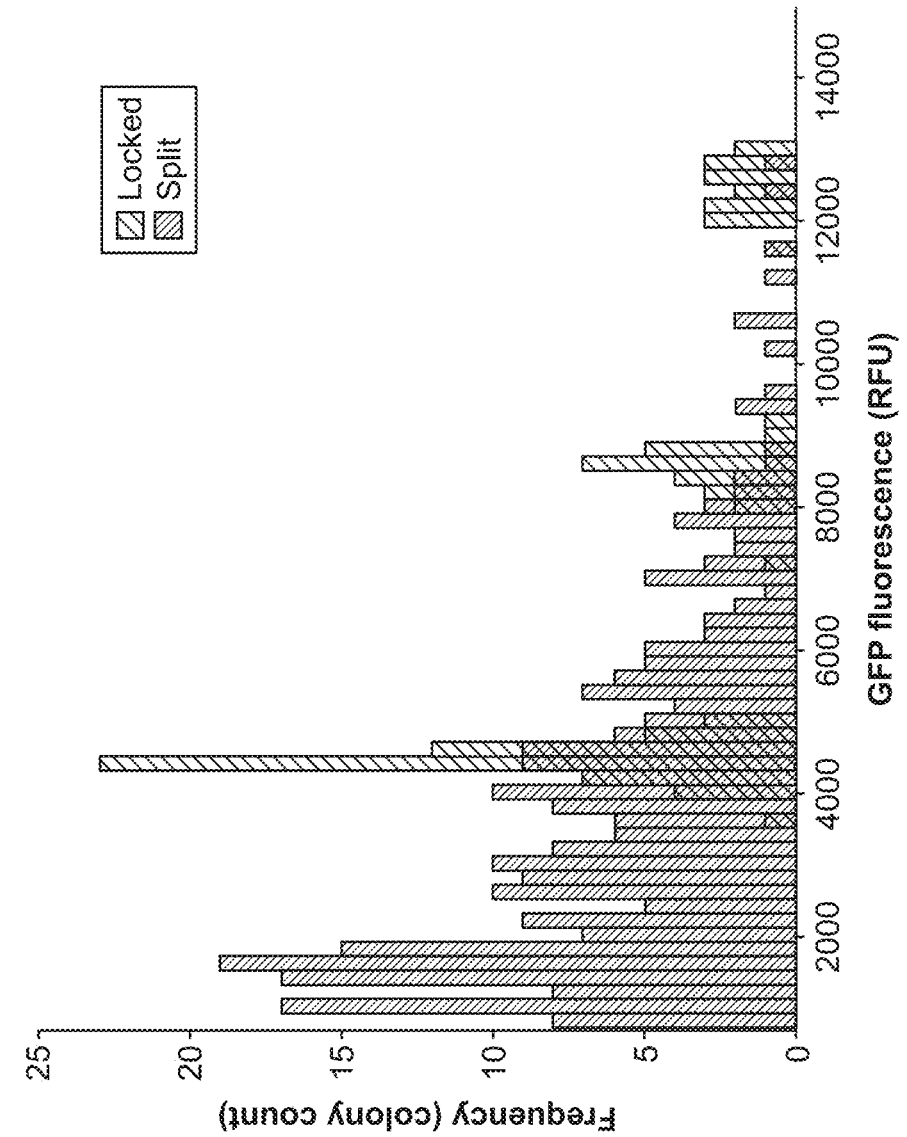
FIG. 10C
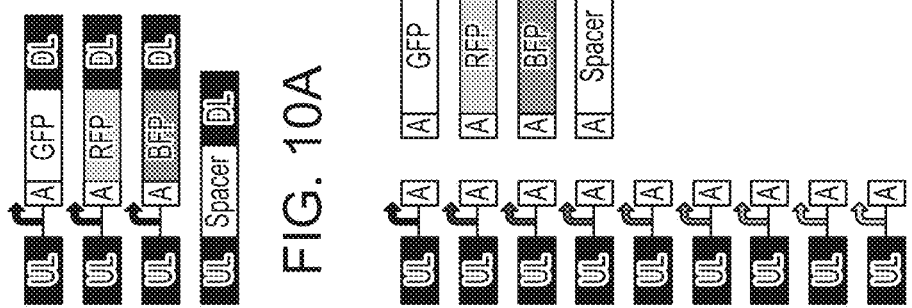
FIG. 10A
FIG. 10B

Table I. Integration efficiency using CLiX

| Strain ID | Strain A | Strain A | Strain B | Strain C |
| --- | --- | --- | --- | --- |
| UL/DL length | 500 bp | 500 bp | 200 bp | 100 bp |
| Stitch design | Locked | Split | Split | Split |
| Number of colony | 96 | 96 | 96 | 96 |
| Number of locus | 288 | 288 | 288 | 288 |
| Integration w/ indels | 0 | 3 | 9 | 7 |
| No integration | 0 | 3 | 3 | 0 |
| Correct integration | 288 | 282 | 276 | 281 |
| Success rate | 100% | 97.9% | 95.8% | 97.6% |

Strain A, Strain B, and Strain C are derived from same naive strain, and all have three CliX landing pads located in the downstream intergenic regions of ALG1, MGA1 and YCT1. Integrations were validated by cPCR, fluorescence measurement, and Sanger sequencing. UL, upstream library; DL, downstream library

FIG. 11

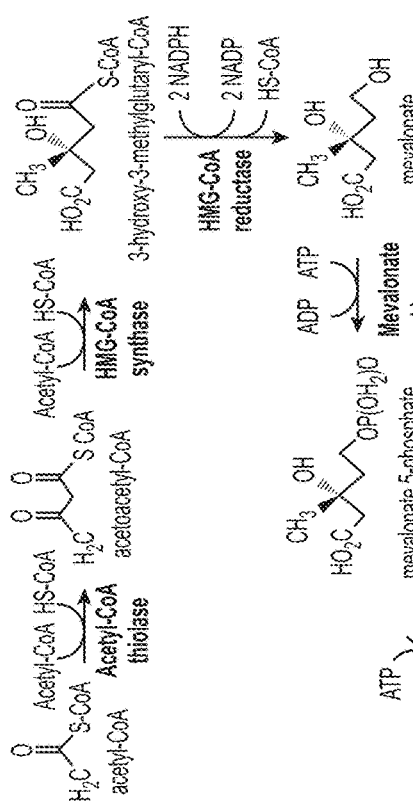
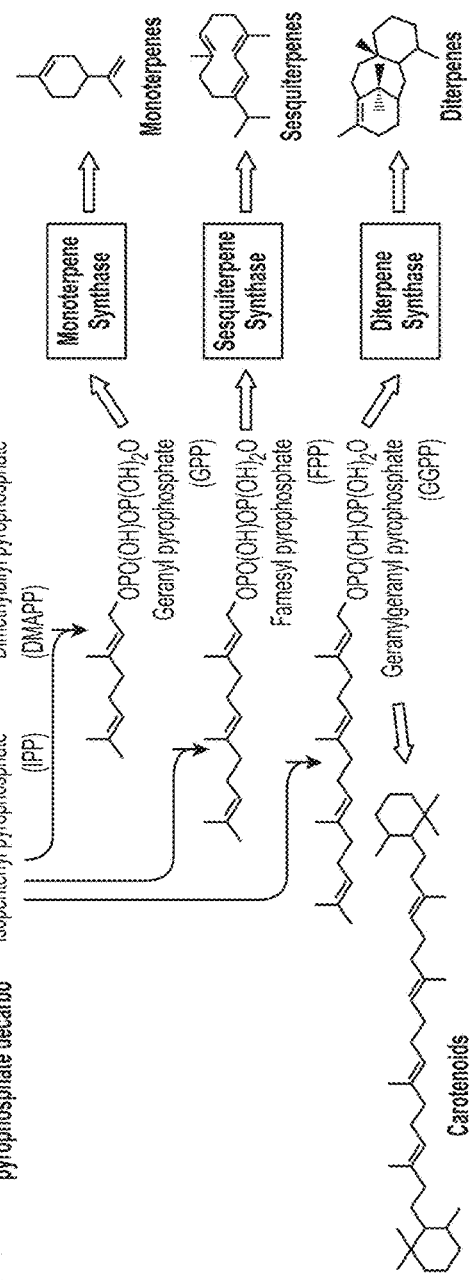
FIG. 13

COMPOSITIONS AND METHODS FOR GENOMIC INTEGRATION OF NUCLEIC ACIDS INTO EXOGENOUS LANDING PADS

1. CROSS REFERENCE TO RELATED APPLICATIONS

This application is a Divisional application of U.S. patent application Ser. No. 16/302,079, filed Nov. 15, 2018, which is the U.S. National Stage entry of International Application No. PCT/US2017/033369, filed May 18, 2017, which claims the benefit of U.S. Provisional Application No. 62/338,412, filed May 18, 2016, the contents of these applications are hereby incorporated by reference in their entireties.

2. FIELD OF THE INVENTION

The compositions and methods provided herein generally relate to the fields of molecular biology and genetic engineering.

3. BACKGROUND

Genetic engineering techniques have been used to introduce modifications to a host cell's genome in various fields. In the field of synthetic biology, engineering microorganisms to produce target molecules often involves the introduction and integration of a number of different nucleic acids into a host cell's genome. Industrial microorganisms for fermentation are heavily genetically modified, and the use of standard techniques to engineer complex biosynthetic pathways for production of target molecules de novo can consume an enormous amount of time and resources. Furthermore, once a strain is engineered to produce target molecules, additional gains in performance often require the simultaneous modification of multiple parameters (e.g., overexpression of multiple genes coupled with down regulation of others) rather than single-target designs.

Generally, a combinatorial strategy for modifying multiple parameters will be pre-determined by a strain engineer. For example, a strain engineer will manually determine which combination of nucleic acid constructs to introduce into a host cell to improve its phenotype. To cover a large combinatorial search space, however, hundreds or thousands of pre-determined combinations of nucleic acid constructs will need to be constructed, transformed into host cells, and screened. Screening such a large combination of nucleic acid constructs to empirically determine an optimal combination will be time consuming. For example, the screening process will include transforming host cells with hundreds or thousands of combinations of nucleic acid constructs, verifying each transformation with PCR, and analyzing the phenotypes of resulting transformed host cells. In many cases, re-using nucleic acid constructs may be problematic in different host cell backgrounds, which may lack suitable homology regions for recombination, or will be limited by the availability of "open" neutral genomic loci into which nucleic acid constructs can integrate without negatively impacting the host cell function.

Therefore, there is a need for improved methods and compositions for introduction and integration of nucleic acid constructs into a host cell. There is also a need for improved methods and compositions for combinatorial integration of nucleic acid constructs to modulate the host cell phenotype and/or the production of target molecules.

4. SUMMARY

Genomic integration of exogenous donor nucleic acids via host cell-mediated recombination typically requires each exogenous donor nucleic acid to have genomic site-specific homology sequences. These sequences allow exogenous donor nucleic acids to homologously recombine at specific genomic sites. If it is desired to integrate an exogenous donor nucleic acid at a different genomic site or in a different host cell background, the exogenous donor nucleic acid needs to be modified and re-customized to include homology sequences compatible with the new genomic site for integration. Such customization is time and resource consuming.

Thus, in one aspect, provided herein are compositions and methods that minimize re-customization of exogenous donor nucleic acids for integration into the host cell's genome. In one embodiment, a host cell's genome is modified to comprise a landing pad which can be used to further facilitate integration of exogenous donor nucleic acids comprising standardized homology sequences. The landing pad engineered into the host cell's genome comprises landing pad homology sequences which are capable of homologously recombining with the standardized homology sequences of the exogenous donor nucleic acids. In certain embodiments, since the exogenous donor nucleic acids comprise standardized homology sequences which do not rely on genomic site-specific homology sequences for genomic integration, the exogenous donor nucleic acids do not need to be re-customized and can be re-used in different host cell backgrounds or at different genomic loci as long as compatible landing pads exist.

In particular embodiments, each landing pad in the host cell's genome further comprises a nuclease target sequence (NTS) positioned between an upstream landing pad homology sequence (ULP) and a downstream landing pad homology sequence (DLP). In particular embodiments, the nuclease target sequence (NTS) comprises a nucleotide sequence that is recognized and cleavable by a site-specific nuclease. The host cell with an exogenous landing pad can be contacted with the site-specific nuclease simultaneously with exogenous donor nucleic acids (ES) comprising homology sequences compatible with the landing pad homology sequences. The nuclease will cause targeted double-strand breaks at the landing pad, which will result in a significant increase in (ES) integration efficiencies, as compared to host cells which are not contacted with the nuclease.

In particular embodiments, exogenous donor nucleic acids are modular DNA parts (also referred to as component polynucleotides). In certain embodiments, a single component polynucleotide on its own does not have all the homology sequences for homologously recombining at a landing pad in the host cell's genome. However, when a host cell is contacted with a plurality of component polynucleotides, two or more of these component polynucleotides with compatible linker sequences can homologously recombine in vivo to generate assembled component polynucleotides. The assembled component polynucleotides, which, then comprise homology sequences compatible with the landing pad homology sequences, can homologously recombine at the landing pad. Since component polynucleotides can combinatorially recombine with one another, the use of component polynucleotides can generate a much greater molecular diversity for high-throughput integration and screening of exogenous donor nucleic acids, as compared to a single piece exogenous donor nucleic acids that are targeted to a specific genomic locus.

In another aspect, a host cell is provided with a plurality of standardized landing pads engineered into the host cell's genome. The term "standardized" landing pads is used herein to refer to a plurality of landing pads, wherein each landing pad comprises a pair of landing pad homology sequences (ULP) and (DLP), which is identical or substantially identical to those in other landing pads. In certain embodiments, when exogenous donor nucleic acids are also standardized with compatible homology regions at their 5' and 3' regions, they can homologously recombine with their respective landing pad homology sequences. The exogenous donor nucleic acids can randomly integrate at any of the standardized landing pads in the host cell's genome. The randomness of integration of exogenous donor nucleic acids into any of the standardized landing pads can provide a powerful tool to rapidly and combinatorially integrate a large quantity or library of exogenous donor nucleic acids.

For instance, with 30 exogenous donor nucleic acids and three standardized landing pads integrated in the host cell's genome, any of the 30 exogenous donor nucleic acids can integrate into any of the three standardized landing pads, resulting in a population of host cells with potentially 27,000 different combinations of exogenous donor nucleic acids integrated into the host cell's genome. On the other hand, with 30 exogenous donor nucleic acids designed to be integrated into three genome specific integration sites, one can generate a population of host cells with potentially 1000 different combinations of exogenous donor nucleic acids integrated into the host cell's genome.

The combinatorial integration diversity can be further enhanced by utilizing component polynucleotides as exogenous donor nucleic acids to be integrated into the host cell's genome. For example, if each exogenous donor nucleic acid is introduced into the host cell as two component polynucleotides in the example illustrated above, it can generate a population of host cells with potentially 216,000 different combinations of genotypes. The randomness of integration of assembled component polynucleotides into any of the standardized landing pads (rather than at specific genomic sites) further enhances the molecular diversity of donor nucleic acids integrated into the host cell's genome. Therefore, it can result in an even greater variation of phenotypes, including desired traits, exhibited by modified host cells.

Thus, in one aspect, provided herein is a host cell comprising one or more (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP). In certain embodiments, the number (x) of exogenous landing pads in the host cell's genome can be any suitable number between about 1 and about 100, between about 2 and about 50, between about 3 and about 20, and the like. In certain embodiments, all the landing pads comprise standardized landing pad homology sequences so that exogenous donor nucleic acids with compatible homology sequences can integrate at any of the standardized landing pads via host cell-mediated homologous recombination. In certain embodiments, the landing pads are integrated at selected neutral loci in the host cell's genome. In particular embodiments, the landing pads are integrated at intergenic regions in the host cell's genome.

In another aspect, provided herein are one or more exogenous donor nucleic acids (ES), wherein each exogenous donor nucleic acid comprises a nucleic acid of interest (D) positioned between an upstream library sequence (UL) and a downstream library sequence (DL), wherein each (UL) is capable of homologously recombining at any (ULP), and wherein each (DL) is capable of homologously recombining at any (DLP), of the (x) exogenous landing pads. In certain embodiments, exogenous donor nucleic acids (ES) comprise the upstream library sequences (UL) that are identical to one another and the downstream library sequence (DL) that are identical to one another. In certain embodiments, exogenous donor nucleic acids (ES) are capable of integrating at any of the exogenous landing pads, independent of endogenous genomic sequences surrounding each landing pad.

In another aspect, provided herein are methods for integrating exogenous donor nucleic acids into a host cell's genome. In certain embodiments, the method comprises:

(a) contacting a host cell, the host cell comprising a plurality of (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), with:

(i) one or more exogenous donor nucleic acids (ES), wherein each (ES) comprises a nucleic acid of interest (D) positioned between an upstream library sequence (UL) and a downstream library sequence (DL), wherein each (UL) is capable of homologously recombining at any (ULP), and each (DL) is capable of homologously recombining at any (DLP), of any of the (x) exogenous landing pads; and (ii) one or more nucleases (N) capable of binding to the (NTS) and cleaving a site within the one or more (x) exogenous landing pads; and (b) recovering a host cell generated from the contacted host cell, wherein any of the exogenous donor nucleic acids (ES) is integrated at any of the (x) exogenous landing pads, independent of genomic sequences surrounding each landing pad. In some embodiments, x is an integer of at least two. In certain embodiments, at least two or more exogenous donor nucleic acids comprise the upstream library sequences (UL) that are identical to one another and the downstream library sequences (DL) that are identical to one another.

In certain embodiments, each of the upstream landing pad homology sequences (ULP) and the downstream landing pad homology sequence (DLP) comprises about 100, about 200, or about 500 base pairs of homology with each of the upstream library sequence (UL) and the downstream library sequence (DL), respectively. In certain embodiments, each of the upstream library sequences (UL) and the downstream library sequences (DL) of exogenous donor nucleic acids is about 500 base pairs in length.

In certain embodiments, two or more of the exogenous donor nucleic acids are component polynucleotides which are co-transformed into a host cell. In an embodiment, the methods comprise:

(a) contacting a host cell, the host cell comprising one or more (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), with:

(i) one or more first component polynucleotides, wherein each first component polynucleotide comprises, in a 5' to 3' orientation:

(1) an upstream library sequence (UL) capable of homologously recombining with any (ULP) of the one or more (x) exogenous landing pads;

(2) a first nucleic acid of interest, and (3) a first linker sequence;

(ii) one or more last component polynucleotides, wherein each last component polynucleotide comprises, in a 5' to 3' orientation:
   (1) a last linker sequence,
   (2) a last nucleic acid of interest, and
   (3) a downstream library sequence (DL) capable of homologously recombining with any (DLP) of any of the one or more (x) exogenous landing pads,
   wherein any first linker sequence of the one or more first component polynucleotides is capable of homologously recombining with any last linker sequence of the one or more last component polynucleotides; and
(iii) one or more nucleases (N) capable of binding to (NTS) and cleaving a site within the one or more (x) exogenous landing pads; and (b) recovering a host cell generated from the contacted host cell, wherein any combination of a first component polynucleotide from the one or more first component polynucleotides and a last component polynucleotide from the one or more last component polynucleotides, which are homologously recombined in vivo via their linker sequences, is integrated at any of the one or more (x) exogenous landing pads, independent of genomic sequences surrounding each landing pad. In certain embodiments, x is an integer of at least one. In certain embodiments, x is an integer of at least two.

In some embodiments, three or more component polynucleotides are co-transformed into a host cell for integration at the landing pads. In an embodiment, component polynucleotides comprise: (a) one or more first component polynucleotides, wherein each first component polynucleotide comprises, in a 5' to 3' orientation, an upstream library sequence capable of homologously recombining with the upstream landing pad homology sequence (ULP), any DNA segment selected from the group $D_0$, a linker sequence $LB_0$; one or more intermediate component polynucleotides, wherein each intermediate component polynucleotide comprises, in a 5' to 3' orientation, a first linker sequence $LA_n$, any DNA segment selected from the group $D_n$, a second linker sequence $LB_n$, wherein n represents an integer from one to the number of intermediate component polynucleotides; and (c) one or more last component polynucleotides, wherein each last component polynucleotide comprises, in a 5' to 3' orientation, a linker sequence $LA_m$, any DNA segment selected from the group $D_m$, and a downstream library sequence capable of homologously recombining with the downstream landing pad homology sequence $(DLP)_s$. In such embodiments, each linker sequence $LB_{(p-1)}$ is capable of homologously recombining with the linker sequence $LA_p$, wherein n is an integer that varies from 1 to (m−1), wherein p represents an integer from 1 to m, and wherein each group $D_0, \ldots D_n, \ldots D_m$, independently consists of one or more DNA segments. In this embodiment, any combination of a first component polynucleotide from the one or more first component polynucleotides, an intermediate component polynucleotide from the one or more intermediate component polynucleotides, and a last component polynucleotide from the one or more last component polynucleotides, which are homologously recombined in vivo via their linker sequences, is integrated at any of the one or more (x) exogenous landing pads, independent of genomic sequences surrounding each landing pad. In some embodiments, x is an integer of at least one. In some embodiments, x is an integer of at least two.

In another aspect, the method of genomic integration comprises contacting a cell with any combination of (a1) one or more exogenous donor nucleic acids (ES), (a2) one or more first component polynucleotides and one or more last component polynucleotides, and (a3) one or more first component polynucleotides, one or more intermediate component polynucleotides, and one or more last component polynucleotides described herein.

In another aspect, some of the landing pads integrated in the host cell's genome are designed to target a specific genomic locus. For example, a targeted landing pad can be integrated adjacent to an endogenous gene at its native locus. Such targeted landing pads can be used to screen a promoter library to titrate expression of the endogenous gene to determine an optimal promoter. In another example, a targeted landing pad can be integrated 3' to an open reading frame of a gene of interest to screen a terminator library or a degron library. In these embodiments, component polynucleotides comprising standardized library or linker sequences compatible with the targeted landing pad can be used. In certain embodiments, the targeted landing pad can be used in combination with one or more standardized exogenous landing pads, which can be used to integrate any exogenous donor nucleic acids, independent of the genomic sequences surrounding the standardized exogenous landing pads.

In another aspect, provided herein is a method of determining phenotype contributions by exogenous donor nucleic acids. In certain embodiments, the method comprises: (a) contacting a host cell with a plurality of exogenous nucleic acids (ES), each (ES) tagged with a barcode sequence, wherein the host cell's genome is configured to integrate any one or combinations of the plurality of (ES) in the host cell's genome via host cell-mediated homologous recombination; (b) screening host cells, generated from the contacted host cell, which exhibit a specific phenotype; and (c) determining, using the barcode sequence associated with each (ES), identities of (ES) integrated in the host cell's genome. In certain embodiments, at least two of the plurality of exogenous donor nucleic acids (ES) are component polynucleotides with compatible linker sequences. The component polynucleotides homologously recombine in vivo to generate assembled component polynucleotides, which are integrated at the landing pads via host cell-mediated homologous recombination. Each component polynucleotide is individually tagged with a barcode sequence, which can be used to determine which combinations of component polynucleotides are integrated in the landing pads.

In another aspect, provided herein is a modified host cell comprising one or more landing pads described herein.

In another aspect, provided herein is a kit useful for performing genomic integration of exogenous nucleic acids. In some embodiments, the kit comprises: (a) one or more host cells described herein; (b) one or more exogenous donor nucleic acids described herein; and/or (c) one or more nucleases described herein. In some embodiments, the kit further comprises a plurality of primer pairs, wherein each primer pair is capable of identifying a barcode sequence associated with each exogenous donor nucleic acid.

These and other embodiments along with many of its advantages and features are described in more detail in conjunction with the text below and attached figures.

5. BRIEF DESCRIPTION OF THE FIGURES

FIG. 1A illustrates an exemplary embodiment of an exogenous landing pad with an upstream landing pad sequence (ULP) noted as "UL", a downstream landing pad sequence (DLP) as "DL", and a nuclease target sequence (NTS) noted as "X", positioned in the intergenic region of the ALG1 locus ("iALG1"). The (ULP) and the (DLP) of the exogenous landing pad used for homologous recombination with exogenous donor nucleic acids (ES) are shown as boxes with dots throughout all the figures.

FIG. 1B illustrates a library of three exogenous donor nucleic acids with an upstream library sequence (UL) noted as "UL" and a downstream library sequence (DL) noted as "DL" where UL and DL of each exogenous donor nucleic acid are capable of homologously recombining with (ULP) and (DLP) of the exogenous landing pad, respectively. Each of the three exogenous donor nucleic acid comprises an open reading frame and a terminator operably linked to a promoter (shown as an arrow) via a linker sequence ("A"), as a nucleic acid of interest. The nucleic acid of interest is positioned between (UL) and (DL) in each exogenous donor nucleic acid.

FIG. 1C illustrates an exemplary embodiment of markerless genomic integration of an exogenous donor nucleic acid. The exogenous landing pad is cleaved at (NTS) noted as "X" by a site-specific nuclease (shown as a pair of scissors).

FIG. 1D illustrates another embodiment of an exogenous landing pad wherein the exogenous landing pad further comprises an insulator sequence (e.g., transcription terminator) adjacent to the 5' end of the (ULP) noted as "UL" and another insulator sequence adjacent to the 3' end of the (DLP) noted as "DL" in FIG. 1D. The insulator sequences integrated in the landing pad can prevent or reduce unintended "read-through" transcription from another promoter located outside of the exogenous landing pad in the host cell's genome.

FIG. 1E illustrates three different types of exogenous donor nucleic acids which can be integrated into a landing pad. The top of FIG. 1E illustrates an exogenous donor nucleic acid which is made of a single DNA part. The middle of FIG. 1E illustrates two separate component polynucleotides which can be assembled in vivo to integrate into a landing pad. The bottom of FIG. 1E illustrates three separate component polynucleotides which can be assembled in vivo to integrate into a landing pad.

FIG. 1F illustrates a library of promoters as first component polynucleotides, a library of open reading frames as intermediate component polynucleotides, and a library of terminator sequences as last component polynucleotides, which can be combinatorially combined to integrate into a landing pad with compatible landing pad homology sequences.

FIG. 2A illustrates an exemplary embodiment of three standardized exogenous landing pads inserted in the host cell's genome. The standardized exogenous landing pads comprise the same upstream landing pad homology sequences (ULP, shown as "UL") and the same downstream landing pad homology sequences (DLP, shown as "DL") integrated at intergenic regions of the ALG1 locus, MGA1 locus, and YCT1 locus in the host cell's genome.

FIGS. 2B to 2D illustrate different libraries of exogenous donor nucleic acids in various DNA "stitch" designs. Each exogenous donor nucleic acids comprises at least one standardized homology sequence (UL, DL or both UL and DL) for homologously recombining into the standardized exogenous landing pads.

FIG. 2B illustrates an exemplary embodiment of a library of exogenous donor nucleic acids, each of which comprises a single open reading frame (ORF) operably linked to a promoter (i.e., in a "locked promoter" design), positioned between an upstream library sequence (UL) and a downstream library sequence (DL).

FIG. 2C illustrates an exemplary embodiment of libraries of exogenous donor nucleic acids which are component polynucleotides. When two component polynucleotides with compatible linker sequences are assembled in vivo via homologous recombination in the host cell, they generate various multi-open reading frames in a locked promoter design. The compatible linker sequences are shown as "SNAP" in FIG. 2C.

FIG. 2D illustrates another exemplary embodiment of libraries of exogenous donor nucleic acids which are component polynucleotides. When component polynucleotides are assembled in vivo via homologous recombination, they generate different combinations of a single ORF operably linked to a promoter. Because a promoter is split from an ORF in separate component polynucleotides, this DNA stitch design is referred to as a "split promoter" design.

FIGS. 3A to 3B illustrate exemplary exogenous donor nucleic acids (which are component polynucleotides) comprising additional functional elements—a barcode sequence and a nuclease target sequence which is different from the nuclease target sequence (NTS) present in the exogenous landing pads. The first component polynucleotide shown in FIG. 3A comprises "Y-cutter" nuclease target sequence. The last component polynucleotide shown in FIG. 3B comprises "Z-cutter" nuclease target sequence.

FIG. 3C illustrates three standardized exogenous landing pads engineered into the host cell's genome.

FIG. 3D illustrates different combinations of barcoded component polynucleotides integrated at the standardized exogenous landing pads shown in FIG. 3C. FIG. 3D also illustrates positions of a pair of standard oligonucleotide primers (shown by arrows), which is designed to anneal to primer binding segments around the barcode sequences integrated in the host cell's genome.

Figure 4:
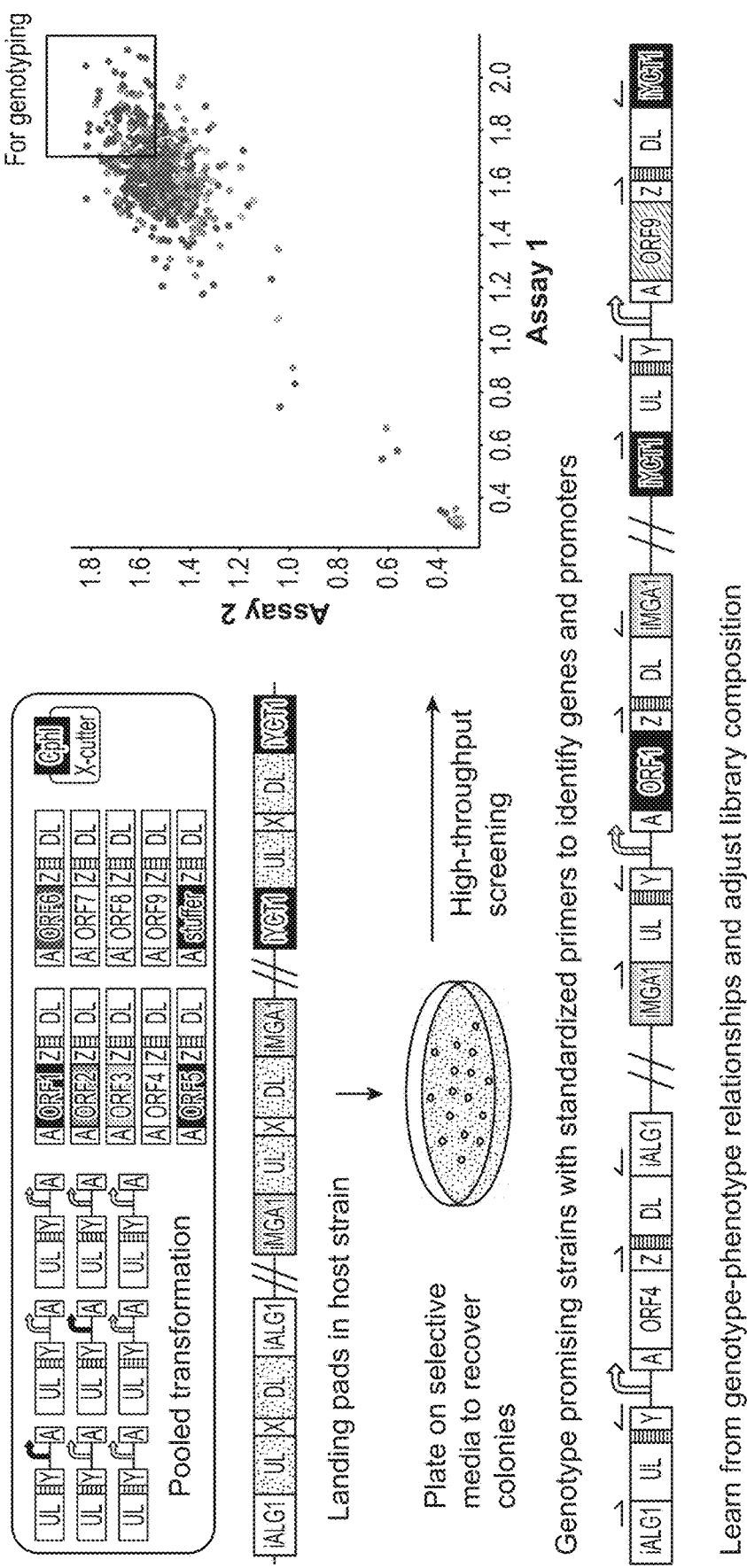

FIG. 4 illustrates an exemplary workflow for genomic integration of combinatorial libraries of first component polynucleotides and last component polynucleotides together with a plasmid encoding a nuclease, an X-cutter (i.e., CphI). The exemplary workflow further illustrates selecting colonies, high-throughput screening assays, and determining genotype of promising strains with standard primers to identify genes and promoters integrated into the standardized landing pads. From the genotype-phenotype relationships determined from the high-throughput integration and screening assays, the library composition can be adjusted to further improve the phenotypes of the host cell.

FIGS. 5A and 5B illustrate an exemplary embodiment of a host cell's genome comprising three standardized exogenous landing pads (with UL and DL landing pad homology sequences) and an addressable landing pad (with UL and $DL_1$ landing pad homology sequences) at $locus_1$ which can be used for targeted integration of last component polynucleotide comprising $DL_1$ as a downstream library sequence.

Figure 6A:
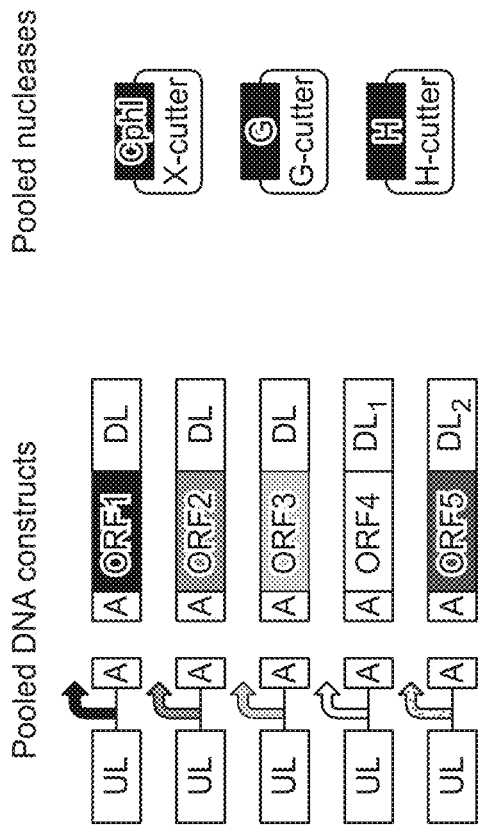
Figure 6B:
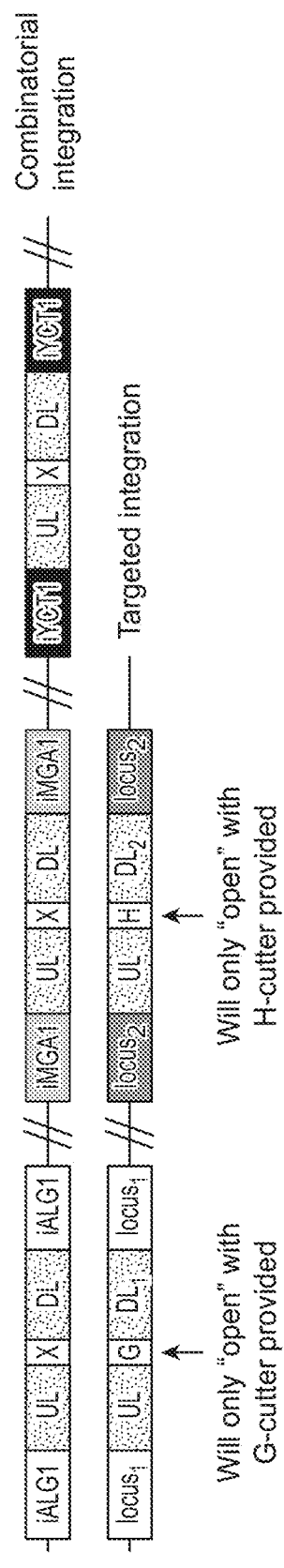

FIGS. 6A and 6B illustrate an exemplary embodiment of increasing flexibility of standardized exogenous landing pads (at intergenic regions of ALG1 locus, MGA1 locus, and YCT1 locus) by further incorporating addressable and optional landing pads. The exogenous landing pads are $locus_1$ and $locus_2$ comprise different downstream landing pad homology sequences ($DL_1$ and $DL_2$, respectively) compared to the downstream landing pad homology sequence (DL) of the standardized exogenous landing pads. These exogenous landing pads at these loci are addressable, because only a specific subset of exogenous donor nucleic acids with compatible library sequences ($DL_1$ and $DL_2$) can be integrated. These addressable exogenous landing pads are also optional, because they comprise nuclease target sequences "G" and "H", which are not cleaved when X-cutter is provided for cleaving the three standardized landing pads. They are cleaved only when G-cutter and H-cutter are provided, respectively. FIG. 6A illustrates pooled DNA constructs (i.e., component polynucleotides) and pooled nucleases which can be co-transformed into the host cell to allow simultaneous, combinatorial integration of DNA constructs into all five landing pads shown in FIG. 6B.

FIG. 7A illustrates an exemplary promoter swap landing pad building construct, which can be used to incorporate a promoter swap landing pad at a 5' end of an open reading frame at a native locus in the host cell's genome. The promoter swap landing pad integrated in the host cell's genome is shown in FIG. 7B. The homology sequences (UL and A) in the promoter swap landing pad to be used for homologous recombination of exogenous donor nucleic acids are shown in areas with dots in FIG. 7B. FIG. 7C further illustrates transformation of a parent strain with a promoter swap landing pad with a combinatorial library of promoters and a nuclease. FIG. 7D illustrates that, after transformation, colonies can be picked, screened for desired phenotypes, and genotyped to determine which promoter from the promoter library contributed to the desired phenotypes in the host cell.

FIG. 7E illustrates an exemplary terminator swap landing pad building construct, which can be used to integrate a terminator swap landing pad at a 3' end of an open reading frame at a native locus in the host cell's genome. The terminator swap landing pad integrated in the host cell's genome is shown in FIG. 7F. FIGS. 7G and 7H illustrate transformation of the parent strain comprising the terminator swap landing pad with either a degron library or a terminator library.

Figure 8:
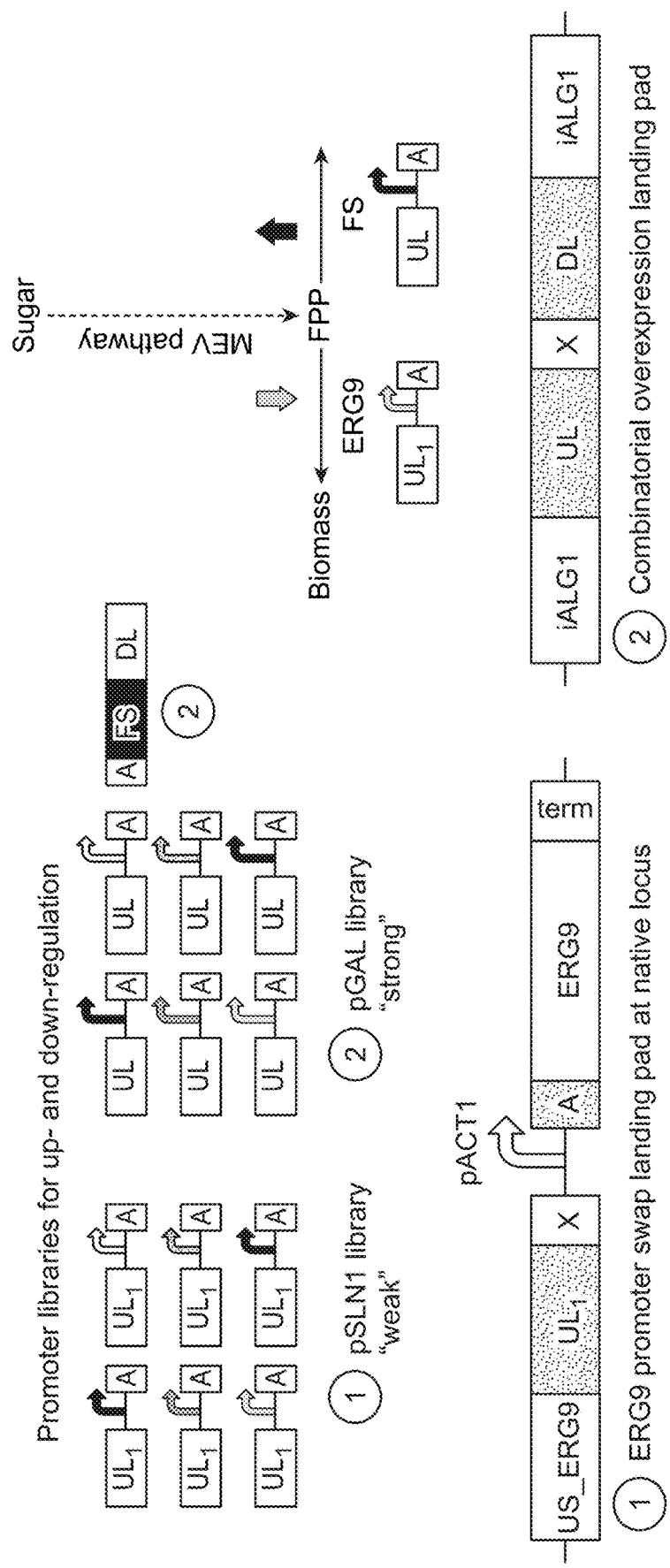

FIG. 8 illustrates an exemplary embodiment where a promoter swap landing pad (1) is used in combination with a exogenous standardized landing pad (2) to simultaneously integrate component polynucleotides into these landing pads and titrate two separate gene expression.

Figure 9:
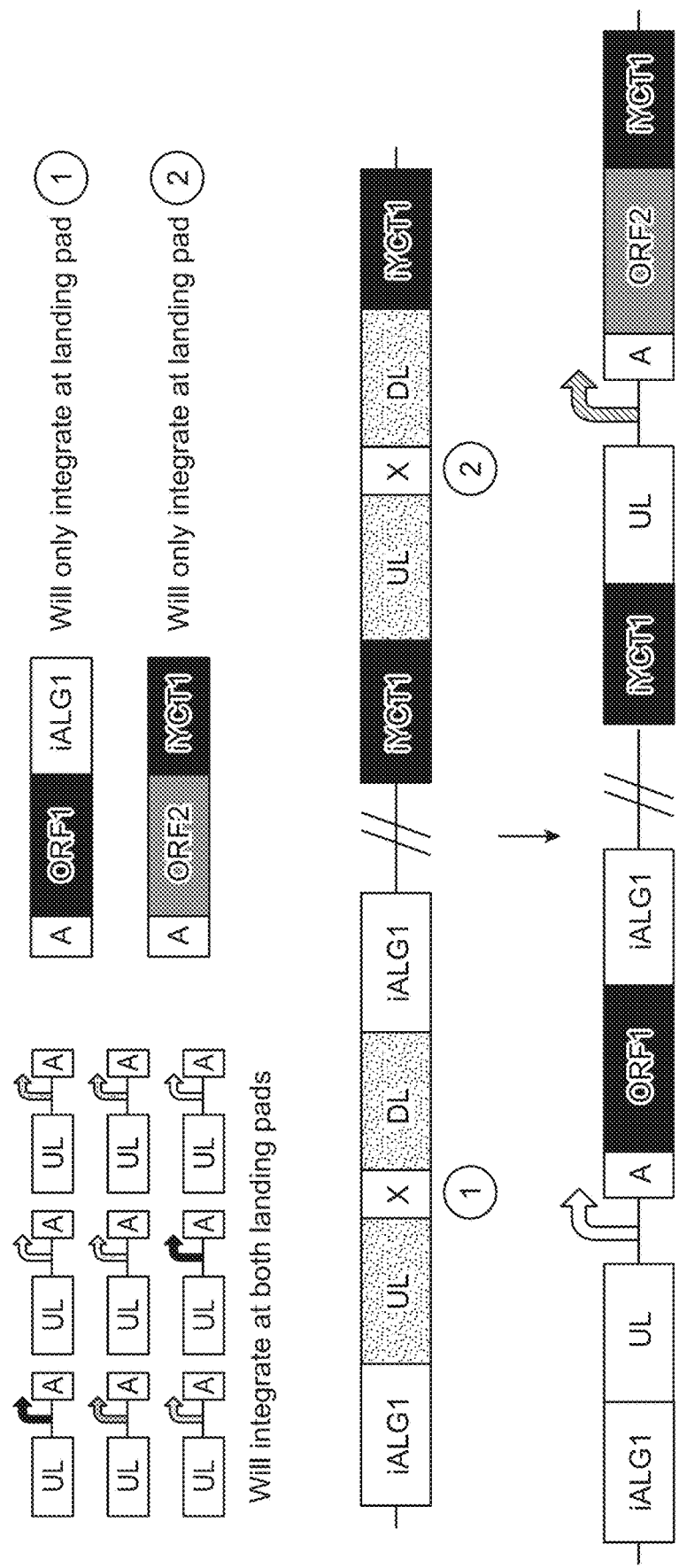

FIG. 9 illustrates an exemplary embodiment where expression of two open reading frames (ORF1 and ORF2) is balanced with targeted integration using a promoter library. In FIG. 9, the last component polynucleotide comprising ORF1 will only integrate at landing pad 1 at ALG1 locus, and the last component polynucleotide comprising ORF2 will only integrate at landing pad 2 at iYCT1 locus.

FIG. 10A illustrates a single ORF transformation components. The single ORF transformation consisted of equimolar concentrations of 4 constructs flanked by UL/DL homology: pGAL1>GFP, pGAL1>RFP, pGAL>RFP, and a promoterless, non-fluorescent "spacer" construct.

FIG. 10B illustrates split ORF transformation components. The split transformation consisted of equimolar concentrations of 9 split promoters and 4 promoterless ORFs containing "A" linker homology to facilitate recombination at each integration site. The promoters were chosen to span a range of predicted expression levels from 1% of pGAL1 to 75% of pGAL1.

FIG. 10C illustrates a histogram showing the frequency (number of wells) of specific GFP measurements in the single ORF transformation (A) vs. the split transformation (B).

FIG. 11 illustrates integration efficiencies of parent strains comprising different landing pad homology sequences.

Figure 12:
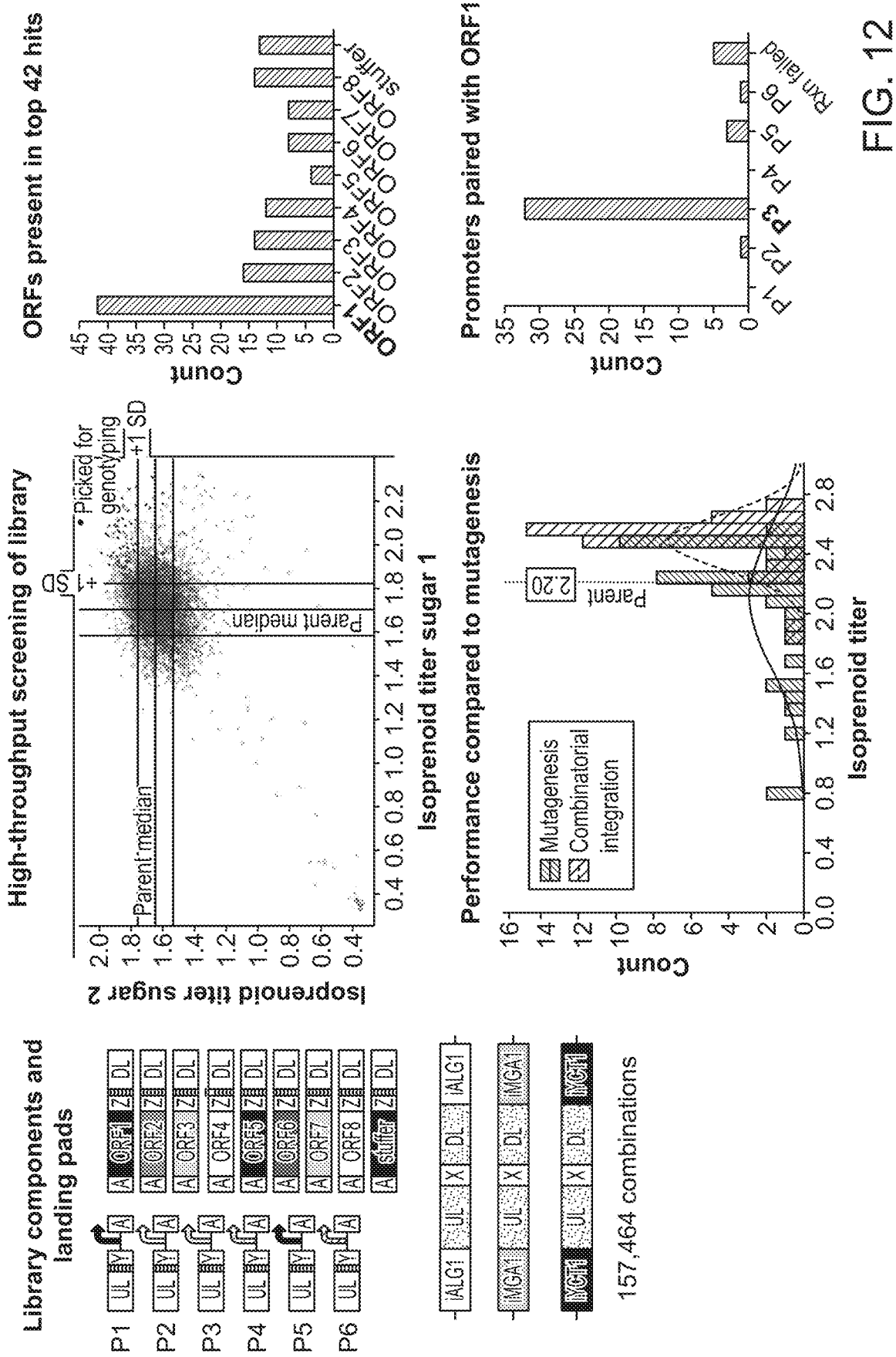

FIG. 12 illustrates library components and landing pads, high-throughput screening of the library, and performance of combinatorial library components integrated in the landing pads compared to mutagenesis.

FIG. 13 illustrates a schematic representation of the mevalonate (MEV) pathway for the production of isopentenyl pyrophosphate (IPP), and the conversion of IPP and dimethylallyl pyrophosphate (DMAPP) to geranyl pyrophosphate (GPP), farnesyl pyrophosphate (FPP), and geranylgeranyl pyrophosphate (GGPP), and the synthesis of various isoprenoids.

6. DETAILED DESCRIPTION OF THE EMBODIMENTS

6.1 Definitions

As used herein, the term "landing pad" refers to a recombination target site engineered into a host cell's genome to further facilitate insertion of an exogenous donor nucleic acid. In certain embodiments, a landing pad comprises a nuclease target sequence (NTS) which is positioned between landing pad homology sequences used for homologous recombination of an exogenous donor nucleic acids. The nuclease target sequence (NTS) is recognized by a site-specific nuclease, and the nuclease binds to (NTS) and cleaves a site within the exogenous landing pad. Those of skill will recognize that the nuclease may cleave within or outside the NTS.

The term "exogenous" landing pad refers to a landing pad which is not normally found in nature. In certain embodiments, an exogenous landing pad comprises landing pad homology sequences (e.g., an upstream landing pad homology sequence and a downstream landing pad homology sequence) that are not present in the host cell's genome prior to their insertion and/or its landing pad homology sequences are positioned outside of their natural locus (i.e., at a non-native locus) in the host cell's genome.

The term "heterologous" or "exogenous" refers to what is not normally found in nature. For example, the term "heterologous nucleotide sequence" or "exogenous nucleic acid" refers to a nucleotide sequence not normally found in a given cell in nature. As such, a heterologous nucleotide sequence or an exogenous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

The term "exogenous donor nucleic acid" refers to an exogenous nucleic acid which is being donated to integrate into the host cell's genome. In certain embodiments, an exogenous donor nucleic acid can be a single part DNA piece which has necessary homology sequences for integration into an exogenous landing pad. In other embodiments, an exogenous donor nucleic acid can be a component polynucleotide, which generally combine with other component polynucleotide, to integrate into an exogenous landing pad.

As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell, and is positioned at its natural locus in the host cell's genome.

As used herein, the term "contacting" refers to nucleic acids being placed in sufficiently close proximity, internally or externally, to the host cell to enable the nucleic acids to be taken up to be integrated into a host cell's genome.

As used herein, the term "library" refers to the collection of nucleic acids containing known common sequences or substantially common sequences at their 5' and 3' ends. In certain embodiments, exogenous donor nucleic acids in a library comprise an upstream library sequence at its 5' region and a downstream library sequence at its 3' region used for homologous recombination into exogenous landing pads in the host cell's genome. In certain embodiments, component polynucleotides in a library can comprise an upstream library sequence at their 5' region and a linker at their 3' region. In certain embodiments, component polynucleotides in a library can comprise a linker at their 5' region and a downstream library sequence at their 3' region. In certain embodiments, a library of component polynucleotides can comprise a linker at both 5' and 3' regions.

As used herein, the terms "cleaves," "cleavage" and/or "cleaving" with respect to a nuclease, e.g. a homing endonuclease, zinc-finger nuclease or TAL-effector nuclease, refer to the act of creating a double-stranded break (DSB) in a particular nucleic acid. The DSB can leave a blunt end or sticky end (i.e., 5' or 3' overhang), as understood by those of skill in the art.

As used herein, the term "engineered host cell" refers to a host cell that is generated by genetically modifying a parent cell using genetic engineering techniques (i.e., recombinant technology). The engineered host cell may comprise additions, deletions, and/or modifications of nucleotide sequences to the genome of the parent cell.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; *Higgins & Sharp, Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. Biosc.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

As used herein, the term "sequence identity" or "percent identity," in the context or two or more nucleic acid or protein sequences, refer to two or more sequences or subsequences that are the same or have a specified percentage of amino acid residues or nucleotides that are the same. For example, the sequence can have a percent identity of at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.,* 22: 4673-4680), ALIGN (Myers et al., (1988) *CABIOS,* 4: 11-17), FASTA (Pearson et al., (1988) *PNAS,* 85:2444-2448; Pearson (1990), *Methods Enzymol.,* 183: 63-98) and gapped BLAST (Altschul et al., (1997) *Nucleic Acids Res.,* 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=1, Nucleic mismatch=−3, Expectation value=10.0, Word size=11). For polypeptide sequence alignment and sequence identity calculations, BLASTP program is used with its default parameters (Gap opening=11, Gap extension penalty=2; Nucleic match=1; Nucleic mismatch=−3, Expectation value=10.0; Word size=11; matrix Blosum 62). Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

As used herein, the term "markerless" refers to integration of a donor DNA (e.g., an exogenous donor nucleic acid) into an exogenous landing pad within a host cell's genome without accompanying integration of a selectable marker. In some embodiments, the term also refers to the recovery of such a host cell without utilizing a selection scheme that relies on integration of selectable marker into the host cell's genome. For example, in certain embodiments, a selection marker that is episomal or extrachromosomal may be utilized to select for cells comprising a plasmid encoding a nuclease capable of cleaving a genomic target site. Such use would be considered "markerless" so long as the selectable marker is not integrated into the host cell's genome.

As used herein, the term "polynucleotide" refers to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the term "DNA segment," alternately referred to as "Bits" in the examples below, refers to any isolated or isolatable molecule of DNA. Useful examples include but are not limited to a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, degradation signal, a spacer sequence, or a barcode sequence, or any other naturally occurring or synthetic DNA molecule. In some embodiments, the DNA segment can be of natural origin. Alternatively, a DNA segment can be completely of synthetic origin, produced in vitro. Furthermore, a DNA segment can comprise any combination of isolated naturally occurring DNA molecules, or any combination of an isolated naturally occurring DNA molecule and a synthetic DNA molecule. For example, a DNA segment may comprise a heterologous promoter operably linked to a protein coding sequence, a protein coding sequence linked to a poly-A tail, a protein coding sequence linked in-frame with a epitope tag coding sequence, and the like.

"Primer" refers to a polynucleotide sequence that is capable of specifically hybridizing to a polynucleotide template sequence, e.g., a primer binding segment, and is capable of providing a point of initiation for synthesis of a complementary polynucleotide under conditions suitable for synthesis, i.e., in the presence of nucleotides and an agent that catalyzes the synthesis reaction (e.g., a DNA polymerase). The primer is complementary to the polynucleotide template sequence, but it need not be an exact complement of the polynucleotide template sequence. For example, a primer can be at least about 80, 85, 90, 95, 96, 97, 98, or 99% identical to the complement of the polynucleotide template sequence. A primer can be of variable length but generally is at least 15 bases. In some embodiments, the primer is between 15 and 35 bases long. In some embodiments, the primer is more than 35 bases long. In other embodiments, the primer has a melting temperature ($T_m$), i.e., the temperature at which one half of the DNA duplex will dissociate to become single stranded, of at least 50° C. In other embodiments, the primer has a $T_m$ between about 50° C. and 70° C. In still other embodiments, the primer does not form appreciable DNA or RNA secondary structures so as to not impact the efficiency of hybridization to the polynucleotide template sequence.

As used herein, the term "primer binding segment" is a polynucleotide sequence that binds to a primer so as to provide a point of initiation for synthesis of a complementary polynucleotide under conditions suitable for synthesis.

As used herein, the term "linker sequence" refers to a polynucleotide sequence in a component polynucleotide, which is capable of homologously recombining with a linker sequence in another component polynucleotide via homologous recombination in vivo. In certain embodiments, a linker sequence of a component polynucleotide is capable of homologously recombining with a landing pad linker sequence of an exogenous landing pad.

As used herein, the term "simultaneous," when used with respect to multiple integration, encompasses a period of time beginning at the point at which a host cell is co-transformed with a nuclease, e.g. a plasmid encoding a nuclease, and more than one donor DNA to be integrated into the host cell's genome, and ending at the point at which the transformed host cell, or clonal populations thereof, is screened for successful integration of the donor DNAs at landing pads. In some embodiments, the period of time encompassed by "simultaneous" is at least the amount of time required for the nuclease to bind and cleave its target sequence within the host cell's chromosome(s). In some embodiments, the period of time encompassed by "simultaneous" is at least 6, 12, 24, 36, 48, 60, 72, 96 or more than 96 hours, beginning at the point at which the a host cell is co-transformed with a nuclease, e.g. a plasmid encoding a nuclease, and more than one donor DNA.

The term "degron sequence" refers to a nucleic acid that encodes a protein that confers instability to another protein fused in frame to the degron protein by changing the degradation rate of the fused protein.

The term "terminator" refers to a transcription terminator sequence which defines the end of a transcriptional unit (such as a gene) and initiate the process of releasing the newly synthesized RNA from the transcription machinery.

The term "insulator sequence" refers to a nucleotide sequence inserted in an exogenous landing pad, and it insulates the landing pad from unintended "read-through" transcription from another promoter located upstream to the landing pad in the host cell's genome. An example of an insulator sequence is a transcription terminator or a nucleic acid forming a structure that sterically hinder an unintended read through transcription from an upstream promoter.

The term "neutral loci" refers to locations in a host cell's genome with no known function or gene transcription or at which integration of an exogenous landing pad and/or integration of an exogenous donor nucleic acid therein does not significantly affect cell viability or function compared to a control cell. The term "neutral loci" in the context of multiple exogenous landing pads can refer to genomic loci at which the integration of the same DNA construct encoding a protein results in the level of protein expression being similar.

The term "intergenic region" refers to a stretch of DNA sequences located between genes with no known function and is a subset of noncoding DNA.

6.2 Generating Host Cells with Exogenous Landing Pad(s) in Host Cell's Genome Provided herein are host cells modified to comprise one or more exogenous landing pads integrated in the host cell's genome and methods of generating such host cells. As used herein, an exogenous landing pad refers to a recombinantly generated target site that is stably integrated into the host cell's genome to further facilitate the insertion of an exogenous donor nucleic acid of interest via homologous recombination. An exogenous landing pad comprises landing pad homology regions at its 5' and 3' ends to facilitate homologous recombination of an exogenous donor nucleic acid comprising compatible homology sequence. In certain embodiments, the landing pad's homology regions at its 5' and 3' ends (also referred to as landing pad homology sequences) are exogenous to and are not represented in the host cell's genome, and the integration of exogenous donor nucleic acids does not rely any endogenous genomic sequences for homologous recombination in the host cell. As such, in certain embodiments, an integration event of an exogenous donor nucleic acid at the landing pad is independent of endogenous genomic sequences around at which the exogenous landing pad is located.

In certain embodiments, a landing pad further comprises a nuclease target sequence (NTS) recognizable and cleavable by a site-specific nuclease, which is capable of generating a DNA double strand break (DSB) within the landing pad. The DSB within the landing pad increases integration efficiencies of exogenous donor nucleic acids and enrichment of transformed host cells that are able to repair the DSBs. In particular embodiments, a landing pad integrated in a host cell's genome comprises an upstream landing pad homology sequence (ULP), a downstream landing pad homology sequence (DLP), and a nuclease target sequence (NTS) positioned between (ULP) and (DLP).

FIG. 1A illustrates an exemplary embodiment of a host cell comprising one landing pad integrated at an intergenic region downstream of ALG1 locus in a host cell. In this embodiment, the upstream landing pad homologous sequence (ULP) is noted as "UL", and the downstream landing pad homology sequence (DLP) is noted as "DL". The nuclease target sequence (NTS) is noted as "X". In certain embodiments, the landing pad is recombinantly engineered into a pre-determined locus, an intergenic region downstream of ALG1 locus in the host cell. In certain embodiments, at least one of the (ULP) and the (DLP) is a recombinantly generated synthetic sequence which does not exist in the host cell's genome. In certain embodiments, at least one of the (ULP) and the (DLP) can be a sequence that exists endogenously in the host cell's genome, but is located outside of their natural locus (i.e., at a non-native locus in a landing pad).

FIG. 1B illustrates a library of exogenous donor nucleic acids, each exogenous donor nucleic acid (ES) comprising a nucleic acid of interest (i.e., an open reading frame with a terminator sequence operably linked to a promoter shown as a curved arrow) positioned between an upstream library sequence (UL) and a downstream library sequence (DL). In the exemplary embodiment shown in FIG. 1B, each promoter is operably linked to an ORF via a linker sequence "A". However, the linker sequence A can be omitted in certain embodiments, and an exogenous donor nucleic acid can be engineered such that a promoter is directly operably linked to an open reading frame (ORF) without the linker sequence.

In the embodiment illustrated in FIG. 1A, the upstream landing pad homology sequence (ULP) of the landing pad comprises the same nucleotide sequence as (UL) of exogenous donor nucleic acids, and the downstream landing pad homology sequence (DLP) of the landing pad comprises the same nucleotide sequence as (DL) of exogenous donor nucleic acids. Therefore, (UL) of any exogenous donor nucleic acids in the library is capable of homologously recombining with (UL) of the landing pad, and (DL) of any exogenous donor nucleic acids in the library is capable of homologously recombining with (DL) of the landing pad shown in FIG. 1A. The nuclease target sequence in the landing pad is recognizable and cleavable by nuclease X-cutter (e.g., CphI, shown as a pair of scissors in FIG. 1A). As shown in FIG. 1C, once integrated in the landing pad, a nucleic acid of interest (e.g., ORF1 operably linked to a promoter) is flanked by exogenous landing pad homology sequences (i.e., UL and DL), which are nested within endogenous genomic sequences (e.g., iALG1) in the host cell's genome. However, in this embodiment, the endogenous genomic sequences are not used for homologous recombination.

FIG. 1D illustrates another embodiment of an exogenous landing pad. The exogenous landing pad integrated at the iALG1 locus is substantially similar to the landing pad shown in FIG. 1A, except that the landing pad further comprises an insulator sequence at the 5' region of the landing pad adjacent to the upstream landing pad sequence noted as "UL" and at the 3' region of the landing pad adjacent to the downstream landing pad sequence note as "DL". While FIG. 1D illustrates an insulator sequence present at both 5' and 3' regions of the landing pad, in certain embodiments, the landing pad has an insulator sequence at only at the 5' region, at the 3' region, or neither the 5' nor 3' regions of the landing pad. In certain embodiments, an insulator sequence is a transcription terminator sequence.

FIG. 1E illustrates three different types of exogenous donor nucleic acids which can be integrated into a landing pad. The top of FIG. 1E illustrates an exogenous donor nucleic acid which is made of a single DNA part. The exogenous donor nucleic acid comprises a nucleic acid of interest positioned between an upstream library sequence (UL) and a downstream library sequence (DL). The nucleic acid of interest is an open reading frame ("ORF") positioned between a promoter (shown as a curved arrow) and a terminator ("term"). The promoter and the ORF are linked via a linker sequence "A".

The middle of FIG. 1E illustrates exogenous donor nucleic acids as two separate component polynucleotides which can be assembled in vivo and integrate into a landing pad. The first component polynucleotide shown on the left has a promoter sequence as a nucleic acid of interest, and the last component polynucleotide shown on the right has an ORF as a nucleic acid of interest. When the component polynucleotide on the left and the component polynucleotide on the right are assembled in vivo via a matching linker sequence "A", they are capable of integrating into the landing pad shown in FIG. 1D.

The bottom of FIG. 1E illustrates exogenous donor nucleic acids three separate component polynucleotides which can be assembled in vivo and integrate into a landing pad as assembled parts. The first component polynucleotide shown on the left has a promoter sequence as a nucleic acid of interest, the intermediate component polynucleotide shown in the middle has an ORF as a nucleic acid of interest, and the last component polynucleotide shown on the right has a terminator as a nucleic acid of interest. Each of the first component polynucleotide and the intermediate component polynucleotide comprises a matching linker sequence "A"; and each of the intermediate component polynucleotide and the last component polynucleotide comprises a matching linker sequence "B". When the component polynucleotides are assembled in vivo via their respective matching linker sequences "A" and "B", they are capable of integrating into the landing pad shown in FIG. 1D.

While FIG. 1E illustrates using a single part exogenous donor nucleic acid, two part component polynucleotides, or three part component polynucleotides to integrate nucleic acids into a landing pad, the number of component polynucleotides that can be utilized for integration into a landing pad can be more than 3. The use of component polynucleotides for genomic integration is further described in Section 5.3.3 below.

FIG. 1F illustrates three part component polynucleotides which can be combinatorially combined and integrated into the landing pad shown in FIG. 1D. In FIG. 1F, shown on the left is a promoter library of first component polynucleotides, each of which comprising a different promoter sequence positioned between an upstream library sequence (UL) and a first linker sequence (A). Shown in the middle of FIG. 1F is an ORF library of intermediate component polynucleotides, each of which comprising a different ORF positioned between an upstream intermediate linker sequence "A" and a downstream intermediate linker sequence "B". Shown on the right of FIG. 1F is a terminator library of last component polynucleotides, each of which comprising a different terminator positioned between a last linker sequence "B" and a downstream library sequence (DL). Each component polynucleotide from each library can combinatorially combine with other component polynucleotides in other libraries. Therefore, nine component polynucleotides shown in FIG. 1F can be combinatorially combined to generate 27 different combinations of component polynucleotides integrated a single landing pad, which can potentially generate a population of host cells with 27 different phenotypes.

In particular embodiments, a host cell comprises two or more exogenous landing pads integrated in the host cell's genome. In certain embodiments, the two or more exogenous landing pads are standardized in that their upstream landing pad homology sequences (ULP) are identical or substantially identical to one another, and their downstream landing pad homology sequences (DLP) are identical or substantially identical to one another. The standardized landing pad homology sequences facilitate host cell-mediated homologous recombination of any exogenous donor nucleic acids into any landing pads, as long as the exogenous donor nucleic acids comprise compatible homology regions at their 5' and 3' regions. Thus, in certain embodiments, all exogenous donor nucleic acids in a library comprise a standardized upstream library sequence (UL) at their 5' end, which can homologously recombine with any (ULP) in any of the landing pads and a standardized downstream library sequence (DL) at their 3' end, which can homologously recombine with any (DLP) in any of the landing pads.

In certain embodiments, the landing pads are integrated into genomic loci that are pre-determined to be "neutral" loci of the host cell's genome. In certain embodiments, a genomic locus for landing pad integration is considered as a neutral locus if no gene transcript is found in the region around the genomic locus by RNA sequencing. In certain embodiments, a genomic locus for landing pad integration is considered as a neutral locus if no gene transcription is found in the region around the genomic locus by RNA sequence, and if the genomic locus does not comprise a sequence that is homologous to a similarly positioned genomic locus in other closely related species (e.g., Saccharomyces cerevisiae and Saccharomyces paradoxus) when their genomic sequences are aligned. The genomic sequences of closely related species can be compared using any suitable methods, for example, visually or using an algorithm such as BLASTn, UCSC Genome Browser from genome.ucsc.edu, and the like. In some embodiments, one or more landing pads are integrated at intergenic regions in the host cell's genome with no known function. In some embodiments, one or more landing pads are integrated at non-coding regions of the host cell's genome. In some embodiments, one or more landing pads are integrated at or adjacent to the coding regions of the host cell's genome.

In some embodiments, these genomic loci determined to be neutral by sequence analysis are further validated based on the host cell function. For example, the effects of landing pad integration on parameters, such as the target molecule production, biomass yield, cell growth rate, and the like, can be measured and compared to a control host cell without integration of landing pads. In some embodiments, expression of a reporter gene integrated in one landing pad can be compared to those integrated in other landing pads in the host cell's genome to determine any variability in integration efficiencies or expression of the reporter gene in different landing pads.

The term "neutral loci" in the context of multiple exogenous landing pads can refer to genomic loci at which the integration of the same DNA construct encoding a protein results in the level of protein expression being similar. For example, the expression levels of a reporter gene integrated at multiple exogenous landing pads can vary less than 50%, less than 40%, less than 30%, less than 20%, less than 10%, or less than 5%, if the exogenous landing pads are integrated at neutral loci. Therefore, in certain embodiments, the integration of exogenous landing pads at neutral loci removes any genomic location context for expression of an exogenous nucleic acid integrated at the exogenous landing pads.

FIG. 2A illustrates an exemplary embodiment of a host cell comprising three standardized, exogenous landing pads integrated in the host cell's genome. In the exemplary embodiment shown in FIG. 2A, the three standardized landing pads are integrated in the intergenic regions downstream of loci ALG1, MGA1, and YCT1 in the yeast cell genome (i.e., iALG1, iMGA1, and iYCT1, respectively). These intergenic genomic loci have been validated as neutral loci. In the embodiment illustrated in FIG. 2A, each landing pad comprises a nuclease target sequence (NTS), recognizable and cleavable by the nuclease "X-cutter" (e.g., CphI), which is positioned between an upstream landing pad homology sequence (ULP) and a downstream landing pad homology sequence (DLP) of the landing pads. In FIG. 2A, the (ULP) of the three landing pads comprise the same sequence as the upstream library sequence (UL) of libraries of exogenous donor nucleic acids; and the (DLP) of the three landing pads comprise the same sequence as the downstream library sequence (DL) of libraries of exogenous donor nucleic acids. In the embodiment illustrated in FIGS. 2A to 2D, since each of the three landing pads comprises the same nuclease target sequence cleavable by the nuclease X-cutter (e.g., CphI), these landing pads can accommodate simultaneous integration of multiple exogenous donor nucleic acids with the use of only a single nuclease that specifically recognizes the nuclease target sequence and cleaves a site within the landing pad.

Any suitable number of landing pads may be integrated into the host cell's genome. In certain embodiments, the number of landing pads integrated into the host cell's genome is between 1 and 500. In certain embodiments, the number of landing pads integrated in the host cell's genome is between 2 and 250. In certain embodiments, the number of landing pads integrated in the host cell's genome is between 3 and 200. In certain embodiments, the number of landing pads integrated in the host cell's genome is between 3 and 50. In certain embodiments, the number of landing pads integrated in the host cell's genome is between 3 and 20. In certain embodiments, the number of landing pads integrated in the host cell's genome is between 3 and 10. In certain embodiments, the number of landing pads integrated in the host cell's genome is 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, or any number between these numbers.

While FIG. 2A illustrates three landing pads in three separate genomic loci, in some embodiments, two or more landing pads can be integrated in a single genomic locus. For example, two landing pads in tandem can be integrated at the intergenic region downstream from the ALG1 locus. In such embodiments, an essential gene may be inserted between the two landing pads to add a selective pressure for host cells that retain the landing pads instead of looping them out through homologous recombination. Alternatively, one can select loci with chromosomal positions that are incompatible with chromosomal translocation, such that a recombination event results in a non-viable cell.

Each landing pad sequence can be generated using any techniques known in the art. In some embodiments, the entire landing pad sequence can be synthesized de novo using chemical synthesis and/or recombinant molecular biology techniques. See, e.g., Kosuri & Church, *Nature Methods* 11: 499-507 (2014). In certain embodiments, parts of each landing pad (e.g., ULP, DLP, and NTS) can be separately synthesized as separate parts and then ligated together. Alternatively, a landing pad sequence can be obtained from commercial nucleic acid synthesis services. These include, for example, Twist Bioscience (San Francisco, CA), Biomatik (Wilmington, DE), Genescript (Piscataway, NJ), and GeneArt gene synthesis services available through www.introgen.com.

The landing pads can be integrated into the host cell's genome using any suitable methods known in the art. For example, traditional gene targeting method by homologous recombination using a selectable marker may be used to introduce and integrate a landing pad into the host cell's genome. In some embodiments, the selectable marker gene may be subsequently excised from the host cell's genome. See, e.g., U.S. Pat. Nos. 7,919,605, and 9,018,364. In some embodiments, designer nucleases, such as CRISPR-Cas system, can be used to facilitate integration of one or more landing pads into desired specific target genomic loci. See, e.g., U.S. Patent Application Publication No. 2015/0184199; Horwitz et al., *Cell Systems* 1, 88-96, Jul. 29, 2015; Cong et al., 2013, *Science* 339: 819-823; Jao et al., 2013, *Proc. Natl. Acad. Sci USA* 110, 13904-13909; Wang et al. 2013, Cell 153, 910-918; Jacobs et al; 2014, *Nat. Commun.* 5, 5344.

6.2.1. Upstream and Downstream Landing Pad Homology Sequences

In certain embodiments, each of exogenous landing pads engineered into the host cell's genome comprises an upstream landing pad homology sequence (ULP) at its 5' region and a downstream landing pad homology sequence (DLP) at its 3' region. These sequences provide regions of homology for host cell-mediated recombination and integration of exogenous donor nucleic acids. In particular embodiments, the landing pad homology sequences are "exogenous" to the genomic loci at which they are integrated. In other word, these landing pad homology sequences are not part of endogenous sequences of the genomic loci at which they are integrated. In other embodiments, landing pad homologous sequences may exist in the host cell's genome, but they are located at their non-native locus in the landing pad.

In certain embodiments, the landing pad homology sequences do not share sequence homology with any genomic DNA. In certain embodiments, the nucleotide sequences of (ULP) and/or (DLP) are synthetic. In certain embodiments, the nucleotide sequences of (ULP) and/or (DLP) are randomly generated by a computer algorithm. Suitable landing pad homology sequences are selected by removing randomly generated sequences with undesirable features, such as sequences with tandem and/or inverted repeats, DNA secondary structure, and any significant homology to known biological sequences in the host cell's genome. In certain embodiments, the randomly generated nucleotides are further filtered to select those which comprise between about 30% to about 70%, typically about 40% to 60%, typically between about 45% to about 55%, or about 50% GC content (or guanine-cytosine content).

In some embodiments, (ULP) and (DLP) can comprise any nucleotide sequence of sufficient length and sequence identity that allows for genomic integration of the exogenous nucleic acid (ES), at any landing pads. In certain embodiments, each of (ULP) and (DLP), independently consists of about 20 to 5,000 nucleotides. In certain embodiments, each of (ULP) and (DLP) independently consists of about 20 to 2,500 nucleotides. In certain embodiments, each of (ULP) and (DLP) independently consists of about 25 to 1,000 nucleotides. In certain embodiments, each of (ULP) and (DLP) independently consists of about 50 to 500 nucleotides. In certain embodiments, each of (ULP) and (DLP) independently consists of about 100 to about 500 nucleotides. In certain embodiments, each of (ULP) and (DLP), independently consists of about 20, 25, 50, 75, 100, 150, 200, 250, 300, 350, 400, 450, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000 nucleotides, or any numbers in between these numbers. In some embodiments, each of (ULP) and (DLP) independently consists of about 500 nucleotides. In some embodiments, each of (ULP) and (DLP) independently consists of about 200 nucleotides. In some embodiments, each of (ULP) and (DLP) independently consists of about 100 nucleotides.

In certain embodiments where there are two or more landing pads integrated in the host cell's genome, the nucleotide sequences of all (ULP) in the landing pads are substantially identical to one another, and the nucleotide sequences in all (DLP) in the landing pads are substantially identical to one another. For example, all (ULP) in the landing pads comprise nucleotide sequences that are at least 70%, 75%, 80%, 85%, 90%, 95%, 96%, 97%, 98%, 99%, or 100% identical to one another; and all (DLP) in the landing pads comprise nucleotide sequences that are at least 70%, 75%, 80%, 85%, 90%, 95%, 96%, 97%, 98%, 99%, or 100% identical to one another. In some embodiments, the nucleotide sequences of all (ULP) in the landing pads are identical to one another, and the nucleotide sequences in all (DLP) in the landing pads are identical to one another. Such an exemplary embodiment is illustrated in FIG. 2A where three landing pads comprise three identical (ULP)s noted as "UL" and three identical (DLP)s noted as "DL." When the two or more landing pads integrated in the host cell's genome comprise substantially identical (ULP)s and (DLP)s, these landing pads are referred to as standardized or primary landing pads.

In certain embodiments, the host cell's genome can comprise one or more alternative landing pads which are different from the primary landing pads. Exemplary embodiments of these alternative landing pads are illustrated in FIGS. 5B, 6B, 7A-7C, and 8, which are further described in detail in sections below. These alternative landing pads can be incorporated in addition or in alternative to the primary landing pads.

6.2.2. Nuclease Target Sequence

The nuclease target sequence (NTS) in each landing pad comprises a nucleotide sequence that is recognized by a nuclease. When a nuclease recognizes and binds to the nuclease target sequence (NTS) in each landing pad, it can cleave a site within or nearby (NTS) in the landing pad. In certain embodiments, the nuclease target sequence is located adjacent to at least one of the landing pad sequences. In certain embodiments, the nuclease target sequence (NTS) is positioned between an upstream landing pad homology sequence (ULP) and a downstream landing pad homology sequence (DLP). When a nuclease is introduced to the host cell comprising landing pads with a nuclease target sequence, the nuclease is capable of causing a double-strand break at a site within the landing pads, which greatly increases the frequency of homologous recombination at or near the cleavage site.

In some embodiments, multiple landing pads comprise the same nuclease target sequence, thereby facilitating simultaneous multiple integration events with the use of only a single nuclease that specifically recognizes the nuclease target sequence. In some embodiments, some of multiple landing pads in the host cell's genome can have different nuclease target sequences which are recognizable and cleavable by different nucleases. In such embodiments, different nucleases may be used simultaneously or sequentially to cleave different nuclease target sequences for simultaneous or sequential integration of exogenous donor nucleic acids in the host cell's genome.

In some embodiments, the nuclease target sequence in a landing pad comprises a nuclease target sequence that is not otherwise represented in the native genome of the host cell. In some embodiments, the nuclease target sequence which is recognized by the nuclease is present in the host cell's genome only within the landing pads, thereby minimizing any off-target genomic binding and cleavage by the nuclease. In certain embodiments, a specific nuclease may be a rare-cutting endonuclease that has a polynucleotide recognition site of at least 12 base pairs in length, or in some instances, from 14 to 55 base pairs in length. Such endonucleases can either be derived from natural proteins having endonuclease activity, such as homing endonucleases (WO 2004/067736), or by fusion of various nucleic acid binding polypeptides to nuclease components, such as Fok-1 or Tev-1 catalytic domains (WO2012138927). Appropriate nucleic acid binding domains that can be engineered in this respect are, for instance, Zinc Finger domains (Kim et al., 1994, Chimeric restriction endonuclease, PNAS, 91:883-887), TAL effectors originating from microbes related to *Xanthomonas* (WO 2011/072246) or MBBBD (Modular base-per-base binding domains) originating from the endosymbiotic *Burkholderia rhizoxinica*. In addition, a system involving nuclease Cas9 homologues and RNaseIII (CRISPR/Cas9) has been developed from the immune system of bacterial microorganisms. In this system, the specificity of the endonuclease protein complex is addressed by specific single stranded RNAs called "guide-RNA" (gRNA). This guide-RNA has the ability to hybridize the nucleic acid target sequence to be cleaved by the nuclease component Cas9 (Le Cong et al., 2013, *Science,* 339 (6121): 819-823). Nuclease target sequences that are recognizable and/or cleavable by these nucleases are well-known and described in the art. The description of suitable nucleases and nuclease target sequences are further described in detail in Section 5.6 below.

6.2.3. Suitable Host Cells

Suitable host cells for generating a parent strain with landing pads include any cell in which integration of a nucleic acid or "donor DNA" of interest into a chromosomal or episomal locus is desired. In some embodiments, the cell is a cell of an organism having the ability to perform homologous recombination. Although several of the illustrative embodiments are demonstrated in yeast (*S. cerevisiae*), it is believed that the methods of genomic modification provided herein can be practiced on all biological organisms having a functional recombination system, even where the recombination system is not as proficient as in yeast. Other cells or cell types that have a functional homologous recombination systems include bacteria such as *Bacillus subtilis* and *E. coli* (which is RecE RecT recombination proficient; Muyrers et al., *EMBO rep.* 1: 239-243, 2000); protozoa (e.g., *Plasmodium, Toxoplasma*); other yeast (e.g., *SchizoSaccharomyces pombe*); filamentous fungi (e.g., *Ashbya gossypii*); plants, for instance the moss *Physcomitrella patens* (Schaefer and Zryd, *Plant J.* 11: 1195-1206, 1997); and animal cells, such as mammalian cells and chicken DT40 cells (Dieken et al., *Nat. Genet.* 12:174-182, 1996).

In some embodiments, the host cell is a prokaryotic cell. In some embodiments, the host cell is a eukaryotic cell. In some embodiments, the cell is a fungal cell (for instance, a yeast cell), a bacteria cell, a plant cell, or an animal cell (for instance, a chicken cell). In some embodiments, the host cell is a mammalian cell. In some embodiments, the host cell is a Chinese hamster ovary (CHO) cell, a COS-7 cell, a mouse fibroblast cell, a mouse embryonic carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In particular embodiments, the host cell is a yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces,*

*Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtznanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phafia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis,* and *Zygozyma*, among others.

In some embodiments, the yeast host cell is a *Saccharomyces cerevisiae* cell, a *Pichia pastoris* cell, a *SchizoSaccharomyces pombe* cell, a *Dekkera bruxellensis* cell, a *Kluyveromyces lactis* cell, a *Arxula adeninivorans* cell, or a *Hansenula polymorpha* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces lactis*) cell. In some embodiments, the yeast host cell is a cell belonging to the genus *Candida*, such as *Candida lipolytica, Candida guilliermondii, Candida krusei, Candida pseudotropicalis,* or *Candida utilis*. In another particular embodiment, the yeast host cell is a *Kluyveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

6.3 Exogenous Donor Nucleic Acids to be Integrated into Landing Pads

In another aspect, provided herein are exogenous donor nucleic acids comprising standardized homology sequences that are re-usable in any host cells with standardized landing pads engineered into their genome. In certain embodiments, exogenous donor nucleic acids introduced into a host cell comprise both upstream and downstream library sequences so that they can homologously recombine into the landing pads on their own. In certain embodiments, exogenous donor nucleic acids are component polynucleotides, each of which does not have both upstream and downstream library sequences for homologously recombining at the landing pads. When component polynucleotides with compatible linker sequences are assembled in vivo via homologous recombination, the assembled component polynucleotides with both upstream and downstream library sequences are capable of homologously recombining at the landing pads in the host cell's genome. In some embodiments, each component polynucleotide comprises a nucleic acid of interest positioned between an upstream library sequence (UL) and a linker sequence. In other embodiments, each component polynucleotide comprises a nucleic acid of interest positioned between a linker sequence and a downstream library sequence (DL). In certain embodiments, component polynucleotides comprise a nucleic acid of interest positioned between two linker sequences. When these different sets of component polynucleotides contact the host cell, their respective linker sequences can homologously recombine in vivo and integrate the assembled component polynucleotides into any one of the landing pads in the host cell's genome. In certain embodiments, exogenous donor nucleic acids are introduced into the host cell as linear DNA molecules. In certain embodiments, exogenous donor nucleic acids are introduced in to the host as circular DNA molecules.

The exogenous donor nucleic acids can be generated by any technique apparent to one skilled in the art. In certain embodiments, the integration polynucleotide is generated using polymerase chain reaction (PCR) and molecular cloning techniques well known in the art. See, e.g., *PCR Technology: Principles and Applications for DNA Amphlication*, ed. H A Erlich, Stockton Press, New York, N.Y. (1989); Sambrook et al., 2001, *Molecular Cloning—A Laboratory Manual*, $3^{rd}$ edition, Cold Spring Harbor Laboratory, Cold Spring Harbor, NY; *PCR Technology: Principles and Applications for DNA Amphlication*, ed. H A Erlich, Stockton Press, New York, NY (1989); U.S. Pat. No. 8,110,360.

6.3.1. Upstream and Downstream Library Sequences in Exogenous Donor Nucleic Acids In certain embodiments, an exogenous donor nucleic acid (ES) comprises a nucleic acid of interest (D) positioned between an upstream library sequence (UL) and a downstream library sequence (DL), wherein (UL) and (DL) are capable of initiating host cell mediated homologous recombination at one or more landing pads in the host cell's genome. In certain embodiments, for a library of exogenous donor nucleic acids, their upstream library sequences (UL) are identical or substantially identical, and their downstream library sequences (DL) are identical or substantially identical. To integrate an exogenous donor nucleic acid into the genome by homologous recombination, the exogenous donor polynucleotide generally comprises (UL) at one terminus and (DL) at the other terminus. In some embodiments, (UL) is homologous to a 5' region of one or more landing pads integrated in the host cell's genome, for example, an upstream landing pad homology sequence (ULP). In certain embodiments, (DL) is homologous to a 3' region of the one or more landing pads, for example, a downstream landing pad homology sequence (DLP). In some embodiments, (UL) comprises a nucleotide sequence that is about 70%, 75%, 80%, 85%, 90%, 95%, 96% 97%, 98%, 99% or 100% homologous or identical to a 5' region of one or more landing pads, for example, (ULP). In some embodiments, (DL) comprises a nucleotide sequence that is about 70%, 75%, 80%, 85%, 90%, 95%, 96%, 97%, 98%, 99%, or 100% homologous or identical to a 3' region of one or more landing pads, for example, (DLP).

In certain embodiments, (UL) is positioned 5' to a nucleic acid of interest (D). In some embodiments, (UL) is positioned immediately adjacent to the 5' end of (D). In some embodiments, (UL) is positioned upstream to the 5' of (D). In certain embodiments, (DL) is positioned 3' to a nucleic acid of interest (D). In some embodiments, (DL) is positioned immediately adjacent to the 3' end of (D). In some embodiments, (DL) is positioned downstream to the 3' of (D).

Typically, properties that may affect the integration of an exogenous donor polynucleotide at a landing pad include but are not limited to: the lengths of the upstream and downstream library sequences used for genomic integration, the overall length of the exogenous donor nucleic acid construct, and the nucleotide sequence or location of the genomic integration locus of the landing pad. For instance, effective heteroduplex formation between one strand of a library sequence and one strand of a particular landing pad homology sequence in a host cell's genome may depend on the length of the upstream and downstream library sequences of exogenous donor nucleic acids in relation to the landing pad homology sequences. An effective range for the length of a library sequence used as a genomic integration sequence is generally 20 to 5,000 nucleotides, typically 25 to 5,000 nucleotides, more typically 50 to 5,000 nucleotides. For a discussion of effective lengths of homology between genomic integration sequences and genomic loci. See, Hasty et al., Mol Cell Biol 11:5586-91 (1991).

In certain embodiments, (UL) and (DL) can comprise any nucleotide sequence of sufficient length and sequence identity that allows for genomic integration of the exogenous nucleic acid (ES) at any landing pads with compatible landing pad homology sequences. In certain embodiments, each of (UL) and (DL) independently consists of about 20 to 5,000 nucleotides. In certain embodiments, each of (UL) and (DL) independently consists of about 100 to 2,500 nucleotides. In certain embodiments, each of (UL) and (DL) independently consists of about 100 to 1,000 nucleotides. In certain embodiments, each of (UL) and (DL) independently consists of about 250 to 750 nucleotides. In certain embodiments, each of (UL) and (DL) independently consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of (UL) and (DL) independently consists of about 500 nucleotides.

In certain embodiments, the nucleotide sequences of (UL) in the one or more exogenous donor nucleic acids are substantially identical to one another. In certain embodiments, the nucleotide sequences of (DL) in the one or more exogenous donor nucleic acids are substantially identical to one another. For example, all (UL) in the one or more exogenous donor nucleic acids comprise nucleotide sequences that are at least 70%, 75%, 80%, 85%, 90%, 95%, 96%, 97%, 98%, 99%, or 100% identical to one another; and all (DL) in the one or more exogenous donor nucleic acids comprise nucleotide sequences that are at least 70%, 75%, 80%, 85%, 90%, 95%, 96%, 97%, 98%, 99%, or 100% identical to one another. In some embodiments, the nucleotide sequences of all (DL) in the one or more exogenous donor nucleic acids are identical to one another; and the nucleotide sequences in all (DL) in the one or more exogenous donor nucleic acids are identical to one another.

6.3.2. Nucleic Acids of Interest

In some embodiments, the exogenous donor nucleic acid further comprises a nucleic acid of interest (D). The nucleic acid of interest can be any DNA segment deemed useful by one of skill in the art. For example, the DNA segment may comprise a gene of interest that can be "knocked in" to a host genome. In other embodiments, the DNA segment functions as a "knockout" construct that is capable of specifically disrupting a target gene upon integration of the construct into the target site of the host cell's genome, thereby rendering the disrupted gene non-functional. Useful examples of a nucleic acid of interest (D) include but are not limited to: a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, a spacer or stuffer sequence (e.g., a randomly generated sequence with no known function), a linker sequence, a degron sequence, a fusion partner sequence, any other naturally occurring or synthetic DNA molecule, or a combination or a subcombination thereof. In some embodiments, (D) can be of natural origin. Alternatively, (D) can be completely of synthetic origin, produced in vitro.

Furthermore, (D) can comprise any combination of isolated naturally occurring DNA molecules, or any combination of an isolated naturally occurring DNA molecule and a synthetic DNA molecule. For example, (D) may comprise a heterologous promoter operably linked to a protein coding sequence, a protein coding sequence linked to a poly-A tail, a protein coding sequence linked in-frame with a epitope tag coding sequence, and the like. The nucleic acid of interest (D) may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., Molecular Cloning, A Laboratory Manual, 3d. ed., Cold Spring Harbor Laboratory Press, Cold Spring Harbor, New York (2001); Glover, D. M. (ed.), DNA Cloning: A Practical Approach, 2d. ed., MRL Press, Ltd., Oxford, U.K. (1995).

In particular embodiments, the nucleic acid of interest (D) does not comprise nucleic acid encoding a selectable marker. In these embodiments, the high efficiency of integration provided by the methods described herein allows for the screening and identification of integration events without the requirement for growth of transformed cells on selection media. However, in other embodiments where growth on selective media is nonetheless desired, the nucleic acid of interest (D) can comprise a selectable marker that may be used to select for the integration of the exogenous nucleic acid into a host genome.

A wide variety of selectable markers are known in the art (see, for example, Kaufinan, Meth. Enzymol. 185:487 (1990); Kaufman, Meth. Enzymol., 185:537 (1990); Srivastava and Schlessinger, Gene, 103:53 (1991); Romanos et al., in DNA Cloning 2: Expression Systems, 2nd Edition, pages 123-167 (IRL Press 1995); Markie, *Methods Mol. Biol.,* 54:359 (1996); Pfeifer et al., *Gene,* 188:183 (1997); Tucker and Burke, *Gene,* 199:25 (1997); Hashida-Okado et al., *FEBS Letters,* 425:117 (1998)). In some embodiments, the selectable marker is a drug resistant marker. A drug resistant marker enables cells to detoxify an exogenous drug that would otherwise kill the cell. Illustrative examples of drug resistant markers include but are not limited to those which confer resistance to antibiotics such as ampicillin, tetracycline, kanamycin, bleomycin, streptomycin, hygromycin, neomycin, Zeocin™, and the like. In other embodiments, the selectable marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine free media in the presence of histidinol. Other selectable markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like. In other embodiments, the selectable marker is a marker other than one which rescues an auxotrophic mutation. For example, the host cell strain can comprise mutations other than auxotrophic mutations, for example, mutations that are not lethal to the host and that also do not cause adverse effects on the intended use of the strain, e.g., industrial fermentation, so long as the mutations can be identified by a known selection method.

Host cell transformants comprising a chromosomally integrated polynucleotide can also be identified by selecting host cell transformants exhibiting other traits encoded by individual DNA segments (e.g., component polynucleotides) or by combinations of DNA segments, e.g., expression of peptides that emit light, or by molecular analysis of individual host cell colonies, e.g., by restriction enzyme mapping, PCR amplification, or sequence analysis of isolated assembled polynucleotides or chromosomal integration sites. In certain embodiments, a barcode sequence associated with each exogenous donor nucleic acid can be used to identify individual DNA segments or combinations of DNA segments integrated in the host cell's genome.

6.3.3. Component Polynucleotides and their Integration at Landing Pads

Most large-scale host cell engineering involves the use and re-use of existing DNA parts. In certain embodiments, exogenous donor nucleic acids are DNA parts (also referred to as component polynucleotides) that can be co-transformed as modular parts to generate various combinations of assembled polynucleotides. When various combinations of assembled polynucleotides are integrated in the landing pads, they generate a greater molecular diversity in the engineered host cells, as compared to a single piece polynucleotides with homology sequences at both 5' and 3' regions for integration in the landing pads. The greater molecular diversity can result in more diverse phenotypes exhibited by the engineered host cells. Such results are demonstrated in FIGS. 10A-10C, which is described in further detail below. Furthermore, the use of component polynucleotides as modular parts can save time and cost in generating host cells because the component polynucleotides are combinatorially assembled in vivo and combinatorially integrated into the host cell's genome. Also, the component polynucleotides do not need to be re-customized for integration in different host cell background or at different genomic loci if the host cell comprises landing pads with compatible homology sequences.

Thus, provided herein are component polynucleotides, which can be assembled in vivo via homologous recombination to generate assembled component polynucleotides. In certain embodiments, two component polynucleotides—a first component polynucleotide and a last component polynucleotide—are homologously recombined in a host cell in vivo to integrate into any of the landing pads in the host cell's genome. In this embodiment, each of one or more first component polynucleotides comprises, in a 5' to 3' orientation: an upstream library sequence (UL) capable of homologously recombining with an upstream landing pad homology sequence (ULP); a first nucleic acid of interest, and a first linker sequence. Each of one or more last component polynucleotides comprises, in a 5' to 3' orientation: a last linker sequence, a last nucleic acid of interest, and a downstream library sequence (DL) capable of homologously recombining with the downstream landing pad homology sequence (DLP). Each first linker sequence at the 3' end of the one or more first component polynucleotides is capable of homologously recombining with each last linker sequence at the 5' end of the one or more last component polynucleotides to generate various combinations of component polynucleotides. Upon induction of a double-stranded break within the landing pad by a site-specific nuclease, endogenous homologous recombination machinery integrates the assembled component polynucleotides at the cleaved site in the landing pad with high integration efficiencies. An example of two component polynucleotides is illustrated shown in the middle of FIG. 1E.

In certain embodiments, three or more different types of component polynucleotides (e.g., a first component polynucleotide, an intermediate component polynucleotide, and a last component polynucleotide) are co-transformed into a host cell. In this embodiment, each of one or more first component polynucleotides comprises, in a 5' to 3' orientation, an upstream library sequence (UL) capable of homologously recombining with the upstream landing pad homology sequence (ULP), any DNA segment selected from the group $D_0$, a linker sequence $LB_0$. Each of one or more intermediate component polynucleotides comprises, in a 5' to 3' orientation, a first linker sequence LAS, any DNA segment selected from the group $D_n$, a second linker sequence $LB_n$. In this embodiment, n represents an integer from one to the number of intermediate component polynucleotides. Each of one or more last component polynucleotides comprises, in a 5' to 3' orientation, a linker sequence $LA_m$, any DNA segment selected from the group $D_m$, and a downstream library sequence (DL) capable of homologously recombining with the downstream landing pad homology sequence (DLP). In this embodiment, each linker sequence $LB_{(p-1)}$ is capable of homologously recombining with the linker sequence $LA_p$, wherein n is an integer that varies from 1 to (m−1), wherein p represents an integer from 1 to m, and wherein each group $D_0, \ldots D_n, \ldots D_m$, independently consists of one or more DNA segments.

In certain embodiments, a DNA segment (in Group $D_0$, group $D_n$, or group $D_m$) can be any nucleic acids of interest. For example, any nucleic acids of interest described in Section 5.2.2 can be incorporated as a DNA segment in component polynucleotides.

In certain embodiments, three component polynucleotides can be assembled and integrated into the landing pad. An example of three component polynucleotides (a first component polynucleotide, an intermediate component polynucleotide, and a last component polynucleotide) is illustrated at the bottom of FIG. 1E.

In certain embodiments, linker sequences that homologously recombine component polynucleotides to one another in vivo can be of any nucleotide sequence of sufficient length and sequence identity that allows for homologous recombination to its counterpart linker sequence. In certain embodiments, each linker sequence consists of about 20 to 5,000 nucleotides. In certain embodiments, each linker sequence consists of about 24 to 2,500 nucleotides. In certain embodiments, each linker sequence consists of about 24 to about 1,000 nucleotides. In certain embodiments, each linker sequence consists of about 24 to about 500 nucleotides. In certain embodiments, each linker sequence consists of about 24 to about 100 nucleotides. In certain embodiments, shorter linker sequences (e.g., about 24 to about 36 nucleotides) are used when they are used to assemble two component polynucleotides with DNA segments that need to be in close proximity (e.g., a promoter and an open reading frame). For example, linker sequence "A" shown in FIG. 1E which are used to connect a promoter to an open reading frame can be a relatively short sequence (e.g., about 24 to about 36 nucleotides). On the other hand, linker sequence "SNAP" shown in FIG. 2C which are used to assemble two open reading frames can be relatively long sequences (e.g., 500 to 5000 nucleotides).

In certain embodiments, the two linker sequences that homologously recombine component polynucleotides in vivo can comprise nucleotide sequences that are about 70%, 75%, 80%, 85%, 90%, 95%, 96% 97%, 98%, 99% or 100% homologous or identical to one another. For example, if a first component polynucleotide and a last component polynucleotide are assembled in vivo and integrate into a landing pad, a first linker sequence at the 3' end of the first component polynucleotide and a last linker sequence at the 5' end of the last component polynucleotide comprise nucleotide sequences that are about 70%, 75%, 80%, 85%, 90%, 95%, 96%, 97%, 98%, 99%, or 100% homologous or identical to each other. When one or more intermediate component polynucleotides are co-introduced with one or more first component polynucleotides and one or more last component polynucleotides, linker sequence $LB_{(p-1)}$ and linker $LA_p$ comprise nucleotide sequences that are about 70%, 75%, 80%, 85%, 90%, 95%, 96%, 97%, 98%, 99%, or 100% homologous or identical to each other.

Suitable component polynucleotides and other features related to component polynucleotides are further described in detail in U.S. Pat. No. 8,110,360, which is incorporated herein by reference in its entirety.

6.3.4. Additional Functional Elements: Barcode Sequences and Additional Nuclease Target Sequences Exogenous donor nucleic acids provided herein can comprise additional functional elements. In certain embodiments, the additional functional elements can include a nuclease target sequence which is different from those present in the exogenous landing pad(s) in the host cell's genome. For example, as shown in FIG. 3A, a first component polynucleotide comprises a promoter (shown as a curved arrow) positioned between an upstream library sequence (UL) and a first linker sequence ("A"). The first component polynucleotide shown in FIG. 3A further comprises a nuclease target sequence "Y" cleavable by a nuclease Y-cutter, which is different from the target nuclease sequence "X" within the landing pads in the host cell's genome (shown in FIG. 3C). The last component polynucleotide shown in FIG. 3B comprises an open reading frame (ORF) positioned between a last linker sequence ("A") and a downstream library sequence (DL). The last component polynucleotide further comprises a nuclease target sequence "Z" cleavable by a nuclease Z-cutter, which is different from the target nuclease sequence "X" within the landing pads in the host cell's genome. Upon recombination and integration of the component polynucleotides into the landing pads, these additional nuclease target sequences (e.g., Y and Z sites) can be utilized later to further introduce additional exogenous donor nucleic acids in the host cell's genome during subsequent transformations.

In certain embodiments, a unique barcode of a known sequence is associated with each exogenous donor nucleic acid. The barcode sequence can be used to further facilitate identification of exogenous donor nucleic acids that are integrated within the landing pads in the host cell's genome. Generally, barcode sequences are of a sufficient length and sufficiently different from one another to allow identification of exogenous donor nucleic acids or component polynucleotides integrated in the landing pads in the host cell's genome. In certain embodiment, each barcode sequence may include at least 4, 5, 6, 7, 8, 9, 10, 11, 12, 13, 14, 15, 16, or more nucleotides in length. In an embodiment, a barcode sequence can include 7 nucleotides in length.

A barcode sequence can be incorporated at any suitable location in each exogenous donor nucleic acid or in a component polynucleotide. Exemplary locations of a barcode sequence in component polynucleotides are shown as a series of horizontal bar lines (also noted as "NNNNNNN 7 nt barcode") in FIGS. 3A and 3B. In certain embodiments, a first component polynucleotide can comprise a barcode sequence positioned between an upstream library sequence (UL) and a nucleic acid of interest (e.g., a promoter shown as a curved arrow). In certain embodiments, a last component polynucleotide can comprise a barcode sequence positioned between a downstream library sequence (DL) and a nucleic acid of interest (e.g., ORF). In particular embodiments, a barcode sequence can be inserted between an upstream library sequence (UL) and an additional functional element, such as a nuclease target sequence (e.g., Y-cutter site). In certain embodiments, a nuclease target sequence (e.g., Y-cutter site) is common to all first component polynucleotides in a given library. In particular embodiments, a barcode sequence can be inserted between a downstream library sequence and an additional element, such as a nuclease target sequence (e.g., Z-cutter site). In certain embodiments, a nuclease target sequence (e.g., Z-cutter site) is common to all last component polynucleotides in a given library. By integrating "Y" and "Z" nuclease target sequences into exogenous donor nucleic acids, they can serve as common primer binding sites for barcode amplification and to allow for additional rounds or cutting and nucleotide integration. In the embodiment shown in FIG. 3C, the identity of a first component polynucleotide integrated in the landing pad at the iALG1 locus can be determined by using a pair of the following standard primers: a primer which binds to a genomic sequence of iALG1 positioned upstream to the 5' of the (ULP) noted as "UL" and a primer $P_Y$ which binds to the "Y" nuclease target sequence. The identity of a last component polynucleotide integrated at the landing pad at the iALG1 locus can be determined by using a pair of the following standard primers: a primer $P_Z$ which binds to the "Z" nuclease target sequence and a primer which binds to a genomic sequence of iALG1 positioned downstream to the 3' of the (DLP) noted as "DL".

6.4 Methods of Genomic Integration of Exogenous Donor Nucleic Acids

Provided herein are methods for genomic integration of one or more exogenous donor nucleic acids into one or more landing pads engineered in the host cell's genome. As described above, in certain embodiments, each landing pad integrated into the host cell's genome comprises standardized homology sequences to facilitate host cell-mediated homologous recombination of exogenous donor nucleic acids. In such embodiments, the standardized landing pad homology sequences allow any exogenous donor nucleic acids to be integrated at any landing pads in the host cell's genome, as long as exogenous donor nucleic acids themselves comprise homology sequences compatible with the landing pad homology sequences. Therefore, in certain embodiments, an integration event of exogenous donor nucleic acids is independent of the genomic locus surrounding the landing pads and does not rely on homology with endogenous genomic sequences for recombination. In particular embodiments, the methods comprise contacting the host cell with one or more exogenous donor nucleic acids and one or more nucleases capable of cleaving the nuclease target sequence located in the landing pad. Cleavage within the landing pad greatly increases the frequency of homologous recombination at or near the cleavage site.

6.4.1. Integration of Exogenous Donor Nucleic Acids at Landing Pads

FIG. 1A through 1C illustrate an exemplary embodiment of a method of markerless genomic integration of a single exogenous donor nucleic acid from a library of exogenous donor nucleic acids at a single landing pad using a site-specific nuclease. An exogenous donor nucleic acid is introduced into a host cell, wherein the exogenous donor nucleic acid comprises a nucleic acid of interest (e.g., an ORF operably linked to a promoter) flanked by an upstream library sequence (UL) and a downstream library sequence (DL). In the embodiment shown in FIGS. 1A to 1C, (UL) and (DL) of exogenous donor nucleic acids share sequence identity with the upstream landing pad homology sequence (ULP) and a downstream landing pad homology sequence (DLP), respectively, of the landing pad. In the embodiment shown in FIG. 1B, there are four different exogenous donor nucleic acids that can integrate in the landing pad shown in FIG. 1A. A site-specific nuclease (shown as a pair of scissors) recognizes and cleaves the nuclease target sequence (NTS shown as "X") in the landing pad. Upon induction of a double-stranded break within the nuclease target sequence by the site-specific nuclease, endogenous homologous recombination machinery integrates the nucleic acid of interest at the cleaved site. As shown in FIG. 1C, once integrated into the host cell's genome, the nucleic acid of interest is positioned between the upstream and downstream landing pad homology sequences (UL and DL shown in FIG. 1C), which are nested within a neutral genomic locus (e.g., an intergenic region downstream of the ALG1 locus in yeast genome). As illustrated in FIGS. 1A to 1C, the genomic integration event of the exogenous donor nucleic acid does not rely on endogenous genomic sequences for homologous recombination. FIGS. 1D through 1F illustrate an alternative embodiment of a landing pad and exogenous donor nucleic acids and component polynucleotides suitable for integration in the landing pad.

In the embodiment illustrated in FIGS. 1A to 1F, the endogenous homologous recombination machinery integrates the nucleic acid of interest at the cleaved site at a higher frequency as compared to a genomic site not comprising a double-stranded break. This increased frequency of integration obviates the need to co-integrate a selectable marker in order to select transformants having undergone a recombination event. By eliminating the need for selectable markers, for example, during construction of an engineered microbe, the time needed to build a strain comprising a complete and functional biosynthetic pathway is greatly reduced. In addition, engineering strategies are no longer limited by the need to recycle selectable markers due to there being a limited cache of markers available for a given host organism.

In some embodiments, markerless recovery of a transformed cell comprising a successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery of a transformed cell comprising a successfully integrated exogenous nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated exogenous nucleic acid occurs within a frequency of about one every 9, 8, 7, 6, 5, 4, 3, or 2 contacted host cells, or clonal populations thereof, screened. In certain embodiments, the success rate of integration of exogenous donor nucleic acids into all landing pads (e.g., 3 landing pads) engineered into the host cell's genome is greater than 90%. In certain embodiments, the success rate of integration of exogenous donor nucleic acids into all landing pads (e.g., 3 landing pads) engineered into the host cell's genome is greater than 95%. In more particular embodiments, the host cell is a yeast cell, and the increased frequency of integration derives from yeast's increased capacity for homologous recombination relative to other host cell types.

A variety of methods are available to identify those cells having exogenous donor nucleic acids integrated in the landing pads without the use of a selectable marker. In some embodiments, such methods seek to detect any change in the landing pads, and include but are not limited to PCR methods, sequencing methods, nuclease digestion, e.g., restriction mapping, Southern blots, and any combination thereof. In certain embodiments, barcode sequences associated with exogenous donor nucleic acids can be used to determine identities of exogenous donor nucleic acids integrated at the landing pads. Because the success rate of genomic integration of exogenous donor nucleic acids (or component polynucleotides) in the landing pad is high, the transformed host cells' phenotypes can be used to identify those cells having exogenous donor nucleic acids of interest without genotyping the host cells.

In a particular embodiment, provided herein is a method for simultaneous genomic integration of exogenous nucleic acids in a plurality of exogenous landing pads the host cell's genome. The method comprises:
(a) contacting a host cell, the host cell comprising a plurality of (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), with:
  (i) one or more exogenous donor nucleic acids (ES), wherein each (ES) comprises a nucleic acid of interest (D) positioned between an upstream library sequence (UL) and a downstream library sequence (DL), wherein each (UL) is capable of homologously recombining at any (ULP), and each (DL) is capable of homologously recombining at any (DLP), of any of the (x) exogenous landing pads; and
  (ii) one or more nuclease (N) capable of binding to (NTS) of any of the plurality of (x) exogenous landing pads and cleaving a site within the (x) exogenous landing pads; and
(b) recovering a host cell generated from the contacted host cell, wherein any of the exogenous donor nucleic acids (ES) is integrated at any of the plurality of (x) exogenous landing pads, independent of genomic sequences surrounding each landing pad. In certain embodiment, x is an integer of at least two. In certain embodiments, x is an integer of 1, 2, 3, 4, 5, 6, 7, 8, 9, 10, 11, 12, 13, 14, 15, 16, 17, 18, 19, or 20.

FIGS. 2A and 2B illustrate an exemplary embodiment of simultaneous genomic integration of a plurality of exogenous donor nucleic acids into a plurality of landing pads. As described above, FIG. 2A illustrates an exemplary host cell comprising three landing pads at intergenic regions downstream of genomic loci ALG1, MGA1, and YCT1. In this embodiment, each landing pad comprises a nuclease target sequence (NTS) shown as "X," cleavable by nuclease X-cutter (e.g., CphI), which is positioned between an upstream landing pad homology sequence (ULP) and a downstream landing pad homology sequence (DLP). In the embodiment shown in FIG. 2A, all three landing pads have the same nucleotide sequences "UL" for (ULP), the same nucleotide sequences for "DL" for (DLP), and the same nuclease target sequence X. Therefore, in the exemplary embodiment shown in FIG. 2A, all three landing pads are standardized to integrate any exogenous donor nucleic acids which comprise compatible homology sequences for integration into any of the landing pads.

FIG. 2B illustrates a library of exogenous donor nucleic acids which comprises homology sequences (referred to as library sequences) that are compatible for host cell-mediated homologous recombination with the landing pad homology sequences. In the embodiment illustrated in FIG. 2B, each exogenous donor nucleic acid comprises a nucleic acid of interest, which is a gene or an open reading frame ("ORF") operably linked to a promoter (shown as a curved arrow upstream to ORF). In FIG. 2B, each nucleic acid of interest (D) is positioned between an upstream library sequence (noted as "UL" in FIG. 2B) and a downstream library sequence (noted as "DL" in FIG. 2B). When introduced into the host cell, each upstream library sequence (UL) of an exogenous donor nucleic acid is capable of homologously recombining at any upstream landing pad homology sequence (ULP), and each downstream library sequence (DL) of an exogenous donor nucleic acid is capable of homologously recombining at any downstream landing pad homology sequence (DLP), via host cell mediated homologous recombination.

In some embodiments, two or more different types of exogenous donor nucleic acids shown in FIG. 2B can be contacted with the host cell so that different combinations of exogenous donor nucleic acids can be integrated into the landing pads in the host cell's genome. In some embodiments, the molar ratios of different types of exogenous donor nucleic acids can be varied to influence the integration rates of each type of exogenous donor nucleic acid relative to one another. In other embodiments, a single type of exogenous donor nucleic acid can be introduced into the host cell so that multiple copies of the same exogenous donor nucleic acid can be integrated at the standardized landing pads in the host cell's genome.

In some embodiments, the exogenous donor nucleic acid may be introduced in combination with another exogenous donor nucleic acid comprising a "stuffer" or "spacer" sequence (e.g., randomly generated, non-functional sequence). See, e.g., FIG. 4. By using an exogenous donor nucleic acid comprising a stuffer sequence, a copy number of the other functional nucleic acid integrated in the host cell's genome can vary. For example, some of host cells transformed with these two DNA constructs can include a single copy of ORF1 and two copies of a spacer sequence, two copies of ORF1 and one copy of a spacer sequence, three copies of ORF1 and no spacer sequence, and the like, integrated in the three landing pads. In certain embodiments, an exogenous donor nucleic acid comprising a stuffer sequence can be co-introduced in combination with two or more different types of exogenous donor nucleic acids to generate host cells with different copy numbers of each type of exogenous donor nucleic acid integrated in the landing pads.

In the embodiment illustrated in FIGS. 2A and 2B, nuclease X-cutter (e.g., CphI) is also introduced to the host cell, wherein the nuclease X-cutter is capable of recognizing and cleaving a unique sequence within its corresponding nuclease target sequence (NTS). Upon cleavage of a nuclease target sequence (NTS) by the nuclease X-cutter, endogenous homologous recombination machinery facilitates simultaneous integration of any of exogenous donor nucleic acids (e.g., comprising ORF1, ORF2, ORF3, or ORF4) at any three standardized landing pads at a higher frequency as compared to a landing pad not comprising a double-strand break. Since any of four open reading frames can integrate at any of the three landing pads, the method provided herein generates a diverse population of host cells with various combinations of open reading frames integrated in the landing pads.

In certain embodiments, the number of different types of exogenous nucleic acids (ES) contacting a host cell is not limited by the number (x) of landing pads present in the host cell's genome. In one embodiment, the number of different types of exogenous donor nucleic acids introduced into the host cell can exceed the number (x) of landing pads present in the host cell's genome. In other embodiments, the number of different types of exogenous donor nucleic acids introduced into the host can be less than the number (x) of landing pads present in the host cell's genome.

As with integration of a single exogenous nucleic acid at a single landing pad illustrated in FIGS. 1A to 1C, the simultaneous multiple integration of a plurality of exogenous donor nucleic acids occurs at a substantially higher frequency as compared to not contacting the landing pads with a nuclease capable of inducing a double-stranded break. In some embodiments, this increased frequency of integration obviates the requirement for co-integration of one or more selectable markers for the identification of the plurality of recombination events. In some embodiments, markerless recovery of a transformed cell comprising a plurality of successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery occurs within a frequency of about one every 90, 80, 70, 60, 50, 40, 30, 20, or 10 contacted host cells, or clonal populations thereof, screened. In more particular embodiments, markerless recovery occurs within a frequency of about one every 9, 8, 7, 6, 5, 4, 3, or 2 contacted host cells, or clonal populations thereof, screened. In certain embodiments, the success rate of integration of exogenous donor nucleic acids into all landing pads (e.g., 3 landing pads) engineered into the host cell's genome is greater than 90%. In certain embodiments, the success rate of integration of exogenous donor nucleic acids into all landing pads (e.g., 3 landing pads) engineered into the host cell's genome is greater than 95%. In more particular embodiments, the host cell is a yeast cell, and the increased frequency of integration derives from yeast's increased capacity for homologous recombination relative to other host cell types.

6.4.1.1 Integration of Component Polynucleotides at Landing Pads

In another aspect, provided herein is a method for integrating exogenous donor nucleic acids which are component polynucleotides. The component polynucleotides, when introduced into the host cell, homologously recombine with one another to generate one or more assembled component polynucleotides. These assembled component polynucleotides comprise homology regions at their 5' and 3' ends, which allow them to homologously recombine and integrate at any of the landing pads in the host cell's genome. In certain embodiments, each component polynucleotide comprises at least one linker sequence, which allows each component polynucleotide to homologously recombine with another component polynucleotide in vivo using the linker sequences. In certain embodiments, the component polynucleotides are co-introduced into a host cell in a single transformation reaction.

Thus, in one aspect, provided herein is a method of genomically integrating component polynucleotides in one or more landing pad in the host cell's genome. In one embodiment, the method comprises:
(a) contacting a host cell, comprising one or more (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), with:
 (i) one or more first component polynucleotides, wherein each first component polynucleotide comprises, in a 5' to 3' orientation:
  (1) an upstream library sequence (UL) capable of homologously recombining with the upstream landing pad homology sequence (ULP);
  (2) a first nucleic acid of interest, and
  (3) a first linker sequence;
 (ii) one or more last component polynucleotides, wherein each last component polynucleotide comprises, in a 5' to 3' orientation:
  (1) a last linker sequence,
  (2) a last nucleic acid of interest, and
  (3) a downstream library sequence (DL) capable of homologously recombining with the downstream landing pad homology sequence (DLP),
  wherein any first linker sequence of the one or more first component polynucleotides is capable of homologously recombining with any last linker sequence of the one or more last component polynucleotides; and
 (iii) a nuclease (N) capable of cleaving any (NTS) in any of the one or more (x) exogenous landing pads; and
(b) recovering a host cell generated from the contacted host cell, wherein any combination of a first component polynucleotide from the one or more first component polynucleotides and a last component polynucleotide from the one or more last component polynucleotides, which are homologously recombined in vivo via their linker sequences, is integrated at any of the one or more (x) exogenous landing pads, independent of genomic sequences surrounding each landing pad. In some embodiments, x is an integer of at least one.

In this embodiment, a component polynucleotide is referred to as a first component polynucleotide if it comprises a homology region at its 5' end to homologously recombine and integrate into an upstream landing pad homology sequence (ULP) in one or more landing pads. Similarly, a component polynucleotide is referred to as a last component polynucleotide if it comprises a homology region at its 3' end to homologously recombine with a downstream landing pad homology sequence (DLP) in one or more landing pads.

In certain embodiments, the number (x) of landing pads present in the host cell's genome is at least two, and any combinations of first and last component polynucleotides are integrated at any of the (x) number of landing pads. In certain embodiments, the number (x) of landing pads present in the host cell's genome is 3, 4, 5, 6, 7, 8, 9, 10, 11, 12, 13, 14, 15, 16, 17, 18, 19, or 20. In certain embodiments, any combinations of first and last component polynucleotides are integrated at any of these multiple (x) landing pads.

FIG. 2C illustrates an exemplary embodiment of component polynucleotides which can be combinatorially combined and combinatorially integrated into any of the three landing pads present in the host cell's genome. As shown in FIG. 2C, two open reading frames, each operably linked to its own promoter, are combinatorially combined to integrate the assembled component polynucleotides into any of the landing pads shown in FIG. 2A. In FIG. 2C, the first component polynucleotide comprises, in a 5' to 3' orientation, an upstream library sequence (UL), an open reading frame ORF1 operably linked to a promoter, and a first linker sequence "SNAP". The upstream library sequence (UL) of the first component polynucleotide is capable of homologously recombining with the upstream landing pad homology sequence (ULP), which has the same sequence as the upstream library sequence (UL) in the embodiment shown in FIG. 2A. The last component polynucleotide comprises, in a 5' to 3' orientation, a last linker sequence SNAP, an open reading frame operably linked to a promoter, and a downstream library sequence DL capable of homologously recombining with the downstream landing pad homology sequence (DLP). In the exemplary embodiment shown in FIG. 2A, the (DLP) has the same sequence as the downstream library sequence (DL). The first linker sequence (i.e., SNAP in FIG. 2C) of the first component polynucleotide is capable of homologously recombining in vivo with the last linker sequence (i.e., SNAP in FIG. 2C) of the last component polynucleotide to generate assembled component polynucleotides. When homologously recombined, the assembled component polynucleotides generates a multiple open reading frame, with each open reading frame operably linked to its own promoter (referred to as "locked promoter" design). The upstream library sequence (UL) in the first component polynucleotides and the downstream library sequence (DL) in the last component polynucleotides allow integration of the assembled component polynucleotides in any of the three landing pads in the host cell's genome shown in FIG. 2A. Any of the assembled component polynucleotides can be combinatorially integrated at any of the multiple landing pads.

While component polynucleotides shown in FIG. 2C illustrate each open reading frame operably linked to its own promoter, in some embodiments, the promoter can be separated from the open reading frame and co-introduced into the host cell as two different component polynucleotides. For example, in FIG. 2C, the component polynucleotide comprising (UL) and ORF can be separated into two separate component polynucleotides (a promoter component polynucleotide with a linker sequence A and a promoterless ORF1 with a linker sequence A); and the component polynucleotides comprising (DL) and ORF2, ORF3, or ORF4 can be similarly separated into two separate component polynucleotides. By transforming the host cell with additional component polynucleotides which can combinatorially integrate into the host cell genome, a greater combinatorial diversity in strains can be generated.

FIG. 2D illustrates another exemplary embodiment of component polynucleotides being assembled together to integrate into landing pads in the host cell's genome. In the exemplary embodiment shown in FIG. 2D, component polynucleotides in "split-promoter" designs are illustrated: the first component polynucleotides comprise different promoters of varying promoter strengths; and the last component polynucleotides comprise different open reading frames. More specifically, a first component polynucleotide comprises, in a 5' to 3' direction, an upstream library sequence (UL) capable of homologously recombining with an upstream landing sequence (ULP) in a landing pad in the host cell's genome, a promoter; and a first linker sequence represented by "A." A last component polynucleotide comprises, in a 5' to 3' direction, a last linker sequence represented by "A," an open reading frame (e.g., ORF1, ORF2, ORF3, and ORF4), and a downstream library sequence (DL) capable of homologously recombining with a downstream landing sequence (DLP) in a landing pad in the host cell's genome. When one or more first component polynucleotides are introduced into the host cell in combination with one or more last component polynucleotides, the first linker sequence A of the first component polynucleotides homologously recombines with the last linker sequence A of the last component polynucleotides to generate different combinations of assembled component polynucleotides. When four different first component polynucleotides are co-introduced into the host cell with four different last component polynucleotides as shown in FIG. 2D, the host cell can potentially generate and integrate 16 different assembled component polynucleotides into the three landing pads shown in FIG. 2A. Since different copy numbers of each assembled component polynucleotides can be integrated in the three landing pads, the randomness of integration into standardized landing pads can further generate additional genetic variations in the host cells.

While FIGS. 2C and 2D illustrate exemplary embodiments where a combination of two component polynucleotides (i.e., first component polynucleotide and last component polynucleotide) is used to generate different combinations of assembled component polynucleotides, a combination of three or more component polynucleotides can be used to generate assembled component polynucleotides in vivo. For example, in certain embodiments, one or more intermediate component polynucleotides can be assembled between a first component polynucleotide and a last component polynucleotide to generate DNA assemblies of component polynucleotides. Furthermore, while FIG. 2D illustrate component polynucleotides which comprise a promoter adjacent to (UL), in some embodiments, a promoter can be incorporated between (DL) and a linker sequence.

Thus, in one aspect, provided herein is a method of genomically integrating three or more component polynucleotides, which are assembled in vivo, to integrate into any of one or more landing pads engineered into the host cell's genome. In one embodiment, the method comprises: (a) contacting a host cell, comprising one or more (x) exogenous landing pads integrated in a host cell's genome, wherein each of the one or more exogenous landing pads comprises a nuclease target sequence (NTS) positioned between an upstream landing pad homology sequence (ULP) and a downstream landing pad homology sequence (DLP), with:

(i) one or more first component polynucleotides, wherein each first component polynucleotide comprises, in a 5' to 3' orientation, an upstream library sequence (UL) capable of homologously recombining with the upstream landing pad homology sequence (ULP), any DNA segment selected from the group $D_0$, a linker sequence $LB_0$;

(ii) one or more intermediate component polynucleotides, wherein each intermediate component polynucleotide comprises, in a 5' to 3' orientation, a first linker sequence $LA_n$, any DNA segment selected from the group $D_n$, a second linker sequence $LB_n$, wherein n represents an integer from one to the number of intermediate component polynucleotides;

(iii) one or more last component polynucleotides, wherein each last component polynucleotide comprises, in a 5' to 3' orientation, a linker sequence $LA_m$, any DNA segment selected from the group $D_n$, and a downstream library sequence (DL) capable of homologously recombining with the downstream landing pad homology sequence (DLP), wherein each linker sequence $LB_{(p-1)}$ is capable of homologously recombining with the linker sequence $LA_p$, wherein n is an integer that varies from 1 to (m−1), wherein p represents an integer from 1 to m, and wherein each group $D_0, \ldots D_n, \ldots D_m$, independently consists of one or more DNA segments; and (b) recovering a host cell generated from the contacted host cell, wherein any combination of a first component polynucleotide from the one or more first component polynucleotides, an intermediate component polynucleotide from the one or more intermediate component polynucleotides, and a last component polynucleotide from the one or more last component polynucleotides, which are homologously recombined in vivo via their linker sequences, is integrated at any of the one or more (x) exogenous landing pads, independent of genomic sequences surrounding each landing pad. In some embodiments, x is an integer of at least one. In some embodiments, x is an integer of two. In some embodiments, x is an integer of three. In some embodiments, x is an integer of 4, 5, 6, 7, 8, 9, or 10.

In certain embodiments, the number (x) of landing pads present in the host cell's genome is at least two, and any combinations of first, intermediate, and last component polynucleotides are integrated at any of the landing pads. In certain embodiments, the number (x) of landing pads present in the host cell's genome is 3, 4, 5, 6, 7, 8, 9, 10, 11, 12, 13, 14, 15, 16, 17, 18, 19, or 20. In certain embodiments, any combinations of first, intermediate, and last component polynucleotides are integrated at any of these multiple landing pads.

Additional details of compositions and methods related to component polynucleotides can be found in U.S. Pat. No. 8,110,360, which is herein incorporated by reference in its entirety.

6.4.2. Tracking Genotype/Phenotype Relationships of Exogenous Donor Nucleic Acids The compositions and methods provided herein provide a rapid and efficient way to generate hundreds and thousands of combinatorial integrations of exogenous donor nucleic acids. The diverse combinatorial integration of exogenous donor nucleic acids can generate engineered host cells with certain observable traits or phenotypes (e.g., cellular function, target molecule production, and the like). Such different phenotypes generated by the diverse combinatorial integrations can be tracked and mapped with genotype contributions by various combinations of exogenous donor nucleic acids.

Thus, provided herein is a method of screening phenotype contributions by exogenous donor nucleic acids. In one embodiment, the method comprises:
(a) contacting a host cell with a plurality of exogenous nucleic acids (ES), each (ES) tagged with a barcode sequence, wherein the host cell's genome is configured to integrate any one or combinations of the plurality of (ES) in the host cell's genome via host cell-mediated homologous recombination;
(b) screening host cells, generated from the contacted host cell, which exhibit a specific phenotype; and
(c) determining, using the barcode sequence associated with each (ES), identities of (ES) integrated into the host cell's genome.

In certain embodiments, the host cells' genome is configured to integrate any one or combinations of the plurality of (ES) in the host cell's genome by providing a plurality of (x) exogenous landing pads integrated in the host cell's genome. In certain embodiments, each exogenous landing pad comprises a nuclease target sequence (NTS) positioned between an upstream landing pad homology sequence (ULP) and a downstream landing pad homology sequence (DLP) in each landing pad. In certain embodiments, the host cell is simultaneously contacted with a nuclease or a plasmid encoding a nuclease with the plurality of (ES).

In certain embodiments, at least two of the plurality of exogenous donor nucleic acids (ES) are component polynucleotides which are co-transformed into the host cell and assembled in vivo via homologous recombination to integrate at the landing pads. In such embodiment, each component polynucleotide can be associated with its unique barcode sequence which distinguishes each component polynucleotide from other component polynucleotides. In certain embodiments, one or more first component polynucleotides and one or more last component polynucleotides are contacted with the host cell to generate a plurality of assembled component polynucleotides integrated at the landing pads in the host cell's genome. In certain embodiments, one or more first component polynucleotides, one or more intermediate component polynucleotides, and one or more last component polynucleotides are contacted with the host cell to generate a plurality of assembled component polynucleotides integrated at the landing pads in the host cell's genome.

FIG. 4 illustrates one exemplary embodiment of a method of screening phenotype contributions by exogenous donor nucleic acids. As described above in relation to FIG. 2A, the host cell shown in FIG. 4 comprises three landing pads in the host cell's genome, wherein each landing pad comprises a nuclease target sequence (NTS) positioned between an upstream landing pad homology sequence (ULP) and a downstream landing pad homology sequence (DLP). The host cell is contacted with component polynucleotides (e.g., 9 first component polynucleotides comprising promoters of varying strengths and 10 last component polynucleotides comprising an open reading frame shown in FIG. 4), which, when homologously recombined in vivo, generate various combinations of assembled component polynucleotides. In the embodiment shown in FIG. 4, the host cell is simultaneously transformed with a plasmid encoding nuclease X (e.g., F-CphI), which is capable of cleaving the nuclease target sequence X in the landing pads.

The transformed cells can be grown in any suitable media. For example, as shown in FIG. 4, transformed host cells are plated on selective media to recover colonies. The colonies are picked and screened for "hits" or phenotypically interesting colonies using high-throughput screening. For instance, as shown in FIG. 4, the phenotypes of transformed host cells can be screened under two different assays, Assay 1 and Assay 2. Assay 1 can be, for example, the production of target molecules under one condition, and Assay 2 can be the production of target molecules under another condition. The transformed host cells that exhibit certain phenotypes can then be selected (e.g., high levels of target molecule productions in both assays). The selected host cells are then genotyped with standard primers to identify component polynucleotides (e.g., genes and promoters) integrated into the landing pads in the host cell's genome. FIG. 4 shows locations of standard primer binding sites. These standardized primers can be used to determine not only the component polynucleotides integrated in the landing pads, but also the genomic location of integration of (ES) in each colony. After genotype-phenotype relationships of various combinatorial integration of exogenous donor nucleic acids are determined, the composition of exogenous donor nucleic acids can be adjusted to further improve the desired phenotypes (e.g., the target molecule production) for genetically modified host cells.

While FIG. 4 illustrates an exemplary embodiment where an individual strain with certain phenotype(s) is selected and genotyped using barcode sequences, the genotype of a bulk population of combinatorially engineered host cells can be tracked using barcode sequences. In other words, instead of determining identities of exogenous donor nucleic acids integrated in individual transformants, multiple transformants with certain phenotypes (e.g., either desired or undesired phenotypes) can be pooled together to determine the genotype of the pooled population as a whole. For example, in the pooled population of various strains, it can be determined which exogenous donor nucleic acids are enriched in the population. In certain embodiments, the genotypes of the total population can be tracked over time without first determining their phenotypes through screening. For instance, a fermentation vessel can be inoculated with a mixed population of strains, and it can be determined which genotypes "succeed" over time. In certain embodiments, PCR reactions can be performed to amplify each landing pad region to determined identities of enriched exogenous donor nucleic acids in the pooled population. Any suitable sequencing method (e.g., next generation sequencing) can be used to determine a barcode sequence associated with amplicons generated from the PCR reactions. Based on the barcode information, it can be determined which exogenous donor nucleic acids in the pooled population of strains contribute to certain phenotypes. Based on this information, exogenous donor nucleic acids associated with undesired phenotypes can be de-prioritized and removed from the next round of combinatorial design, and those with desired phenotypes can be prioritized and iterated in the next round(s) of combinatorial design.

6.4.3. Genomic Integration with Addressable or Optional Landing Pads

In another aspect, provided herein are methods of genomic integration of exogenous donor nucleic acids in the host cell's genome comprising optional or addressable landing pads in addition or in alternative to primary, standardized landing pads shown in FIG. 2A. In certain embodiments, it may be desirable to create addressable landing pads in addition or in alternative to primary, standardized landing pads to perform targeted integration for a subset of exogenous donor nucleic acids. These landing pads are referred to as "addressable" landing pads, because a subset of exogenous donor nucleic acids can be addressed or directed to integrate into these landing pads, rather into the standardized primary landing pads.

FIG. 5B illustrates an exemplary embodiment where a secondary landing pad is different from the primary, standardized landing pads shown in FIG. 2A. In the embodiment illustrated in FIG. 2A, all three primary landing pads comprise the same upstream homology landing pad sequence "UL" for all (ULP) and the same downstream homology landing pad sequence "DL" for all (DLP). The fourth landing pad integrated at the locus$_1$ in the host cell's genome comprises an upstream landing pad homology sequence (UL), which is same as the primary standardized landing pads, but comprises a different downstream landing pad homology sequence (DL$_1$). The secondary landing pad with (UL) and (DL$_1$) can be used to integrate specific exogenous donor nucleic acid(s) (e.g., the last component polynucleotide A-ORF5-DL$_1$ shown in FIG. 5A) in combination with any of the first component polynucleotides with different promoters. These component polynucleotides can be co-transformed with other last component polynucleotides (A-ORF1-DL, A-ORF2-DL, A-ORF3-DL, and A-ORF4-DL) which are designed to combinatorially combine with any of the first component polynucleotides and integrate into the standardized, primary landing pads at ALG1, iMGA1, and iYCT1 loci.

FIG. 6B illustrates another exemplary embodiment which further comprises two optional and addressable landing pads which are different from the primary, standardized landing pads. The host cell shown in FIG. 6B comprises three primary landing pads that are integrated at intergenic regions iALG1, iMGA1, and iYCT1 in the host cell's genome. These primary landing pads comprise the same set of upstream landing pad homology sequence (UL), the same set of downstream landing pad homology sequence (DL), and the same set of nuclease recognition site X positioned between (UL) and (DL). As shown in FIG. 6B, the host cell further comprises two addressable landing pads at locus$_1$ and locus$_2$. These two addressable landing pads can be used to integrate specific exogenous donor nucleic acids (e.g., the last component polynucleotide A-ORF4-DL1 at locus$_1$ and the last component polynucleotide A-ORF5-DL2 at locus$_2$) in combination with any of the first component polynucleotides with different promoters. These component polynucleotides can be co-transformed with other last component polynucleotides (A-ORF1-DL, A-ORF2-DL, A-ORF3-DL) which are designed to combinatorially combine with any of the first component polynucleotides and integrate into the standardized landing pads.

The addressable landing pads at locus1 and locus2 are also optional landing pads, because they comprise target nuclease sequences that are not cleaved when an X-cutter is introduced to cleave primary landing pads, but are optionally "opened" or cleaved by separate nucleases. The optional landing pad at locus$_1$ comprises a target nuclease sequence "G", which is recognized by a G-cutter. The optional landing pad at locus$_2$ comprises a target nuclease sequence "H", which is recognized and/or cleavable by a H-cutter. These optional landing pads can be cleaved by its own nuclease (e.g., G-cutter and H-cutter) simultaneously with or sequentially after cleavage of primary landing pads.

FIG. 6A illustrates pooled DNA constructs (i.e., component polynucleotides) that can be used in combination with pooled "cutter" reagents (e.g., plasmids encoding nucleases). Since all landing pads shown in FIG. 6B have (UL) as the upstream landing pad homology sequence, the first set of component polynucleotides comprising (UL) as an upstream library sequence is compatible to homologously recombine with (UL) in any one of the five landing pads. On the other hand, the second set of component polynucleotides comprising ORF1, ORF2, or ORF3 can combinatorially integrate into any of the primary landing pads at the iALG1 locus, iMGA1 locus, and iYCT1 locus. However, only the component polynucleotide comprising ORF4 can integrate at the locus$_1$ due its (DL$_1$) homology to (DL$_1$) at the locus$_1$. Similarly, only the component polynucleotide comprising ORF5 can integrate at the locus$_2$ due to its (DL$_2$) homology to (DL$_2$) at locus$_2$.

There are many other variations for optional and/or addressable landing pads. For example, a host cell can comprise an additional set of landing pads which comprise different homology sequences for both upstream landing pad homology sequence and downstream landing pad homology sequence, compared to the primary set of standardized landing pads. In certain embodiments, a landing pad can comprise an upstream landing pad homology sequence which is exogenous to the genomic sequence (e.g., a randomly generated nucleotide sequence) and a downstream landing pad homology sequence which is endogenous to the genomic locus (e.g., an open reading frame of the genomic locus). In certain embodiments, a landing pad can comprise an upstream landing pad homology sequence which endogenous to the genomic locus (e.g., an open reading frame of the genomic locus) and a downstream landing pad homology sequence which is exogenous to the genomic locus.

6.4.4. Targeted Landing Pad and Integration of Exogenous Donor Nucleic Acids into the Targeted Landing Pad The compositions and methods provided herein can be applied in targeted integration of exogenous donor nucleic acids into specific genomic sites and screening their effects on the phenotype of genetically modified host cells. In certain embodiments, the targeted integration of exogenous donor nucleic acids at specific genomic sites can be achieved by integrating a landing pad at those genomic sites prior to introduction of exogenous donor nucleic acids into a host cell. Once integrated at the specific genomic sites adjacent to a genetic element of interest (e.g., an open reading frame), these landing pads allow exogenous donor nucleic acids to be integrated at specific genomic sites. Such an exogenous landing pad built at a specific genomic site is referred to as "targeted landing pads" because it allows exogenous donor nucleic acids to be targeted and integrated at the landing pads at specific genomic sites. Thus, in certain embodiments, exogenous donor nucleic acids comprising nucleic acids of interest (e.g., promoters, terminators, or degron sequences) can be integrated at the targeted landing pads to screen their effects on the transcription of the open reading frame and/or its protein expression or stability.

In certain embodiments, the targeted landing pads comprise homology sequences that are compatible with homology sequences of exogenous donor nucleic acids in the existing library of parts (e.g., (UL), (DL), (A) shown in FIG. 1E and FIGS. 2B to 2D). As such, a library of exogenous donor nucleic acids with standard library sequences and/or standardized linker sequences can be utilized for targeted integration into targeted landing pads at specific genomic sites without re-customization.

Thus, in one aspect, provided herein is a method for targeted integration of nucleic acids into a host cell's genome, the method comprising:
 (a) contacting a host cell, the host cell comprising an exogenous landing pad integrated 5' to an open reading frame, wherein the exogenous landing pad comprises a nuclease target sequence (NTS) positioned between an upstream landing pad homology sequence (ULP) and a downstream landing pad linker sequence (DLPL), with
  (i) one or more first component polynucleotides, each first component polynucleotide comprises, in a 5' to 3' orientation:
   (1) an upstream library sequence (UL) capable of homologously recombining with the (ULP);
   (2) a first nucleic acid of interest; and
   (3) a first linker sequence;
  (ii) a nuclease (N) capable of binding to the (NTS) and cleaving a site within the exogenous landing pad,
 (b) recovering a host cell generated from the contacted host cell,
 wherein the (DLPL) is capable of homologously recombining with the first linker sequence of any of the one or more first component polynucleotides to integrate a first component polynucleotide from the one or more first component polynucleotides at the exogenous landing pad.

In certain embodiments, an open reading frame is that of an endogenous gene at its native locus. In other embodiments, an open reading frame is that of an exogenous gene which is integrated into a non-native locus prior to introduction of a targeted landing pad at the specific genomic site at which the open reading frame is located.

In certain embodiments, the method further comprises: (a) screening phenotypes of the recovered host cells to select host cells with a particular phenotype; and (b) determining the identity of a first component polynucleotide integrated in the exogenous landing pad in the host cell. In certain embodiments, each component polynucleotide comprises a unique barcode sequence, and the barcode sequence can be used to identify the first component polynucleotide integrated in the targeted landing pad. In certain embodiments, the targeted landing pad is present in the host cell's genome together with one or more standardized landing pads described in Section 5.2 above.

In certain embodiments, the method can be applied in titrating (e.g., downregulating or upregulating) an endogenous gene of interest with a library of first component polynucleotides comprising regulatory sequences (e.g., promoters). FIG. 7A illustrates a schematic diagram of a promoter swap landing pad building construct which can be used to integrate "a promoter swap landing pad" at the native locus of an open reading frame. Once integrated in the host cell's genome, the promoter swap landing pad allows integration of any promoter in a library, 5' to an open reading frame of interest.

Referring to FIG. 7A, the promoter swap landing pad building construct comprises an upstream landing pad homology sequence (ULP, shown as "UL") and a downstream landing pad linker sequence (DLPL, shown as "A") for homologous recombination of first component polynucleotides. The promoter swap landing pad building construct further comprises a nuclease target sequence (NTS, shown as "X") and a temporary promoter pACT1 positioned between the (ULP) and (DLPL). The promoter landing pad building construct further comprises an upstream sequences of the ORF ("US_ORF") and a portion of the ORF for homologously at 5' and 3' regions, respectively, for homologous recombination at the native locus of ORF. Once the promoter swap landing pad is integrated in the host cell's genome as shown at FIG. 7B, the temporary promoter pACT1 drives the expression of the open reading frame.

The promoter swap landing pad can be integrated at the desired genomic site using any suitable method. For example, as shown in FIG. 7A, a site-specific nuclease (e.g., CRISPR/Cas9) can be used to cleave the native promoter pORF for the open reading frame. Once the native promoter pORF is cleaved, the promoter swap landing pad building construct homologously recombines with the upstream sequence of the open reading frame (US_ORF) and the 5' region of the ORF via host cell-mediated homologous recombination. Such a host cell transformed with a promoter swap landing pad integrated at 5' of ORF is shown in FIG. 7B. This host cell can be used as a parent host cell to further integrate and screen first component polynucleotides comprising various regulatory sequences which can modify transcription of the ORF, its protein expression or stability.

Referring to FIG. 7C, the parent host cell with a promoter swap landing pad is contacted with a promoter library. The promoter library comprises first component polynucleotides comprising promoters of varying strengths as nucleic acids of interest. Each first component polynucleotide in the library comprises a different promoter (shown as a curved arrow) positioned between an upstream library sequence (UL) and a first linker sequence A. In certain embodiments, each first component polynucleotide in the library further comprises a barcode sequence and/or additional nuclease target sequence as shown in FIG. 3A. The parent host cell with the promoter swap landing pad can be contacted with a plasmid encoding the nuclease X-cutter (e.g., CphI) for cleaving the target nuclease sequence X in the promoter swap landing pad, which allows the first component polynucleotides to integrate at the promoter swap landing pad.

In FIG. 7D, schematic diagrams further illustrate picking of colonies of host cells transformed with a promoter library, and screening host cells with desired phenotypes. The genotypes of the colonies (i.e., promoter sequences) can be identified using any suitable methods. For example, if each of the first component polynucleotides comprises a barcode sequence, a barcode sequence associated with the first component polynucleotides can be used to genotype the recovered host cell. The standard primers that bind to regions adjacent to the barcode sequence can be used to generate amplicons comprising the barcode sequence. The amplicons can be sequenced using any suitable techniques such as next generation sequencing. In certain embodiments, the amplicons generated using the standard primers are of certain fragment sizes (e.g., between about 500 to about 700 base pairs) that obviate the need for fragmentation prior to next generation sequencing (e.g., via MiSeq system from Illumina).

The method of titrating an endogenous gene expression (e.g., an open reading frame at its native locus) shown in FIGS. 7A-7D is merely exemplary, and there are many other variations. For example, first component polynucleotides can comprise other functional elements, such as transcription regulator sequences, degron sequences, or a fusion partner sequence, which can result in modification of various cellular functions or phenotypes of genetically modified host cells.

In another aspect, a targeted landing pad can be engineered and positioned 3' to an open reading frame at a specific genomic site. Thus, also provided herein is a method for targeted integration of nucleic acids into a host cell's genome, the method comprising:

(a) contacting a host cell, the host cell comprising an exogenous landing pad integrated 3' to an open reading frame, wherein the exogenous landing pad comprises a nuclease target sequence (NTS) positioned between an upstream landing pad linker sequence (ULPL) and a downstream landing pad homology sequence (DLP), with:
  (i) one or more last component polynucleotides, each last component polynucleotide comprises, in a 5' to 3' orientation:
    (1) a last linker sequence;
    (2) a last nucleic acid of interest; and
    (3) a downstream library sequence (DL) capable of homologously recombining with the (DLP);
  (ii) a nuclease (N) capable of binding to (NTS) and cleaving a site within the exogenous landing pad,
(c) recovering a host cell generated from the contacted host cell,
wherein the (ULPL) is capable of homologously recombining with the last linker sequence of any of the one or more last component polynucleotides to integrate a last component polynucleotide from the one or more last component polynucleotides at the exogenous landing pad.

An exemplary embodiment of utilizing a targeted landing pad positioned 3' of an open reading frame is illustrated in FIGS. 7E to 7H. FIG. 7E illustrates a terminator swap landing pad building construct which comprises a nuclease target sequence (NTS, shown as "X") positioned between an upstream landing pad linker sequence (ULPL, shown as "A") and a downstream landing pad homology sequence (DLP, shown as "DL"). The terminator swap landing pad building construct further comprises a portion of an open reading frame ("ORF") at its 5' region and a downstream sequences of the ORF ("DS_ORF") at its 3' region. These sequences at the 5' and 3' regions can be used for host cell mediated homologous recombination of the terminator swap landing pad into the native locus of the ORF. In the embodiment shown in FIG. 7E, the terminator swap landing pad building construct further comprises a temporary terminator, tACT1 positioned between the (ULPL, shown as "A") and the (NTS, shown as "X"). A host cell is transformed with the terminator swap landing pad building construct and a nuclease which can target and cleave the native terminator of the ORF (shown as "tORF"). The resulting integrated terminator swap landing pad in the host cell's genome is shown in FIG. 7F. This parent host cell with a terminator swap landing pad integrated in the host cell's genome 3' to the ORF can be used to screen various libraries of last component polynucleotides with standard library linker sequences and downstream library sequences.

In certain embodiments, the terminator swap landing pad can be used to integrate a degron library as shown in FIG. 7G. In such embodiments, the 3' end of the open reading frame adjacent to the (ULPL, shown as "A") does not comprise a stop codon at a position noted as "*" in the terminator swap landing pad. In FIG. 7G, the degron library comprises four last component polynucleotides, wherein each last component polynucleotide comprises, in a 5' to 3' orientation: a last linker sequence (shown as "A"), a last nucleic acid of interest (a degron sequence fused to a terminator), and a downstream library sequence (DL). Each of the four last component polynucleotides comprises a different degron sequence (degron 1, degron 2, degron 3, and degron 4). When a parent host cell with an integrated terminator swap landing pad is transformed with a nuclease, which is capable of binding to the (NTS) and cleaving a site within the landing pad, any of the last component polynucleotides in the degron library can integrate at the landing pad. The degron sequence integrated at the landing pad is fused in frame to the ORF, and a fusion protein expressed from such a construct can modulate the degradation of the fusion protein. When it is desired to modulate the degradation rate or stability of the fusion protein, a degron library of last component polynucleotides can be screened using a terminator swap landing pad as shown in FIG. 7G.

In other embodiments, the terminator swap landing pad comprises a stop codon at the 3' end of the open reading frame. Such a terminator swap landing pad is useful in integrating a terminator library of last component polynucleotides. The terminator plays an important role in RNA processing and contributes to variability in RNA half-life, and ultimately gene-expression. In FIG. 7H, the terminator library comprises four component polynucleotides, wherein each last component polynucleotide comprises, in a 5' to 3' orientation: a last linker (shown as "A"), a last nucleic acid of interest (a terminator), and a downstream library sequence (DL). Each of the four component polynucleotide comprises a different terminator sequence (term 1, term 2, term 3, and term 4). When a parent host cell with an integrated terminator swap landing pad is transformed with a nuclease, capable of binding to the (NTS) and cleaving a site within the landing pad, any of the last component polynucleotides in the terminator library can integrate at the terminator swap landing pad. Screening a terminator library is particularly useful when it is desired to modify the RNA half-life and thus gene expression from the open reading frame.

In another aspect, provided herein is a method of combining a targeted integration of an exogenous donor nucleic acid into a targeted landing pad and a genomic locus independent integration of an exogenous donor nucleic acid into another landing pad. For example, a host cell comprises a targeted landing pad as described in relation to FIGS. 7A-7H and one or more secondary landing pads, wherein each secondary landing pad comprises a nuclease target sequence positioned between a secondary upper landing pad homology sequence and a secondary downstream landing pad homology sequence. In this embodiment, at least one of the secondary upper landing pad homology sequence and the secondary downstream landing pad homology sequence is different from the targeted landing homology sequences.

In certain embodiments, the targeted integration of exogenous donor nucleic acids into a targeted landing pad can be combined with random integration of exogenous donor nucleic acids into standardized landing pads (e.g., shown in FIG. 2A) to determine their combinatorial effects on phenotypes of a host cell. FIG. 8 illustrates such an example. In contrast to a targeted landing pad, a standard, exogenous landing pad at a neutral locus in the host cell's genome allows expression of an exogenous donor nucleic acid integrated therein without any context of the genomic site at which the landing pad is located. Therefore, an exogenous landing pad at a neutral locus is also referred to as a genomic locus independent integration landing pad.

In the embodiment illustrated in FIG. 8, the parent host cell comprises two different landing pads: a targeted landing pad at the ERG9 locus and a secondary landing pad which is a genomic locus independent integration landing pad. The targeted landing pad at the ERG9 locus allows integration of various promoters to titrate expression of the native ERG9 gene. The secondary landing pad at the intergenic region of the iALG1 locus is used to combinatorially combine various promoters with a farnesene synthase gene ("FS").

The native ERG 9 encodes a squalene synthase which catalyzes the first step of sterol biosynthesis in various organisms. The production of sterol is important in various cellular functions including cellular biomass production. However, the cellular biomass production needs to be balanced against the target molecule production in industrial microbes during fermentation. In the exemplary embodiment shown in FIG. 8, the biosynthetic pathway (e.g., mevalonate pathway) produces an intermediate (e.g., FPP or farnesyl diphosphate) which can be converted into a desired target molecule (e.g., farnesene) via farnesene synthase or into biomass via ERG9. To increase production of target molecules (e.g., farnesene), it is desired to decrease expression of ERG 9 and overexpress the farnesene synthase gene.

To achieve an optimal balance for expression of ERG9 and farnesene synthase, the expression of two genes can be titrated simultaneously in a host cell using different sets of promoter libraries as shown in FIG. 8. A library of relatively weak pSNL1 promoters can be integrated into the targeted promoter swap landing pad at the ERG9 locus via homologous recombination of upstream landing pad homology sequence (ULP, shown as "UL$_1$") and an upstream library sequence (UL$_1$) of the pSLN1 library. A library of relatively strong pGAL promoters can be integrated at the secondary landing pad via homologous recombination of upstream landing pad homology sequence (ULP, shown as "UL") and an upstream library sequence (UL) of the pGAL library. The host cells simultaneously transformed with these two sets of promoter libraries can be screened to identify strains with the optimal production of target molecules which is balanced against the need for cellular biomass production. In certain embodiments, the promoters integrated in the optimal strains can be identified using barcode sequences associated with each promoter in component polynucleotides.

In another aspect, provided herein is a method of utilizing standardized landing pads in the host cell's genome for targeted integration of exogenous donor nucleic acids. In some instances, instead of creating a targeted landing pad, the targeted integration of specific genes can be achieved using endogenous genomic sequences adjacent to landing pad homology sequences. Thus, provided here is a method of targeted integration of exogenous donor nucleic acids into the host cell's genome comprises:
  (a) contacting a host cell, the host cell comprising one or more (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), wherein each landing pad is nested within an upper endogenous genomic sequence (UEG)$_x$ and a downstream endogenous genomic sequence (DEG)$_x$, with:
    (i) a nuclease capable of cleaving (NTS) in the one or more (x) exogenous landing pads; and
    (ii) one or more first component polynucleotides, wherein each first component polynucleotide comprises, in a 5' to 3' orientation:
      (1) an upstream library sequence (UL) capable of homologously recombining with any (ULP) of any of the one or more exogenous landing pads;
      (2) a first nucleic acid of interest;
      (3) a first linker sequence; and
    (iii) one or more last component polynucleotides, wherein each last component polynucleotide comprises, in a 5' to 3' orientation:
      (1) a last linker sequence;
      (2) a last nucleic acid of interest; and
      (3) a downstream library sequence (DL) capable of homologously recombining with (DEG)$_x$ of the one or more (x) exogenous landing pads,
  (b) recovering a host cell generated from the contacted cell,
wherein any combination of a first component polynucleotide from the one or more first component polynucleotides and a last component polynucleotide from the one or more last component polynucleotides, which are homologously recombined in vivo via their linker sequences, is integrated at an exogenous landing pad with (DEG)$_x$, and x is an integer of at least one.

An exemplary embodiment is illustrated in FIG. 9. The parent host cell shown in FIG. 9 comprises two landing pads. The first and second landing pads are both standardized landing pad comprising a nuclease target sequence (X) positioned between an upstream landing pad homology sequence (UL) and a downstream landing pad homology sequence (DL). The two landing pads are engineered into intergenic regions downstream of the ALG1 locus and the YCT1 locus, respectively, in the parent host cell. For targeted integration of exogenous donor nucleic acids, the parent strain is contacted with the following: 1) a nuclease that cleaves nuclease target sequence X; 2) a promoter library comprising various promoters (i.e., 9 first component polynucleotides comprising promoters of varying promoter strengths); 3) a last component polynucleotide comprising ORF1 which is configured to always integrate at landing pad 1; and 2) a last component polynucleotide comprising ORF2 which is configured to always integrate at landing pad 2. The last component polynucleotide comprising ORF1 always integrates at landing pad 1 because it comprises a downstream library sequence which is identical to a downstream endogenous genomic sequence (DEG) of the iALG1 locus. The last component polynucleotide comprising ORF2 always integrates at landing pad 2, because it comprises a downstream library sequence which is identical to the downstream endogenous genomic sequence (DEG) of the iYCT1 locus. The exogenous donor nucleic acids comprising these ORFs are combinatorially combined and integrated with any of the first component polynucleotides comprising a promoter. The host cells transformed with the ORF1 and ORF2 operably linked to various promoters can be screened to determine the optimally balanced co-expression of these ORFs by selecting host cells with a desired phenotype. In certain embodiments, the selected host cells with a desired phenotype can be genotyped using barcode sequences associated with each component polynucleotide.

In another aspect, the method of targeted integration of exogenous donor nucleic acids into the host cell's genome utilizes an upstream endogenous genomic sequence (UEG) for homologous recombination of a library of first component polynucleotides which comprise (UEG) as upstream library sequences for homologous recombination. The method comprises:
(a) contacting a host cell, the host cell comprising one or more (x) exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), wherein each landing pad is nested within an upper endogenous genomic sequence $(UEG)_x$ and a downstream endogenous genomic sequence $(DEG)_x$, with:
(i) a nuclease capable of cleaving (NTS) in the one or more (x) exogenous landing pads; and
(ii) one or more first component polynucleotides, wherein each first component polynucleotide comprises, in a 5' to 3' orientation:
(1) an upstream library sequence (UL) capable of homologously recombining with $(UEG)_x$ of the one or more (x) exogenous landing pads;
(2) a first nucleic acid of interest;
(3) a first linker sequence; and
(iii) one or more last component polynucleotides, wherein each last component polynucleotide comprises, in a 5' to 3' orientation:
(1) a last linker sequence;
(2) a last nucleic acid of interest; and
(3) a downstream library sequence (DL) capable of homologously recombining with any DLP of any of the one or more (x) exogenous landing pads,
(b) recovering a host cell generated from the contacted host cell,
wherein any combination of a first component polynucleotide from the one or more first component polynucleotides and a last component polynucleotide from the one or more last component polynucleotides, which are homologously recombined in vivo via their linker sequences, is integrated at an exogenous landing pad with $(UEG)_x$, and x is an integer of at least one.

6.5 Methods for Metabolic Pathway Engineering

The methods and compositions described herein provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of precursors to the antimalarial drug artemisinin (see, e.g., Martin et al., *Nat Biotechnol* 21:796-802 (2003); fatty acid derives fuels and chemicals (e.g., fatty esters, fatty alcohols and waxes; see, e.g., Steen et al., *Nature* 463:559-562 (2010); methyl halide-derived fuels and chemicals (see, e.g., Bayer et al., *J Am Chem Soc* 131:6508-6515 (2009); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004).

Traditionally, metabolic engineering, and in particular, the construction of biosynthetic pathways or optimizing the metabolic flux through the biosynthetic pathways, has proceeded in a one-at-a-time serial fashion whereby pathway components have been introduced, i.e., integrated into the host cell's genome at a single loci at a time. The methods of integration provided herein can be utilized to reduce the time typically required to engineer a host cell, for example, a microbial cell, to comprise one or more heterologous nucleotide sequences encoding enzymes of a new metabolic pathway, i.e., a metabolic pathway that produces a metabolite that is not endogenously produced by the host cell. In other particular embodiments, the methods of integration provided herein can be used to efficiently engineer a host cell to comprise one or more heterologous nucleotide sequences encoding enzymes of a metabolic pathway that is endogenous to the host cell, i.e., a metabolic pathway that produces a metabolite that is endogenously produced by the host cell. In other particular embodiments, the methods of integration provided herein can be used to optimize metabolic flux through and achieve high product titers by balancing expression of two or more heterologous nucleotide sequences encoding enzymes of a metabolic pathway that produces a product. For example, as described above in relation to FIG. 8, by utilizing a promoter library with standardized homology sequences, the metabolic flux can be optimized to balance production of biomass and a final product of interest. Moreover, the methods enable the porting of DNA assemblies, comprising optimized pathway components integrated at multiple landing pads in one host cell chassis, to analogous landing pads in a second host cell chassis. By reducing the number of rounds needed to engineer a desired genotype, the pace of construction of optimizing the metabolic pathways is substantially increased.

6.5.1. Isoprenoid Pathway Engineering

In some embodiments, the methods provided herein can be utilized to simultaneously introduce, replace, or titrate one or more components of a biosynthetic pathway to modify the product profile of an engineered host cell. In some embodiments, the biosynthetic pathway is the isoprenoid pathway.

Terpenes are a large class of hydrocarbons that are produced in many organisms. When terpenes are chemically modified (e.g., via oxidation or rearrangement of the carbon skeleton) the resulting compounds are generally referred to as terpenoids, which are also known as isoprenoids. Isoprenoids play many important biological roles, for example, as quinones in electron transport chains, as components of membranes, in subcellular targeting and regulation via protein prenylation, as photosynthetic pigments including carotenoids, chlorophyll, as hormones and cofactors, and as plant defense compounds with various monoterpenes, sesquiterpenes, and diterpenes. They are industrially useful as antibiotics, hormones, anticancer drugs, insecticides, and chemicals.

Terpenes are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are geraniol, limonene, and terpineol. Sesquiterpenes are composed of three isoprene units, and have the molecular formula $C_{15}H_{24}$. Examples of sesquiterpenes are farnesenes and farnesol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpenes is geranyl-farnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

Terpenes are biosynthesized through condensations of isopentenyl pyrophosphate (isopentenyl diphosphate or IPP) and its isomer dimethylallyl pyrophosphate (dimethylallyl diphosphate or DMAPP). Two pathways are known to generate IPP and DMAPP, namely the mevalonate-dependent (MEV) pathway of eukaryotes (FIG. 13), and the mevalonate-independent or deoxyxylulose-5-phosphate (DXP) pathway of prokaryotes. Plants use both the MEV pathway and the DXP pathway. IPP and DMAPP in turn are condensed to polyprenyl diphosphates (e.g., geranyl disphosphate or GPP, farnesyl diphosphate or FPP, and geranylgeranyl diphosphate or GGPP) through the action of prenyl disphosphate synthases (e.g., GPP synthase, FPP synthase, and GGPP synthase, respectively). The polyprenyl diphosphate intermediates are converted to more complex isoprenoid structures by terpene synthases.

Terpene synthases are organized into large gene families that form multiple products. Examples of terpene synthases include monoterpene synthases, which convert GPP into monoterpenes; diterpene synthases, which convert GGPP into diterpenes; and sesquiterpene synthases, which convert FPP into sesquiterpenes. An example of a sesquiterpene synthase is farnesene synthase, which converts FPP to farnesene. Terpene synthases are important in the regulation of pathway flux to an isoprenoid because they operate at metabolic branch points and dictate the type of isoprenoid produced by the cell. Moreover, the terpene synthases hold the key to high yield production of such terpenes. As such, one strategy to improve pathway flux in hosts engineered for heterologous isoprenoid production is to introduce multiple copies of nucleic acids encoding terpene synthases. For example, in engineered microbes comprising the MEV pathway where the production of sesquiterpenes such as farnesene is desired, a sesquiterpene synthase, e.g., a farnesene synthase is utilized as the terminal enzyme of the pathway, and multiple copies of farnesene synthase genes may be introduced into the host cell towards the generation of a strain optimized for farnesene production.

Because the biosynthesis of any isoprenoid relies on the same pathway components upstream of the prenyl disphosphate synthase and terpene synthase, these pathway components, once engineered into a host "platform" strain, can be utilized towards the production of any sesquiterpene, and the identity of the sesquiterpene can be dictated by the particular sesquiterpene synthase introduced into the host cell. Moreover, where production of terpenes having different isoprene units is desired, for example a monoterpene instead of a sesquiterpene, both the prenyl diphosphate synthase and the terpene synthase can be replaced to produce the different terpene while still utilizing the upstream components of the pathway.

Accordingly, the methods and compositions provided herein can be utilized to efficiently modify a host cell comprising an isoprenoid producing pathway, e.g., the MEV pathway to produce a desired isoprenoid and/or an enhanced level of isoprenoid production. In some embodiments, the host cell comprises the MEV pathway, and the methods of simultaneous multiple integration provided herein can be utilized to simultaneously introduce multiple copies of a prenyl diphosphate synthase and/or a terpene synthase to define the terpene product profile of the host cell. In some embodiments, the prenyl diphosphate synthase is GPP synthase and the terpene synthase is a monoterpene synthase. In some embodiments, the prenyl diphosphate synthase is FPP synthase and the terpene synthase is a sesquiterpene synthase. In some embodiments, the prenyl diphosphate synthase is GGPP synthase and the terpene synthase is a diterpene synthase. In other embodiments, the host cell comprises the MEV pathway and a prenyl diphosphate synthase and/or a terpene synthase for the production of a first type of terpene, for example, farnesene, and the methods of simultaneous multiple integration provided herein can be utilized to simultaneously replace one or more copies of the prenyl diphosphate synthase and/or a terpene synthase to produce a second type of terpene, for example, amorphadiene. The methods provided herein can be similarly utilized towards the construction and/or modification of any biosynthetic pathway which utilizes multiple copies of pathway components, and are particularly useful for engineering host cells whose product profile can be readily modified with the addition or exchange of multiple copies of a single pathway component.

6.5.2. Methods of Generating Combinatorial Integration Libraries for Biosynthetic Pathways Once biosynthetic pathways are constructed, the expression levels of all the components need to be orchestrated to optimize metabolic flux and achieve high product titers. Common approaches for optimizing flux include varying the identity of the pathway component gene, the codon optimization of the gene, the use of solubility tags, the use of truncations or known mutations, and the expression context of the gene (i.e. promoter and terminator choice). To sample this variability in the course of building a strain using traditional methods requires generating and archiving an impractically large number of strains. For example, if a strain engineer plans to integrate constructs at three loci, and has devised 10 variants for each locus, 1,000 strains would need to be generated to fully sample the combinatorial diversity. Since pathway genes work in concert, and not all metabolite intermediates can easily be screened for, it is often impossible to evaluate the individual contribution of the pathway genes after each integration cycle. Thus, strain engineers routinely make choices that severely limit the design space that they sample when constructing a novel metabolic pathway.

To better identify the optimal pathway design, the methods of genomic modification provided herein can be utilized to generate strains comprising combinatorial libraries of exogenous donor nucleic acids. In some embodiments, the methods rely on contacting the host cell's genome with one or more nucleases and one or more donor DNA assemblies (e.g., component polynucleotides) to facilitate multiple simultaneous integration of donor DNA at standardized landing pads in the genome. To generate a diversity of engineered strains, the methods comprise co-transforming a library of donor DNAs, i.e., a mixture of integration constructs for one or more standardized landing pads and/or targeted landing pads, such that combinatorial integration libraries of host strains can be generated. The high frequency of multiple integrations achieved means that the resultant strains can reasonably be screened directly for product without extensive genomic quality control, and the identity of top strains can be determined after screening, for example, by sequencing. This method removes the burden of individual strain generation, quality control and archiving, and allows the engineer to generate diverse integration combinations in a single tube, and sort out the best performing strains by screening, e.g., for the terminal product of the pathway.

Thus, in some embodiments, the methods for integrating a plurality of exogenous nucleic acids into a host cell's genome provided herein comprise contacting a host cell comprising one or more landing pads described herein with a plurality of libraries, wherein each library (L) comprises a plurality of exogenous nucleic acids, wherein a selected exogenous nucleic acid comprises, in a 5' to 3' orientation, an upstream library sequence (UL), any nucleic acid of interest selected from the group (D), and a downstream library sequence (DL), wherein (UL) and (DL) are capable of initiating host cell mediated homologous recombination the selected exogenous nucleic acid at the one or more landing pads in a host cell's genome; and a nuclease (N) capable of cleaving at (NTS), whereupon said cleaving results in homologous recombination of the landing pads.

In some embodiments, each library (L) comprises exogenous nucleic acids encoding enzymes of a common biosynthetic pathway. In some embodiments, the group (D) comprises at least $10^1$, $10^2$, $10^3$, $10^4$, $10^5$, $10^6$, or more than $10^6$ unique nucleic acids of interest. In some embodiments, each library (L) comprises a plurality of exogenous nucleic acids encoding variants of an enzyme of a biosynthetic pathway. As used herein, the term "variant" refers to an enzyme of a biosynthetic pathway that compared to a selected enzyme has a different nucleotide or amino acid sequence. For example, in some embodiments, a library (L) comprises sesquiterpene synthase variants, and compared to the wild-type version of the selected sesquiterpene synthase, the sesquiterpene synthase variant may comprise nucleotide additions, deletions, and/or substitutions that may or may not result in changes to the corresponding amino acid sequence. In other embodiments, the enzyme variant comprises amino acid additions, deletions and/or substitutions relative to a reference enzyme, e.g., the wild-type version.

In some embodiments, the host cell comprises one or more heterologous nucleotide sequences encoding one or more enzymes of a biosynthetic pathway prior to said contacting. In some embodiments, the one or more heterologous nucleotide sequences encoding one or more enzymes of a biosynthetic pathway are genomically integrated into the landing pads.

6.6 Nucleases

In some embodiments of the methods described herein, a host cell's genome is contacted with one or more nucleases capable of cleaving, i.e., causing a double-stranded break at or nearby the nuclease target sequence (NTS) in a landing pad. In some embodiments, a double-strand break inducing agent is any agent that recognizes and/or binds to a specific polynucleotide recognition sequence to produce a break at or near the recognition sequence. Examples of double-strand break inducing agents include, but are not limited to, endonucleases, site-specific recombinases, transposases, topoisomerases, and zinc finger nucleases, and include modified derivatives, variants, and fragments thereof.

In some embodiments of the methods described herein, a host cell's genome is contacted with one or more nucleases capable of cleaving, i.e., causing a break at a designated region within a landing pad. In some embodiments, the break is a single-stranded break, that is, one but not both DNA strands of the nuclease target sequence are cleaved (i.e., "nicked"). In some embodiments, the break is a double-stranded break. In some embodiments, a break inducing agent is any agent that recognizes and/or binds to a specific polynucleotide recognition sequence to produce a break at or near the recognition sequence. Examples of break inducing agents include, but are not limited to, endonucleases, site-specific recombinases, transposases, topoisomerases, and zinc finger nucleases, and include modified derivatives, variants, and fragments thereof.

In some embodiments, each of the one or more nucleases is capable of causing a break at a designated region within a selected nuclease target sequence (NTS). In some embodiments, the nuclease is capable of causing a break at a region positioned between the 5' and 3' regions of (NTS) in a landing pad. In other embodiments, the nuclease is capable of causing a break at a region positioned upstream or downstream of the 5' and 3' regions of (NTS).

A nuclease target sequence (NTS) comprises a recognition sequence, which is any polynucleotide sequence that is specifically recognized and/or bound by a break inducing agent. The length of the recognition site sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

In some embodiments, the recognition sequence within the landing pad can be endogenous or exogenous to the host cell's genome. When the recognition site is an endogenous sequence, it may be a recognition sequence recognized by a naturally-occurring, or native break inducing agent. Alternatively, an endogenous recognition site could be recognized and/or bound by a modified or engineered break inducing agent designed or selected to specifically recognize the endogenous recognition sequence to produce a break. In some embodiments, the modified break inducing agent is derived from a native, naturally-occurring break inducing agent. In other embodiments, the modified break inducing agent is artificially created or synthesized. Methods for selecting such modified or engineered break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci USA* 82:488-92; Kunkel, et al., (1987) *Meth Enzymol* 154:367-82; U.S. Pat. No. 4,873,192; Walker and Gaastra, eds. (1983) Techniques in Molecular Biology (MacMillan Publishing Company, New York) and the references cited therein. Guidance regarding amino acid substitutions not likely to affect biological activity of the protein is found, for example, in the model of Dayhoff, et al., (1978) Atlas of Protein Sequence and Structure (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

6.6.1. Clustered Regulatory Interspaced Short Palindromic Repeats (CRISPR)

In some embodiments of the methods provided herein, the nuclease is a CRISPR/Cas-derived RNA-guided endonuclease. CRISPR is a genome editing tool based on the type II prokaryotic CRISPR (clustered regularly interspersed short palindromic repeats) adaptive immune system. CRISPR systems in eubacteria and archaea use small RNAs and CRISPR-associated (Cas) endonucleases to target and cleave invading foreign DNAs. See, e.g., Bhaya et al., *Annu Rev Genet* 45:273-297 (2011); Terns et al., *Curr Opin Microbiol* 14(3):321-327 (2011); and Wiedenheft et al., *Nature* 482 (7385):331-338. In bacteria, CRISPR loci are composed of a series of repeats separated by segments of exogenous DNA (of ~30 bp in length) called spacers. The repeat-spacer array is transcribed as a long precursor and processed within repeat sequences to generate small crRNAs that specify the target sequences (also known as protospacers) cleaved by the CRISPR nuclease. CRISPR spacers are then used to recognize and silence exogenous genetic elements at the RNA or DNA level. Essential for cleavage is a sequence motif immediately downstream on the 3' end of the target region, known as the protospacer-adjacent motif (PAM). The PAM is present in the target DNA, but not the crRNA that targets it.

One of the simplest CRISPR systems is the type II CRISPR system from *Streptococcus* pyognes. The CRISPR-associated Cas9 endonuclease and two small RNAs, a target-complimentary CRISPR RNA (crRNA); and a transacting crRNA (tracrRNA), are sufficient for RNA-guided cleavage of foreign DNAs. The Cas9 protein, a hallmark protein of the type II CRISPR-Cas system, is a large monomeric DNA nuclease containing two nuclease domains homologous to RuvC and HNH nucleases. Cas9 is guided to a DNA target sequence adjacent to the PAM (protospacer adjacent motif) sequence motif by a crRNA:tracrRNA complex. Mature crRNA base-pairs to tracrRNA to form a two-RNA structure that directs Cas9 to the target DNA. At sites complementary to the crRNA-guide sequence, the Cas9 HNH nuclease domain cleaves the complementary strand, whereas the Cas9 RuvC-like domain cleaves the noncomplementary strand, resulting in a double strand break in the target DNA. See, e.g., Deltcheva et al., Nature 47(7340):602-607 (2011).

Recent studies show that a single guide RNA (gRNA) chimera that mimics the crRNA:tracrRNA complex can be utilized with Cas9 as a genome editing tool to guide Cas9 to introduce site specific DNA double-stranded breaks in vitro. Specificity of the cleavage within the target genome is determined by the spacer-like moiety of a chimeric guide RNA molecule (gRNA), which mimics the native crRNA: tracrRNA complex. Thus, the minimum number of components in a functional CRISPR/Cas system is two: Cas9 and sgRNA. The sgRNA guide sequence located at its 5' end confers DNA target specificity. Therefore, by modifying the guide sequence, it is possible to create sgRNAs with different target specificities. The canonical length of the guide sequence is 20 bp. Consequently, a DNA target is also 20 bp followed by a PAM sequence that follows the consensus NGG. Use of this modified CRISPR system has been demonstrated in vitro (see, e.g., Jinek et al., *Science* 337 (6096):816-821 (2012)), in mammalian cell lines (see, e.g., Mali et al., *Science* 339(6121):823-826 (2013), Jinek et al., *Elife* 2:e00417 (2013); Cong et al., *Science* 339(6121):819-823 (2013); and Cho et al., *Nat Biotechnol* 31(3):230-232 (2013)), in bacteria (see, e.g., Jiang et al., *Nat Biotechnol* 31(3):233-239 (2013); and Gasiunas et al., *Proc Natl Acad Sci USA* 109(39):E2579-E2586. (2012)), yeast (see, e.g., DiCarlo et al., *Nucleic Acid Res* 41(7):4336-4343 (2013)), zebrafish (see, e.g., Hwang et al., *Nat Biotechnol* 31(3):227-229 (2013); and Chang et al., *Cell Res* 23(4):465-472 (2013)), mice (see, e.g., Wang et al., Cell 153(4):910-918 (2013), and plants (see e.g., Belhaj et al., *Plant Methods* 9:39 (2013)).

The Cas9 nuclease may be modified by: (1) codon optimization for increased expression within a heterologous host; (2) fusion to a nuclear localization signal (NLS) for proper compartmentalization; and (3) site directed mutagenesis of either the HNH or RuvC domain to convert the nuclease into a strand-specific nickase. Site-directed mutagenesis of Cas9 in either the RuvC- or HNH-motif showed strand cleavage specificity, thereby providing two strand-specific nickases, in addition to the wild-type endonuclease and enabling targeted single-strand breaks of DNA. See, e.g., Jinek et al., *Science* 337(6096):816-821 (2012), and Gasiunas et al., *Proc Natl Acad Sci USA* 109(39):E2579-E2586. (2012). As has been reported for zinc finger nucleases and TALENs, modifying the nuclease to function as a nickase that breaks only one strand reduces toxicity from off-target cutting, and may also lower rates of break repair via non-HR mechanisms, e.g., NHEJ. See, e.g., Jinek et al., *Science* 337(6096):816-821 (2012).

Any CRISPR/Cas system known in the art finds use as a nuclease in the methods and compositions provided herein. The highly diverse CRISPR-Cas systems are categorized into three major types, which are further subdivided into ten subtypes, based on core element content and sequences (see, e.g., Makarova et al., *Nat Rev Microbiol* 9:467-77 (2011)). The structural organization and function of nucleoprotein complexes involved in crRNA-mediated silencing of foreign nucleic acids differ between distinct CRISPR/Cas types (see Wiedenheft et al., *Nature* 482:331-338 (2012)). In the Type 1-E system, as exemplified by *Escherichia coli*, crRNAs are incorporated into a multisubunit effector complex called Cascade (CRISPR-associated complex for antiviral defence) (Brouns et al., *Science* 321: 960-4 (2008)), which binds to the target DNA and triggers degradation by the signature Cas3 protein (Sinkunas et al., *EMBO J* 30:1335ˆ2 (2011); Beloglazova et al., *EMBO J*30:616-27 (2011)). In Type III CRISPR/Cas systems of *Sulfolobus solfataricus* and *Pyrococcus furiosus*, Cas RAMP module (Cmr) and crRNA complex recognize and cleave synthetic RNA in vitro (Hale et al., *Mol Cell* 45:292-302 (2012); Zhang et al., *Mol Cell*, 45:303-13 (2012)), while the CRISPR/Cas system of *Staphylococcus epidermidis* targets DNA in vivo (Marraffini & Sontheimer, *Science.* 322:1843-5 (2008)). RNP complexes involved in DNA silencing by Type II CRISPR/Cas systems, more specifically in the CRISPR3/Cas system of *Streptococcus thermophilus* DGCC7710 (Horvath & Barrangou, *Science* 327:167-70 (2010)), consists of four cas genes: cas9, cas1, cas2, and csn2, that are located upstream of 12 repeat-spacer units. Cas9 (formerly named cas5 or csn1) is the signature gene for Type II systems (Makarova et al., *Nat Rev Microbiol* 9:467-77 (2011)).

CRISPR systems that find use in the methods and compositions provided herein also include those described in International Publication Numbers WO 2013/142578 A1 and WO 2013/098244 A1, the contents of which are hereby incorporated in their entireties.

6.6.2. Transcription Activator-Like Effector Nucleases (TALENs)

In some embodiments of the methods provided herein, one or more of the nucleases is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318: 645-8; Boch et al., (2009) *Science* 326(5959):1509-12; and Moscou and Bogdanove, (2009) 326(5959):1501. A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain may be engineered to bind to a desired target sequence, and fused to a nuclease domain, e.g., from a type II restriction endonuclease, typically a nonspecific cleavage domain from a type II restriction endonuclease such as FokI (see. e.g., Kim et al. (1996) *Proc. Natl. Acad. Sci. USA* 93:1156-1160). Other useful endonucleases may include, for example, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940.

In some embodiments, the TAL effector domain that binds to a specific nucleotide sequence within the target DNA can comprise 10 or more DNA binding repeats, and preferably 15 or more DNA binding repeats. In some embodiments, each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T. In some embodiments of the methods provided herein, one or more of the nucleases is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. For reviews of site-specific recombinases and their recognition sites, see, Sauer (1994) *Curr Op Biotechnol* 5:521-7; and Sadowski, (1993) *FASEB* 7:760-7. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R. For other members of the Integrase family, see for example, Esposito, et al., (1997) *Nucleic Acids Res* 25:3605-14 and Abremski, et al., (1992) *Protein Eng* 5:87-91. Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc Natl Acad Sci USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J* 7:3983-9; Arnold, et al., (1999) *EMBO J* 18:1407-14; WO03/08045; WO99/25840; and WO99/25841. The recognition sites range from about 30 nucleotide minimal sites to a few hundred nucleotides. Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan, et al., (2001)*Mol Cell* Biol 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

In some embodiments of the methods provided herein, one or more of the nucleases is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Tal elements from *Arabidopsis* (retrotransposon), the P element transposon from *Drosophila* (Gloor, et al., (1991) *Science* 253: 1110-1117), the Copia, Mariner and Minos elements from *Drosophila*, the Hermes elements from the housefly, the PiggyBack elements from Trichplusia ni, Tc1 elements from C. elegans, and IAP elements from mice (retrotransposon).

6.6.3. Zinc Finger Nucleases (ZFNs)

In some embodiments of the methods provided herein, one or more of the nucleases is a zinc-finger nuclease (ZFN). ZFNs are engineered break inducing agents comprised of a zinc finger DNA binding domain and a break inducing agent domain. Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two FokI nuclease monomers, ZFNs generate a functional site-specific endonuclease that creates a break in DNA at the targeted locus.

Useful zinc-finger nucleases include those that are known and those that are engineered to have specificity for one or more nuclease target sequences (NTS) described herein. Zinc finger domains are amenable for designing polypeptides which specifically bind a selected polynucleotide recognition sequence, for example, within the target site of the host cell's genome. ZFNs consist of an engineered DNA-binding zinc finger domain linked to a non-specific endonuclease domain, for example nuclease domain from a Type IIs endonuclease such as HO or FokI. Alternatively, engineered zinc finger DNA binding domains can be fused to other break inducing agents or derivatives thereof that retain DNA nicking/cleaving activity. For example, this type of fusion can be used to direct the break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), as well as those that recognize various CNN or TNN triplets (Dreier, et al., (2005) *J Biol Chem* 280:35588-97; Jamieson, et al., (2003) *Nature Rev Drug Discov* 2:361-8). See also, Durai, et al., (2005) *Nucleic Acids Res* 33:5978-90; Segal, (2002) *Methods* 26:76-83; Porteus and Carroll, (2005) *Nat Biotechnol* 23:967-73; Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc Natl Acad Sci USA* 99:13290-5; Guan, et al., (2002) *Proc Nat Acad Sci USA* 99:13296-301; WO2002099084; WO00/42219; WO02/42459; WO2003062455; US20030059767; US patent application publication number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

6.6.4. Endonucleases

In some embodiments of the methods provided herein, one or more of the nucleases is an endonuclease. Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. Restriction endonucleases are further described and classified, for example in the REBASE database (webpage at rebase.neb.com; Roberts, et al., (2003) *Nucleic Acids Res* 31:418-20), Roberts, et al., (2003) *Nucleic Acids Res* 31:1805-12, and Belfort, et al., (2002) in Mobile DNA II, pp. 761-783, Eds. Craigie, et al., ASM Press, Washington, D.C.

As used herein, endonucleases also include homing endonucleases, which like restriction endonucleases, bind and cut at a specific recognition sequence. However the recognition sites for homing endonucleases are typically longer, for example, about 18 bp or more. Homing endonucleases, also known as meganucleases, have been classified into the following families based on conserved sequence motifs: an LAGLIDADG (SEQ ID NO:1) homing endonuclease, an HNH homing endonuclease, a His-Cys box homing endonuclease, a GIY-YIG (SEQ ID NO:2) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. See, for example, Guhan and Muniyappa (2003) *Crit Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), I-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., S. *Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., Dokl. Biochem. 339: 145-147 (1994); Kaliman, *Nucleic Acids Res.* 18: 4277 (1990), F-CphI (see, Zeng et al., Curr. Biol. 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments of the methods described herein, a naturally occurring variant, and/or engineered derivative of a homing endonuclease is used. Methods for modifying the kinetics, cofactor interactions, expression, optimal conditions, and/or recognition site specificity, and screening for activity are known. See, for example, Epinat, et al., (2003) *Nucleic Acids Res* 31:2952-62; Chevalier, et al., (2002)*Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Biol* 342:31-41; Rosen, et al., (2006) *Nucleic Acids Res* 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346. Useful homing endonucleases also include those described in WO04/067736; WO04/067753; WO06/097784; WO06/097853; WO06/097854; WO07/034262; WO07/049095; WO07/049156; WO07/057781; WO07/060495; WO08/152524; WO09/001159; WO09/095742; WO09/095793; WO10/001189; WO10/015899; and WO10/046786.

Any homing endonuclease can be used as a double-strand break inducing agent including, but not limited to: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof.

In some embodiments, the endonuclease binds a native or endogenous recognition sequence. In other embodiments, the endonuclease is a modified endonuclease that binds a non-native or exogenous recognition sequence and does not bind a native or endogenous recognition sequence.

6.6.5. Nuclease Target Sequence in a Landing Pad

In the methods provided herein, a nuclease is introduced to the host cell that is capable of causing a double-strand break near or within a nuclease target sequence in a landing pad, which greatly increases the frequency of homologous recombination at or near the cleavage site. In preferred embodiments, the nuclease target sequence (NTS) comprising a recognition sequence for the nuclease is present in the host cell's genome only at the landing pad(s), thereby minimizing any off-target genomic binding and cleavage by the nuclease.

If the nuclease to be utilized is a CRISPR/Cas-derived RNA-guided endonuclease, optimal nuclease target sequence may be selected in accordance with the requirements for target recognition of the particular CRISPR-Cas endonuclease being used. For example Cas9 target recognition occurs upon detection of complementarity between a "protospacer" sequence in the target DNA and the remaining spacer sequence in the crRNA. Cas9 cuts the DNA only if a correct protospacer-adjacent motif (PAM) is also present at the 3' end. Different Type II systems have differing PAM requirements. The *S. pyogenes* system requires an NGG sequence, where N can be any nucleotide. *S. thermophilus* Type II systems require NGGNG and NNAGAAW, respectively, while different *S. mutans* systems tolerate NGG or NAAR. Bioinformatic analyses have generated extensive databases of CRISPR loci in a variety of bacteria that may serve to identify new PAMs and expand the set of CRISPR-targetable sequences. See, e.g., Rho et al., *PLoS Genet.* 8, e1002441 (2012); and D. T. Pride et al., Genome Res. 21, 126 (2011). In *S. thermophilus*, Cas9 generates a blunt-ended double-stranded break 3 bp upstream of the protospacer, a process mediated by two catalytic domains in the Cas9 protein: an HNH domain that cleaves the complementary strand of the DNA and a RuvC-like domain that cleaves the non-complementary strand.

If the nuclease to be utilized is a zinc finger nuclease, optimal nuclease target sequence may be selected using a number of publicly available online resources. See, e.g., Reyon et al., *BMC Genomics* 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *S. cerevisiae. C. reinhardtii. A. thaliana. D. melanogaster. D. rerio. C. elegans*, and *H. sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) will be added in the near future. ZFNGenome provides information about each potential ZFN target site, including its chromosomal location and position relative to transcription initiation site(s). Users can query ZFNGenome using several different criteria (e.g., gene ID, transcript ID, target site sequence).

If the nuclease to be utilized is a TAL-effector nuclease, in some embodiments, optimal nuclease target sequence may be selected in accordance with the methods described by Sanjana et al., *Nature Protocols,* 7:171-192 (2012), which is hereby incorporated by reference in its entirety. In brief, TALENs function as dimers, and a pair of TALENs, referred to as the left and right TALENs, target sequences on opposite strands of DNA. TALENs are engineered as a fusion of the TALEN DNA-binding domain and a monomeric FokI catalytic domain. To facilitate FokI dimerization, the left and right TALEN target sites are chosen with a spacing of approximately 14-20 bases. Therefore, for a pair of TALENs, each targeting 20-bp sequences, an optimal target site should have the form 5'-TN19N14-20N19A-3', where the left TALEN targets 5'-TN19-3' and the right TALEN targets the antisense strand of 5'-N19A-3' (N=A, G, T or C).

In other embodiments of the methods provided herein, the nuclease target sequence is exogenous to the host cell. In some embodiments, multiple copies of the same nuclease target sequence are engineered into the landing pads, thereby facilitating simultaneous multiple integration events with the use of only a single nuclease that specifically recognizes the nuclease target sequence. In other embodiments, a plurality of different nuclease target sequences is engineered into the host cell's genome at different landing pads. In some embodiments, the engineered landing pads comprise a target nuclease sequence that is not otherwise represented in the native genome of the host cell. For example, homing endonucleases target large recognition sites (12-40 bp) that are usually embedded in introns or inteins, and as such, their recognition sites are extremely rare, with none or only a few of these sites present in a mammalian-sized genome. Thus, in some embodiments, the exogenous nuclease target sequence is a recognition sequence for a homing endonuclease. In some embodiments, the homing nuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-*ChuI*, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof. In particular embodiments, the exogenous genomic nuclease target sequence is the recognition sequence for I-SceI, VDE (PI-SceI), F-CphI, PI-MgaI or PI-MtuII, each of which are provided below.

TABLE 1

Recognition and cleavage sites for select homing endonucleases.

| Nuclease | Recognition sequence |
| --- | --- |
| I-SceI | TAGGGATAACAGGGTAAT (SEQ ID NO: 3) |
| VDE (PI-SceI) | TATGTCGGGTGCGGAGAAAGAGGTAATGAAA (SEQ ID NO: 4) |
| F-CphI | GATGCACGAGCGCAACGCTCACAA (SEQ ID NO: 5) |

TABLE 1-continued

Recognition and cleavage sites for select homing endonucleases.

| Nuclease | Recognition sequence |
| --- | --- |
| PI-MgaI | GCGTAGCTGCCCAGTATGAGTCAG (SEQ ID NO: 6) |
| PI-MtuII | ACGTGCACTACGTAGAGGGTCGCACCGCACCGATCTACAA (SEQ ID NO: 7) |

6.6.6. Delivery

In some embodiments, the one or more nucleases useful for the methods described herein are provided, e.g., delivered into the host cell as a purified protein. In other embodiments, the one or more nucleases are provided via polynucleotide(s) comprising a nucleic acid encoding the nuclease. In other embodiments, the one or more nucleases are introduced into the host cell as purified RNA which can be directly translated in the host cell nucleus.

In certain embodiments, an integration polynucleotide, a polynucleotide encoding a nuclease, or a purified nuclease protein as described above, or any combination thereof, may be introduced into a host cell using any conventional technique to introduce exogenous protein and/or nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Particular methods for transforming cells are well known in the art. See Hinnen et al., *Proc. Natl. Acad. Sci. USA* 75:1292-3 (1978); Cregg et al., *Mol. Cell. Biol.* 5:3376-3385 (1985). Exemplary techniques include but are not limited to, spheroplasting, electroporation, PEG 1000 mediated transformation, and lithium acetate or lithium chloride mediated transformation.

In some embodiments, biolistics are utilized to introduce an integration polynucletide, a polynucleotide encoding a nuclease, a purified nuclease protein, or any combination thereof into the host cell, in particular, host cells that are otherwise difficult to transform/transfect using conventional techniques, such as plants. Biolistics work by binding the transformation reaction to microscopic gold particles, and then propelling the particles using compressed gas at the target cells.

In some embodiments, the polynucleotide comprising nucleic acid encoding the nuclease is an expression vector that allows for the expression of a nuclease within a host cell. Suitable expression vectors include but are not limited to those known for use in expressing genes in *Escherichia coli*, yeast, or mammalian cells. Examples of *Escherichia coli* expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2µ plasmids. In some embodiments, a polynucleotide encoding a nuclease can be modified to substitute codons having a higher frequency of usage in the host cell, as compared to the naturally occurring polynucleotide sequence. For example the polynucleotide encoding the nuclease can be modified to substitute codons having a higher frequency of usage in S. cerevisiae, as compared to the naturally occurring polynucleotide sequence.

In some embodiments where the nuclease functions as a heterodimer requiring the separate expression of each monomer, as is the case for zinc finger nucleases and TAL-effector nucleases, each monomer of the heterodimer may be expressed from the same expression plasmid, or from different plasmids. In embodiments where multiple nucleases are introduced to the cell to effect double-strand breaks at different target sites, the nucleases may be encoded on a single plasmid or on separate plasmids.

In certain embodiments, the nuclease expression vector further comprises a selectable marker that allows for selection of host cells comprising the expression vector. Such selection can be helpful to retain the vector in the host cell for a period of time necessary for expression of sufficient amounts of nuclease to occur, for example, for a period of 12, 24, 36, 48, 60, 72, 84, 96, or more than 96 hours, after which the host cells may be grown under conditions under which the expression vector is no longer retained. In certain embodiments, the selectable marker is selected from the group consisting of: URA3, hygromycin B phosphotransferase, aminoglycoside phosphotransferase, zeocin resistance, and phosphinothricin N-acetyltransferase. In some embodiments, the nuclease expression vector may comprise a counter-selectable marker that allows for selection of host cells that do not contain the expression vector subsequent to integration of the one or more donor nucleic acid molecules. The nuclease expression vector used may also be a transient vector that has no selection marker, or is one that is not selected for. In particular embodiments, the progeny of a host cell comprising a transient nuclease expression vector loses the vector over time.

In certain embodiments, the expression vector further comprises a transcription termination sequence and a promoter operatively linked to the nucleotide sequence encoding the nuclease. In some embodiments, the promoter is a constitutive promoter. In some embodiments, the promoter is an inducible promoter. Illustrative examples of promoters suitable for use in yeast cells include, but are not limited to the promoter of the TEF1 gene of K. lactis, the promoter of the PGK1 gene of Saccharomyces cerevisiae, the promoter of the TDH3 gene of Saccharomyces cerevisiae, repressible promoters, e.g., the promoter of the CTR3 gene of Saccharomyces cerevisiae, and inducible promoters, e.g., galactose inducible promoters of Saccharomyces cerevisiae (e.g., promoters of the GAL1, GAL7, and GAL10 genes).

In some embodiments, an additional nucleotide sequence comprising a nuclear localization sequence (NLS) is linked to the 5' of the nucleotide sequence encoding the nuclease. The NLS can facilitate nuclear localization of larger nucleases (>25 kD). In some embodiments, the nuclear localization sequence is an SV40 nuclear localization sequence. In some embodiments, the nuclear localization sequence is a yeast nuclear localization sequence.

A nuclease expression vector can be made by any technique apparent to one skilled in the art. In certain embodiments, the vector is made using polymerase chain reaction (PCR) and molecular cloning techniques well known in the art. See, e.g., PCR Technology: Principles and Applications for DNA Amplification, ed. HA Erlich, Stockton Press, New York, N.Y. (1989); Sambrook et al., 2001, Molecular Cloning—A Laboratory Manual, 3rd edition, Cold Spring Harbor Laboratory, Cold Spring Harbor, NY.

6.7 Kits

In another aspect, provided herein is a kit useful for performing the methods of genomically integrating one or more exogenous nucleic described herein. In some embodiments, the kit comprises:

(a) a host cell comprising a plurality of exogenous landing pads integrated in a host cell's genome, wherein each exogenous landing pad comprises a nuclease target sequence (NTS) positioned between an upstream landing pad homology sequence (ULP) and a downstream landing pad homology sequence (DLP);

(b) a plurality of exogenous donor nucleic acids, wherein each exogenous donor nucleic acid (ES) comprises: a nucleic acid of interest (D) positioned between an upstream library sequence (UL) and a downstream library sequence (DL), wherein each (UL) is capable of homologously recombining at any upstream landing pad homology sequence (ULP) and each (DL) is capable of homologously recombining at any downstream landing pad homology sequence (DLP) of landing pads in a host cell's genome; and (c) one or more nucleases (N) capable of cleaving any (NTS) in the landing pads.

In some embodiments, (D) is selected from the group consisting of a selectable marker, a promoter, a nucleic acid sequence encoding an epitope tag, a gene of interest, a reporter gene, a nuclei acid sequence encoding a termination codon. In some embodiments, the kit further comprises a plurality of primer pairs, wherein each primer pair is capable of identifying integration of exogenous donor nucleic acids by PCR.

In some embodiments, the kit further comprises instructions for use that describe methods of integrating one or more exogenous donor nucleic acids into any landing pads of a host cell.

7. EXAMPLES

7.1 Example 1: CLiX Parent Strain Construction and Transformation

To generate a CLiX (combinatorial library integration using X-cutter) parent strain, DNA "landing pads" consisting of "upstream library" (UL) and "downstream library" (DL) sequences flanking an endonuclease recognition site (F-CphI) were integrated into 3 separate genomic loci of Saccharomyces cerevisiae CEN.PK2. Specifically, landing pads were targeted to the intergenic regions downstream of ALG1 (iALG1), MGA1 (iMGA1), and YCT1 (iYCT1). DNA integration at each of these loci was previously confirmed to have no measurable impact on strain phenotype. UL and DL sequences were derived from a random sequence generator with constraints of 500 bp length and 50% GC content. These sequences were manually curated to remove tandem and inverted repeats, DNA secondary structure, and any significant homology to known biological sequences based on nucleotide and translated BLAST search (BLASTn and BLASTx, respectively). Nucleotide sequences for each landing pad including locus targeting sequences are provided as SEQ ID NO: 8-10.

Each landing pad was integrated into CEN.PK2 with standard molecular biology techniques in an optimized lithium acetate (LiAc) transformation. Briefly, cells were grown overnight in yeast extract peptone dextrose (YPD) media at 30° C. with shaking (200 rpm), diluted to an $OD_{600}$ of 0.1 in 100 mL YPD, and grown to an $OD_{600}$ of 0.6-0.8. For each transformation, 5 mL of culture was harvested by centrifugation, washed in 5 mL of sterile water, spun down again, resuspended in 1 mL of 100 mM LiAc, and transferred to a microcentrifuge tube. Cells were spun down (13,000×g) for 30 seconds, the supernatant was removed, and the cells were resuspended in a transformation mix consisting of 240 µL 50% PEG, 36 µL 1 M LiAc, 10 µL boiled salmon sperm DNA, and 74 µL of donor DNA. Following a heat shock at 42° C. for 40 minutes, cells were recovered overnight in YPD media before plating on selective media. Landing pad integration was confirmed by colony PCR with primers targeting the 5' and 3' integration flanks.

7.2 Example 2: Comparing Genomic Integration of "Locked Promoter" and "Split Promoter" Designs A number of design variants are compatible with CLiX integrations. "Locked promoter" designs contain fixed promoters driving individual open reading frames (ORFs) flanked by UL and DL homology. "Split" designs consist of multiple parts that are combined through recombination at small homologous "linker" sequences. Most commonly, one part is a "split promoter" consisting of a UL homology sequence followed by a promoter and DNA linker, and a second part is a promoterless ORF consisting of a DNA linker, an open reading frame, and a DL homology sequence. Using this design variant, a pooled transformation of multiple "split promoters" can be used to combinatorially titrate the expression of each ORF. We used DNA constructs encoding fluorescent proteins (GFP, RFP, and BFP) along with "spacer" constructs containing a spacer sequence to test both locked and slit promoter designs.

For locked promoter designs, each fluorescent gene was transcribed by a pGAL1 promoter and flanked by UL and DL homology sequences to enable integration at each landing pad. The "spacer" construct consisted of a 1 kb "spacer" sequence flanked by UL and DL homology. We pooled equimolar amounts of these 4 constructs together (locked promoter GFP, RFP, BFP, and "spacer", see FIG. 10A) to a total DNA concentration of 1 µg and transformed the CLiX parent strain. 1 µg of a G418-resistant plasmid encoding F-CphI endonuclease was also provided in the transformation to cut each CLiX integration site. The transformation was plated on agar plates containing G418 to select for cells that expressed CphI and repaired each double strand break with the provided donor DNA. 100s of colonies were recovered on a G418 plate from the pooled transformation containing donor DNA and CphI, while no colonies were present on a control transformation containing CphI only. This result indicates that CphI cuts at high efficiency and repair mechanisms such as non-homologous end joining (NHEJ) are unlikely to yield false positives. 176 colonies were picked into 96 well plates containing BSM media+2% sucrose and incubated overnight at 30° C. The following morning, a sub-inoculation was performed into 96 well plates containing BSM media+4% galactose to induce expression from pGAL1. After a 24 hour incubation, GFP, RFP, and BFP fluorescence was measured for each well.

For split designs, we constructed 9 split promoters of different expression strengths to pair with promoterless ORFs for GFP, RFP, BFP, and a "spacer" sequence (FIG. 10B). pGAL 1, the strongest promoter tested, was present to enable comparisons to single ORF designs. The other 8 tested split promoters ranged from 1% (pSLN1) to 75% (pGAL1_v20) the expression level of pGAL1 as quantified by GFP fluorescence. All 13 constructs were pooled together in equimolar amounts to a final concentration of 1 µg and transformed into the CLiX parent strain along with F-CphI. 528 colonies were assessed for GFP, RFP, and BFP fluorescence following a 24 hour incubation in BSM media+4% galactose as described above.

For the locked promoter designs, each fixed-promoter fluorescent construct can vary by copy number only (i.e., how many times the construct integrated into the 3 available landing pads). Accordingly, we observed that fluorescent values from each measured well fell into 4 distinct "bins" corresponding to 0×, 1×, 2×, and 3× integrations. The 1×, 2×, and 3× "bins" for GFP fluorescence, corresponding to the number of pGAL1>GFP integrations, are clearly visible as hatch marked columns in FIG. 10C (the 0× bin, <300 RFU, is removed from this plot for easier viewing). Note that this pattern was observed for each fluorescent protein.

For split designs, each fluorescent construct can vary in promoter strength (i.e., which split promoter recombined with the promoterless-ORF) and copy number. Since the additional promoters are weaker than pGAL1, we anticipated that fluorescent measurements from split designs would "fill in" the spaces between 1×, 2×, and 3× copies of each locked promoter fluorescent construct. As observed in FIG. 10C, RFU values for split promoters (gray bars) did indeed cover an expanded range. Binning by 200 RFU, nearly every expression level from 0× to 3× copies of pGAL1>GFP was covered by a single transformation.

7.3 Example 3: Genomic Integration Efficiency Using CLiX Parent Strain

This example provides results which demonstrate simultaneous integration at three different landing pads of a *S. cerevisiae* host following the induction of targeted double-stranded breaks in the host cell's genome. The strains A, B, and C are derived from the same *S. cerevisiae* strain, and they all comprise three CLiX landing pads located in the downstream intergenic regions of ALG1, MGA1, and YCT1. The differences between these strains are the lengths of upstream and downstream landing pad homology sequences (UI/DL). The lengths of each of UL and DL of the landing pads in strain A is 500 base pairs; the lengths of each of UL and DL of the landing pads in strain B is 200 base pairs; and the lengths of each of UL and DL of the landing pads in Strain C is 100 base pairs. Strain A was transformed with a "locked" stitch design (i.e., a GFP operably linked to a promoter), and in a separate experiment, strain A was also transformed with a "split" promoter design where two separately DNA constructs are used to introduce a GFP and different promoters of varying strengths similar to those described in Example 2. Strain B was transformed with DNA constructs of a "split" promoter design. Strain C was transformed with DNA constructs of a "split" promoter design. In all DNA constructs of either "locked" stitch design or "split" promoter design, each of the upstream library sequence and downstream library sequence used for homologous recombination is 500 base pairs. Integrations were validated by cPCR, fluorescence measurement, and Sanger sequencing.

As shown in FIG. 11, the success rate of integration into all three landing pads were greater than 95%.

7.4 Example 4: Performance of Combinatorial Integration of Library Components and Landing Pads in Production of Isoprenoid As illustrated in FIG. 12, three combinatorial "CLiX" landing pads were integrated into a *Saccharomyces cerevisiae* CEN.PK2 strain engineered to produce an isoprenoid compound at high titers. Methods for transformation and landing pad integration are described in Examples 1 and 2. For library integration, 6 constructs consisting of a UL homology sequence, barcode sequence, "Y" nuclease recognition, promoter sequence, and linker sequence were paired with 8 promoterless ORFs consisting of a linker sequence, open reading frame, "Z" nuclease recognition site, barcode sequence, and DL homology sequence. ORFs were chosen that were hypothesized to improve isoprenoid titers. A $9^{th}$ DNA construct of similar architecture was added that consisted of a linker, "stuffer" sequence consisting of random DNA nucleotides, "Z" nuclease recognition site, barcode sequence, and DL homology sequence. The intent of this construct was to allow for integrations of 1 or 2 ORFs since the integration of this random sequence should have no impact on strain performance.

This library of 15 constructs was pooled together in equimolar amounts to a final concentration of 1 μg and transformed into the parent strain along with 1 μg of a G418-resistant plasmid encoding F-CphI. Colonies were recovered on solid media consisting of LB+G418 as previously described in 1.1. 5760 colonies were picked into 96 well plates containing minimal media (BSM) with 2% sugar. After overnight growth, cultures were subinoculated into liquid media containing either 4% sugar 1 or 6% sugar 2. After 3 days of growth, cultures were assayed for isoprenoid titer using a UV-based assay. A "parent" control strain (the isoprenoid-producing strain with 3 landing pads but no integrations) was provided for comparison.

42 strains were selected from the library that had improved performance in sugar 1, sugar 2, or both sugars (known as "hits"). These strains were re-assayed for isoprenoid titer with increased replication (12 replicates per strain) and compared to 42 "hits" from a separate library where the parent strain was mutagenized by UV. 37 of the 42 strains from the combinatorial library repeated as significantly improved over parent in terms of isoprenoid titer. The average effect size, or magnitude of improvement over parent, was dramatically increased over the mutagenesis library.

The 42 strains that were assayed with increased replication were genotyped using standardized barcodes to determine the identity of the promoter and ORF that integrated at each locus. Instances of ORF1, a transcriptional activator, were enriched over the rest of the library. P3, the weakest promoter in the library, was paired with ORF1 in over 75% of the integrations. These results suggested that ORF1 overexpression was an effective way to increase isoprenoid titer, but only when expressed at a low level.

These results shown in FIG. 12 demonstrate that the combinatorial integration of library components (e.g., promoters of varying expression strengths and ORFs) is a powerful tool in simultaneously titrating expression of various genes to determine an optimal balance of co-expression of genes to maximize the production of a target molecule. The combinatorial integration of library components into landing pads can further provide advantages of generating an even greater variation of genotypes and further improving resulting phenotypes for the strains.

One or more features from any embodiments described herein or in the figures may be combined with one or more features of any other embodiment described herein in the figures without departing from the scope of the invention.

A recitation of "a," "an," or "the" is intended to mean "one or more" unless specifically indicated to the contrary.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed:

1. A method for integrating one or more exogenous donor nucleic acids into a yeast host cell's genome, the method comprising:
contacting a host cell, the host cell comprising one or more exogenous landing pads integrated in the host cell's genome, wherein each exogenous landing pad comprises a nuclease target sequence (NTS) positioned between an upstream landing pad homology sequence (ULP) and a downstream landing pad homology sequence (DLP), with:
(i) one or more exogenous donor nucleic acids (ES), comprising a nucleic acid of interest (D) positioned between an upstream library sequence (UL) and a downstream library sequence (DL), wherein each (UL) is capable of homologously recombining at any (ULP), and each (DL) is capable of homologously recombining at any (DLP) of any of the one or more exogenous landing pads
wherein any of the exogenous donor nucleic acids (ES) is integrated at any of the exogenous landing pads and is independent of genomic sequences surrounding each landing pad, and
wherein the one or more exogenous landing pads are selected from SEQ ID NOs: 8, 9, and 10.

2. The method of claim 1, wherein the one or more exogenous donor nucleic acids ES comprise upstream library sequences UL that are identical to one another and downstream library sequences DL that are identical to one another.

3. The method of claim 1, wherein each of ULP and DLP comprises about 100 base pairs of homology with each of UL and DL, respectively.

4. The method of claim 1, wherein each of ULP and DLP comprises about 200 base pairs of homology with each of UL and DL, respectively.

5. The method of claim 1, wherein each ULP and DLP comprises about 500 base pairs of homology with each of UL and DL, respectively.

6. The method of claim 1, wherein each of UL and DL comprises about 500 base pairs, wherein at least a portion of each of UL and DL is at least 70% identical to ULP and DLP, respectively, for host cell-mediated homologous recombination.

7. The method of claim 1, wherein the host cell comprises 2, 3, 4, 5, 6, 7, 8, 9, 10, 11, 12, 13, 14, 15, 16, 17, 18, 19, or 20 exogenous landing pads.

8. The method of claim 1, wherein the one or more exogenous landing pads are integrated at selected neutral loci in the host cell's genome.

9. The method of claim 1, wherein the one or more exogenous landing pads are integrated at intergenic regions in the host cell's genome.

10. The method of claim 1, wherein the host cell comprises two or more exogenous landing pads, wherein each UL is capable of homologously recombining at any ULP, and each DL is capable of homologously recombining at any DLP, of any of the one or more exogenous landing pads.

11. The method of claim 1, wherein the one or more exogenous donor nucleic acids (ES), a group of component polynucleotides, or both the ES and the group of component polynucleotides are capable of integrating at any of the one or more landing pads, independent of genomic sequences surrounding each exogenous landing pad.

12. The method of claim 1, wherein the host cell further comprises at least one secondary landing pad integrated in the host cell's genome, the secondary landing pad comprising a secondary nuclease target sequence positioned between a secondary upstream landing pad homology sequence and a secondary downstream landing homology pad sequence, wherein;
(a) the secondary upstream landing pad sequence is different from ULP of the one or more exogenous landing pads;
(b) the secondary downstream landing pad sequence is different from DLP of the one or more exogenous landing pads;
(c) the secondary nuclease target sequence is different from the NTS of the one or more exogenous landing pads; or
(d) any combination thereof.

13. The method of claim 1, wherein the yeast host cell is selected from *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtznanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phafia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Toruslaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis,* and *Zygozyma.*

14. The method of claim 1, wherein the yeast host cell is *Saccharomyces cerevisisae.*

15. A yeast host cell genetically modified according to the method of claim 1.

16. The yeast host cell of claim 15, wherein the yeast host cell belongs to a genera selected from *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtznanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phafia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Toruslaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis,* and *Zygozyma.*

17. The yeast host cell of claim 16, wherein the yeast host cell is *Saccharomyces cerevisiae.*

\* \* \* \* \*

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Leu Ala Gly Leu Ile Asp Ala Asp Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Gly Ile Tyr Tyr Ile Gly
```

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
tagggataac agggtaat                                                     18

<210> SEQ ID NO 4
<211> LENGTH: 31
<212> TYPE: DNA
<213> ORGANISM: Artificial Sequence
<220> FEATURE:
<223> OTHER INFORMATION: Synthetic

<400> SEQUENCE: 4
tatgtcgggt gcggagaaag aggtaatgaa a                                      31

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
gatgcacgag cgcaacgctc acaa                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
gcgtagctgc ccagtatgag tcag                                              24

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
acgtgcacta cgtagagggt cgcaccgcac cgatctacaa                             40

<210> SEQ ID NO 8
<211> LENGTH: 2024
<212> TYPE: DNA
<213> ORGANISM: Artificial Sequence
<220> FEATURE:
<223> OTHER INFORMATION: Synthetic

<400> SEQUENCE: 8
ttatacagtt acatagtact acctctaata cacattcatg attaacaatg tttcaaacaa        60
tataaagtcc cgataacgac cttttgaagt ggtgacgtta ccgctcttcg ttgacaagat       120
tcaagagggc tgtcagaata acagctatca tggtggaaag taggtgaccc tttgaacaag       180
gcagcatata tccatcgact atcatgttcc taaaatgtta tcatagccgg cgttagaaga       240

```
tggcgcatat tattatttta ttagaatgag ttataacagt catcaaactt agcgaaagcc    300
gaagtgtaag aactaaaaag tccactataa aaaatgaat cacagcgtac aaaaggaaat    360
aacgataact gtgatgctat gtaaaactat cgtctttcct ttgttgataa atatatcctc    420
aaggactact tcttttatat ttcttgtagg tgatgttgtg ccctcatcgt taatttgaat    480
cccagcaatt atcagacagt acatggcaat aaccacgcct ttctacttct agaggagaaa    540
agtattgaca tcagcgctcc cggcacaagg gccaaagaag tctacaattt cttatttccg    600
aatcacttgc gtctccttgc ggctataaca ccgaccgcaa ttcatagtag cctggcggaa    660
cagataggtc taattagctt aagagagaat atcctgggat cattcagtag taaccataaa    720
cttacgctgg ggcttcttcg gcggattatt acagttacca accaggagat ttgaagtata    780
tcagttgagg atttagccgg gctatccggt aatctccaaa ttaaatcata ccgttcgatc    840
aaggctagaa ttacttaccg gcctgttcca agcctgcgct atactcaccc actctcccgc    900
ttatccgtcc gagcggaggc agtgcgatcc tccgttaaga tattcttacg tgtgacgtag    960
ctatgtatat tgcagagctg gcgaacgcgt tgaacacttc gatgcacgag cgcaacgctc   1020
acaaggttct atacatacgt ggcccagtag ttatccaata tcggaacatc aattgtacat   1080
cgggccggct taatcttgta atcacggaag tagccgtaag acaaataatt caataaagat   1140
gacgtattgc tagtttacct caaggtgtca cgcgccatct ctgagcaggt gggccgacga   1200
gacattatcc ctgatttatt cactactaat agtactcacg gcgcaatacc agcacagcct   1260
agtctcgcca gaatcctggt cagcatacga aagagcttaa ggcaggccaa ttcgcactgt   1320
cagggtcact tggctgttta gcactaccga caggtacgct agtaagcgtt cttcctacca   1380
gaggtctgtg gccgcgtggt ctaaagtgcg gctttcgtat ttgctgctcg tgtttactct   1440
cacaaacttg acctgcacgc caaagagttg cttcttgtgg aactcgacaa cgcaactacg   1500
cgacggatct acgtcacagc gtgccttaaa tcaaggaaca ctaaccatgt atgacataca   1560
aggagcacta ccactgattt caacagatat taatggtagt tttttgcaga atcgtaaggt   1620
agatcagtgg aaatagtaga aaagggctag tttagattca aaatttggta acacgtaacg   1680
tcgcgctttg gaaaatatac ctcaatgctg actacttaag atggcaaata gccttgtcaa   1740
atttcctacg gaatgttatt ttcattacgt ccttctttt caatgtactt attcataaat   1800
gggacactat cttgttgcaa aaggtacttt gtattttggt attaacatct cgcctatttt   1860
tcatacagaa acactactta tcgctatcta tttgatgtgg tattgcttgg ccatgaggat   1920
accttgagct acgttttgaa cacgtgcatc caacttgtag ccttgttgat ccaacttaac   1980
catttcatca ggaaacttgt gcaactcaac gctaaagcat tcga                   2024
```

<210> SEQ ID NO 9
<211> LENGTH: 2024
<212> TYPE: DNA
<213> ORGANISM: Artificial Sequence
<220> FEATURE:
<223> OTHER INFORMATION: Synthetic

<400> SEQUENCE: 9

```
aactgcccta cccctttcaag agactacgaa tacatcatcg accttaactt ctctgacgtc    60
cagcataatt cccaagagta tacctataat cacgaaaggt gaagtcgcca ctaaaccagc   120
atcttactga attattttca acagaacaca tcgcatccaa ctgaacaaac tgttaccgct   180
gttgatacca aggaacattc agtgaacgta gggaagaacg aacattctcc atattttgc    240
```

| | | | | |
|---|---|---|---|---|
| atactagata | caagggggaa | gaatgcaatt | atttcacaaa | ccgaaagaaa | aagaatcaca | 300 |
| agctatgttt | gctattatca | attttctta | tgattaattt | aacataaatt | atggccttt | 360 |
| tcattccggc | tgcgcttgtt | ctccattttt | ttttttttt | ttgagaaaac | tttaaaaatt | 420 |
| tcaaatgtaa | gaaagtagag | cagatctttt | agcaaggatc | cgcttaacat | tccaacaaaa | 480 |
| aaggaaaaat | aaaacaataa | acatggcaat | aaccacgcct | ttctacttct | agaggagaaa | 540 |
| agtattgaca | tcagcgctcc | cggcacaagg | gccaaagaag | tctacaattt | cttatttccg | 600 |
| aatcacttgc | gtctccttgc | ggctataaca | ccgaccgcaa | ttcatagtag | cctggcggaa | 660 |
| cagataggtc | taattagctt | aagagagaat | atcctgggat | cattcagtag | taaccataaa | 720 |
| cttacgctgg | ggcttcttcg | gcggattatt | acagttacca | accaggagat | ttgaagtata | 780 |
| tcagttgagg | atttagccgg | gctatccggt | aatctccaaa | ttaaatcata | ccgttcgatc | 840 |
| aaggctagaa | ttacttaccg | gcctgttcca | agcctgcgct | atactcaccc | actctcccgc | 900 |
| ttatccgtcc | gagcggaggc | agtgcgatcc | tccgttaaga | tattcttacg | tgtgacgtag | 960 |
| ctatgtatat | tgcagagctg | gcgaacgcgt | tgaacacttc | gatgcacgag | cgcaacgctc | 1020 |
| acaaggttct | atacatacgt | ggcccagtag | ttatccaata | tcggaacatc | aattgtacat | 1080 |
| cgggccggct | taatcttgta | atcacggaag | tagccgtaag | acaaataatt | caataaagat | 1140 |
| gacgtattgc | tagtttacct | caaggtgtca | cgcgccatct | ctgagcaggt | gggccgacga | 1200 |
| gacattatcc | ctgatttatt | cactactaat | agtactcacg | gcgcaatacc | agcacagcct | 1260 |
| agtctcgcca | gaatcctggt | cagcatacga | aagagcttaa | ggcaggccaa | ttcgcactgt | 1320 |
| cagggtcact | tggctgtta | gcactaccga | caggtacgct | agtaagcgtt | cttcctacca | 1380 |
| gaggtctgtg | ccgcgtggt | ctaaagtgcg | gctttcgtat | ttgctgctcg | tgtttactct | 1440 |
| cacaaacttg | acctgcacgc | caaagagttg | cttcttgtgg | aactcgacaa | cgcaactacg | 1500 |
| cgacggatct | acgtcacagc | gtgctaattt | tttttactcg | cgcgcttccg | acttttgaaa | 1560 |
| gaaggagcaa | taaagttaaa | taatgtaat | taaattatgc | tttttaggc | aagttcggga | 1620 |
| ctttgttgcc | acgtattgct | cttctatgca | agcacttcac | tccttttctt | tcatctctgt | 1680 |
| tttcttccac | tggctggaag | cttgagggtt | gcctcttgat | tctttatcgc | ctgcaaccat | 1740 |
| tgccttgttc | cgtcctctca | aggcgttcct | tccgtgcttt | taaatacta | gaatcattcg | 1800 |
| agacgtattt | atgagcatgt | tacttcttga | tgtttatcta | agagggtgt | ttaggttatc | 1860 |
| cgcattattt | ttaaagttttt | aaggttacat | catttattca | gacgcgttcg | gaggagagtg | 1920 |
| cattcaccaa | gatgtaaatt | tcttcagttt | tccggattag | gattggaaaa | atgaagaaaa | 1980 |
| atagctgcag | aagagccgaa | aataggtcag | aaaaaaaaaa | agac | | 2024 |

<210> SEQ ID NO 10
<211> LENGTH: 2024
<212> TYPE: DNA
<213> ORGANISM: Artificial Sequence
<220> FEATURE:
<223> OTHER INFORMATION: Synthetic

<400> SEQUENCE: 10

| | | | | |
|---|---|---|---|---|
| tttagaaaac | gaaactttta | tatatccttt | gtaaatattg | atgttttgtt | gtgtaaatgt | 60 |
| tctatctgac | acttaataat | tagaaaatta | attttttaaa | cttccggct | gcaagaaaga | 120 |
| ggaactgtgt | ctctttgaaa | ggcacaattt | cccaaagaat | catttacaat | ggtaaatagc | 180 |
| ttactgctta | gaaaataata | gataattgaa | taaatttata | gaggaaattc | ttgacaattt | 240 |
| cttcaaaaca | gccggtaaaa | gtccattaaa | gattagtttt | tcttaaataa | atcacctaaa | 300 |

-continued

```
ctttcaaatt tagcataaaa aacatgtaga tatttgttct ctgtacttta taatctaaca      360
ttttataaga cagagactag taaccctct  agcctgtggt taaaatacgc aaaacctttg      420
aaccctcaat atttttgcca taataatgac aactatattg tacccatttg ttcttgagtt      480
gtccgtatgg atggaaagca acatggcaat aaccacgcct ttctacttct agaggagaaa      540
agtattgaca tcagcgctcc cggcacaagg gccaagaag  tctacaattt cttatttccg      600
aatcacttgc gtctccttgc ggctataaca ccgaccgcaa ttcatagtag cctggcggaa      660
cagataggtc taattagctt aagagagaat atcctgggat cattcagtag taaccataaa      720
cttacgctgg ggcttcttcg gcggattatt acagttacca accaggagat ttgaagtata      780
tcagttgagg atttagccgg gctatccggt aatctccaaa ttaaatcata ccgttcgatc      840
aaggctagaa ttacttaccg gcctgttcca agcctgcgct atactcaccc actctcccgc      900
ttatccgtcc gagcggaggc agtgcgatcc tccgttaaga tattcttacg tgtgacgtag      960
ctatgtatat tgcagagctg gcgaacgcgt tgaacacttc gatgcacgag cgcaacgctc     1020
acaaggttct atacatacgt ggcccagtag ttatccaata tcggaacatc aattgtacat     1080
cgggccggct taatcttgta atcacggaag tagccgtaag acaaataatt caataaagat     1140
gacgtattgc tagtttacct caaggtgtca cgcgccatct ctgagcaggt gggccgacga     1200
gacattatcc ctgatttatt cactactaat agtactcacg gcgcaatacc agcacagcct     1260
agtctcgcca gaatcctggt cagcatacga aagagcttaa ggcaggccaa ttcgcactgt     1320
cagggtcact tggctgttta gcactaccga caggtacgct agtaagcgtt cttcctacca     1380
gaggtctgtg gccgcgtggt ctaaagtgcg gctttcgtat ttgctgctcg tgtttactct     1440
cacaaacttg acctgcacgc caaagagttg cttcttgtgg aactcgacaa cgcaactacg     1500
cgacggatct acgtcacagc gtgctatgcc cagaaaattt gtaaatgata atttacataa     1560
caattcaaaa catattgatg tttttcgtgg gtaaccatag ttcttggaat gtcaactgag     1620
ggtatttgca cttcaaaaaa aaaaatttat taaatgagac tatatacagt gagcacaacc     1680
tgtctaatac aacggcaaaa attatataca ttggtagatt ttcaaaattg aactctttgt     1740
gctaaagaat tgtcacaaca gtttaaaaaa tagtttgaat tcttcaaatt gaccccatat     1800
taataagacc tgatgcgatt ccggtctcac ccagattaga gagggaattt aattttctta     1860
ggaccgtagc taccaaaaat ctttgtgtgg tattgattat atgatcgtgc ttgcgaaaaa     1920
aatagaagac taaagtagc  attagtttac taactttctc ctcgtatctt tcaaatttgt     1980
attcccctca aaagttactc aggttaggga aaattccaag tagc                      2024
```